US00RE48522E

(19) United States
(12) Reissued Patent
Straten et al.

(10) Patent Number: US RE48,522 E
(45) Date of Reissued Patent: Apr. 20, 2021

(54) SURVIVIN-DERIVED PEPTIDES AND USES THEREOF

(71) Applicant: SURVAC APS, Frederiksberg C (DK)

(72) Inventors: Eivind Per Thor Straten, Hvidorve (DK); Mads Hald Andersen, Hellerrup (DK)

(73) Assignee: SURVAC APS, Frederiksberg C (DK)

(21) Appl. No.: 16/039,999

(22) Filed: Jul. 19, 2018

Related U.S. Patent Documents

Reissue of:
(64) Patent No.: 9,534,030
Issued: Jan. 3, 2017
Appl. No.: 13/630,862
Filed: Sep. 28, 2012

U.S. Applications:
(60) Division of application No. 10/543,755, filed as application No. PCT/DK2004/000062 on Jan. 30, 2004, now Pat. No. 8,318,174, which is a continuation of application No. 10/354,090, filed on Jan. 30, 2003, now abandoned, and a continuation of application No. 10/715,417, filed on Nov. 19, 2003, now Pat. No. 7,892,559, which is a continuation-in-part of application No. 10/354,090, filed on Jan. 30, 2003, now abandoned.

(60) Provisional application No. 60/352,284, filed on Jan. 30, 2002.

(51) Int. Cl.

| | |
|---|---|
| ***A61K 39/002*** | (2006.01) |
| ***C07K 14/47*** | (2006.01) |
| ***G01N 33/574*** | (2006.01) |
| ***A61K 47/00*** | (2006.01) |
| ***A61K 39/39*** | (2006.01) |
| ***A61K 39/00*** | (2006.01) |
| ***A61K 38/00*** | (2006.01) |
| *A61K 47/51* | (2017.01) |

(52) U.S. Cl.
CPC ..... *C07K 14/4747* (2013.01); *A61K 39/0011* (2013.01); *A61K 39/00115* (2018.08); *C07K 14/4738* (2013.01); *G01N 33/574* (2013.01); *G01N 33/57484* (2013.01); *A61K 38/00* (2013.01); *A61K 39/002* (2013.01); *A61K 39/39* (2013.01); *A61K 47/00* (2013.01); *A61K 47/51* (2017.08); *A61K 2039/5154* (2013.01); *A61K 2039/5158* (2013.01)

(58) Field of Classification Search
CPC ..... A61P 35/00; C07K 7/06
See application file for complete search history.

(56) References Cited

U.S. PATENT DOCUMENTS

| | | | |
|---|---|---|---|
| 6,037,135 | A | 3/2000 | Kubo et al. |
| 6,245,523 | B1 | 6/2001 | Altieri |
| 6,346,389 | B1 | 2/2002 | Altieri |
| 6,572,864 | B1 | 6/2003 | Bukh et al. |
| 2004/0176573 | A1 | 9/2004 | Thor et al. |
| 2004/0210035 | A1 | 10/2004 | Straten et al. |
| 2007/0148184 | A1 | 6/2007 | Straten et al. |

FOREIGN PATENT DOCUMENTS

| | | |
|---|---|---|
| WO | 92/20356 | 11/1992 |
| WO | 94/05304 | 3/1994 |
| WO | WO 97/28816 | 8/1997 |
| WO | WO 1999/50637 | 10/1999 |
| WO | 00/03693 | 1/2000 |
| WO | WO 2002/072631 | 9/2002 |
| WO | WO 03/102023 | 12/2003 |
| WO | WO 03/102023 A1 | 12/2003 |
| WO | WO2004/067023 | 8/2004 |
| WO | WO 2005/049073 | 6/2005 |

OTHER PUBLICATIONS

Restriction Requirement in U.S. Appl. No. 10/543,755 dated Jun. 26, 2008.
Advisory Action in U.S. Appl. No. 10/543,755, dated Mar. 12, 2010.
Restriction Requirement in U.S. Appl. No. 10/354,090 dated Dec. 21, 2005.
Ambrosini et al., "Induction of Apoptosis and Inhibition of Cell Proliferation by Survivin Gene Targeting," The Journal of Biological Chemistry, vol. 273, No. 18, Issue of May 1, pp. 11177-11182 (1998).
Blok et al., A Bispecific Monoclonal Antibody Directed Against Both Membrane-Bound Complement Regulator CD55 and the Renal Tumor-Associated Antigen G250 Enhances C3 Deposition and the Tumor Cell Lysis by Complement, The Journal of Immunology, vol. 160, pp. 3437-3443 (1998).
Fortugno et al., "Survivin Exists in Immunochemically Distinct Subcellular Pools and is Involved in Spindle Microtubule Function," Journal of Cell Science, vol. 115, pp. 575-585, (2002).
Grube et al., "CD8 + Tcells Reactive to Survivin Antigen in Patients with multiple Myeloma," Clinical Cancer Research, vol. 13, No. 3, pp. 1053-1060, Feb. 1, 2007.
Hirohashi et al., "An HLA-24-Restricted Cytotoxic T Lymphocyte Epitope of a Tumor-Associated Protein, Survivin," Clinical Cancer Research, vol. 8, pp. 1731-1739 (2002).
Nijman et al., Identification of peptide Sequences that Potentially Trigger HLA-A2.1 RestrictedCytotoxic T Lymphocytes, European Journal of Immunology, vol. 23, pp. 1215-1219 (1993).
Schmidt et al., "Survivin is a Shared Tumor-Associated Antigen Expressed in a Broad Variety of Malignanciesand Recognized by Specific Cytotoxic T Cells," Blood, vol. 102, No. 2, pp. 571-576 (2003) XP-002283858.

(Continued)

*Primary Examiner* — Bruce R Campell
(74) *Attorney, Agent, or Firm* — Troutman Pepper Hamilton Sanders LLP

(57) ABSTRACT

MHC Class I-restricted peptides derived from the tumor associated antigen, survivin, which peptides are capable of binding to Class I HLA molecules at a high affinity, capable of eliciting INF-γ-producing cells in a PBL population of a cancer patient and capable of in situ detection of cytotoxic T cells in a tumor tissue, therapeutic and diagnostic composition comprising the peptide and uses thereof.

16 Claims, 17 Drawing Sheets

Figure 1:
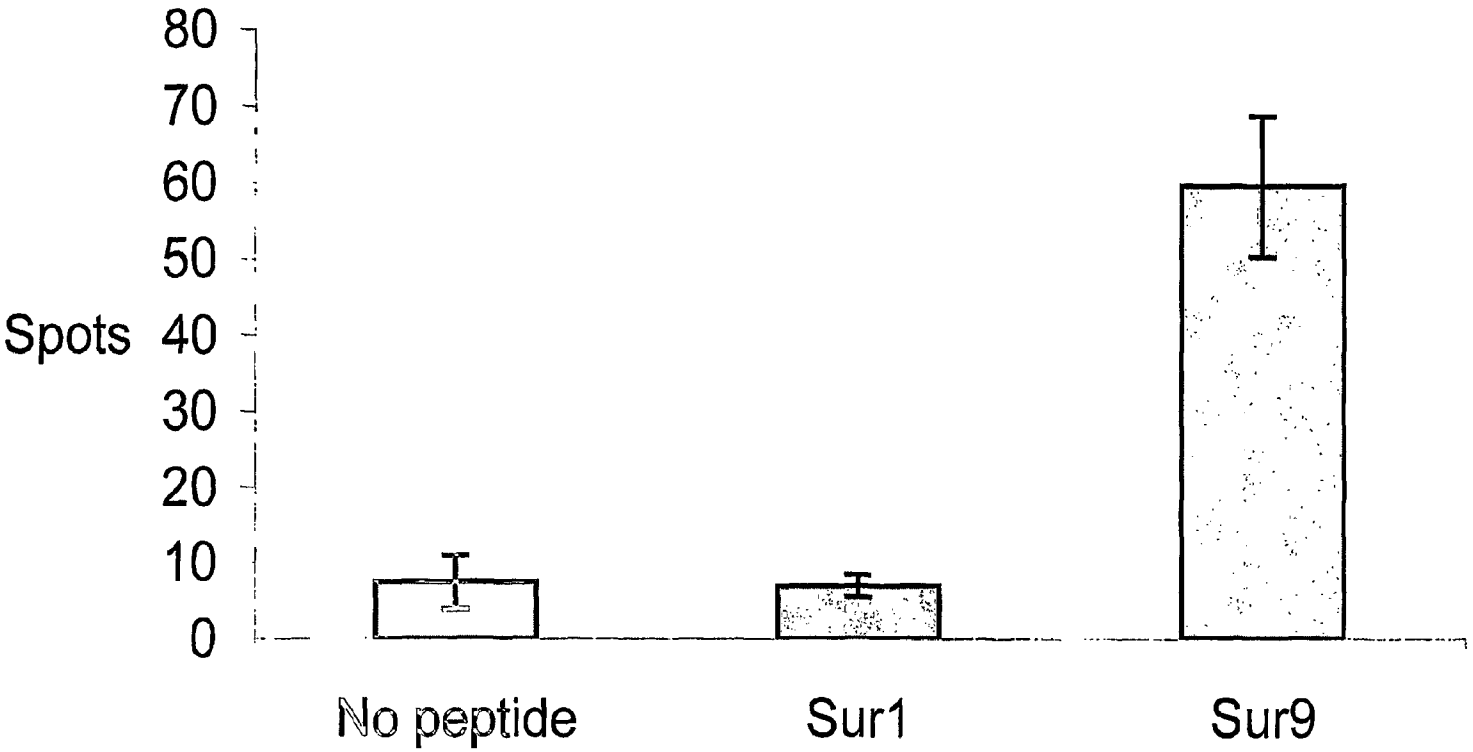

Specification includes a Sequence Listing.

(56) References Cited

OTHER PUBLICATIONS

Schmidt et al., "Survivin is a Shared Tumor-Associated Antigen Expressed in a Broad Variety of Malignanciesand Recognized by Specific Cytotoxic T Cells," Blood, vol. 100, No. 11, Abstract No. 3675, Nov. 16, 2002 XP-002283859.
Sorensen et al., "A Survivin Specific T-Cell Clone from a Breast Cancer Patient Display Universal Tumor Cell Lysis," Cancer Biology & Therapy, vol. 7, No. 12, pp. 1885-1887, Dec. 2008.
Titzer et al, "Vaccination of Multiple Myeloma Patients with Idiotype-Pulsed Dendritic Cells: Immunological and Clinical Aspects," British Journal of Haematology, vol. 108, pp. 805-816 (2000).
International Search Report for International Application No. PCT/DK2004/000062, dated Sep. 1, 2004.
International Preliminary Report on Patentability in International Application No. PCT/DK2004/000062, completed Feb. 24, 2005.
European Search Report for European Application No. 04 706 615, completed Jul. 18, 2006.
Final Office Action dated Oct. 27, 2009 in co-pending U.S. Appl. No. 10/543,755.
Bergmann et al., Journal of Virology, vol. 68, pp. 5306-5310, (1994).
Eisenlhor et al., Journal of Experimental Medicine, vol. 175, pp. 481-487, (1992).
Gileadi et al., Eur. Journal of Immunology, vol. 29, pp. 2213-222, (1999).
Perkins et al., Journal of Immunology, vol. 146, No. 7, pp. 2137-2144, (1991).
Shastri et al., Journal of Immunology, vol. 155, pp. 4339-4346, (1995).
Theobald et al., Journal Exp. Med. vol. 188, No. 6, pp. 1017-1028, (1998).
Wang et al., Cellular Immunology, vol. 143, pp. 284-297, (1992).
Lu, "cFos is Critical for MCF-7 breast Cancer Cell Growth", Oncogene, vol. 24, pp. 6516-6524, (2005).
Muchmore, "Crystal Structure and Mutagenic Analysis of the Inhibitor-of-Apoptosis protein Survivn", Molecular Cell, vol. 6, pp. 173-182, Jul. 2000, XP02201891.
Non-Final Office Acton dated Feb. 18, 2009 in co-pending U.S. Appl. No. 10/543,755.
Non-Final Office Action dated Oct. 7, 2009 in co-pending U.S. Appl. No. 10/354,090.
Wikipedia, The Free Encyclopedia, Cell Culture, Retrieved from the Internet on Aug. 17, 2009 at: http://en.wikipedia.org/w/index/php?title=cell_culture&printable=yes.
Berger et al. Int. J. Cancer, 2004, 111: pp. 229-237.
Bodey et al, Anticancer Research 2000, 20: pp. 2665-2676.
Boon et al. Ann. Rev. Immunol. 2006, 24: pp. 175-208.
Campoli et al., Vaccine. 2002:20, A40-5.
Chaux et al. J. Immunol. 1999, 163: pp. 2928-2936.
Database EMBL. Baculoviral 1AP repeat-containing protein 5 (apoptosis inhibitor survivin) (apoptosis inhibitor 4) (TIAP) May 30, 2000. XP002392545, retrieved from EBI, Database, accession No. 070201.
Emens, Survivin' cancer. Cancer Biol. & Therapy. 2004. 3(2): 180-183.
Gao et al. J. Immunother. 2000, 23: 643-653.
Kuzushima; N. Hayashi, H. Kimura, T. Tsurumi : Efficient identification of HLA-A* 2402-restricted cytomegalovirus- specific CD8+ T-cell epitopes by computer algorithm and an enzyme-linked immunospot assay. BLOOD, Sep. 15, 2001, vol. 98, No. 6, pp. 1872-1881.
Offringa et al. Current Opinion in Immunology 2000, vol. 12, pp. 576-582.
Reker et al. Journal of Immunotherapy. 2004. 27(6): S29-S30.
Van Den Eynde and Morel. Current Opinion Immunol. 2001, 13: 147-153.
Van Den Eynde, B. J. et al., "Tumor antigens recognized by T lymphocytes", Int. J. Clin. Lab. Res., 27:81-86, 1997.
Rosenberg, S. A., "Development of cancer immunotherapies based on identification of the genes encoding cancer regression antigens," J. .Natl. Cancer Inst., 22;88: 1635-1644, 1996.
Marchand, M. et al., "T. Tumor regressions observed in patients with metastdtic melanoma treated with an antigenic peptide encoded by gene MACE-3 and presented, by HLA-Al.," Int. .J. Cancer, 80: 219-230, 1999.
Brossart, P. et al., "W. Her-2/neu-derived peptides are tumor-associated antigens expressed by human renal cell and colon carcinoma lines and are recognized by in vitro induced specific cytotoxic T lymphocytes," Cancer Res., 58: 732-736, 1998.
Brossart, P. et al., "Identification of HLA-A2-restricted T-cell epitopes derived from the MUC1 tumor antigen for broadly applicable vaccine therapies," Blood, 93:4309-4317, 1999.
Vonderheide, R. et al., "The telomerase catalytic subunit is a widely expressed tumor-associated anitgen recognized by cytoxic T lymphocytes," Immunity, 10:673-679, 1999.
Lacasse, E. C. et al., The inhibitors of apoptosis (IAPs) and their emerging role in cancer. Oncogene, 17:3247-3259, 1998.
Grossman, D. et al., "Expression of the apoptosis inhibitor, survivin, in nonmelanoma skin cancer and gene targeting in a keratinocyte cell line," Lab Invest, 79: 1121-1126, 1999.
Andersen, M. H. et al., "An assay for peptide binding to HLA-Cw*0102," Tissue Anitgens, 54:185-190, 1999.
Cornelison, T. L., Human papillomavirus genotype 16 vaccines for cervical cancer prophylaxis and treatment, Curr. Opin. Oncol. 12:466-473, 2000.
Swana, H. S. et al., Tumor content of the antiapoptosts molecule survivin and recurrence of bladder cancer. N. Engl. J. Med., 341: 452-453, 1999.
Salgaller, M. L. et al., Recognition of multiple epitopes in the human melanoma antigen gplOO by peripheral blood lymphocytes stimulated in vitro with synthetic peptides. Cancer Res., 55: 4972-4979, 1995.
Pardoll, D. H., "Cancer vaccines," Nat. Med., 4:525-531, 1998.
Becker, J. et al., "Accumulation of identical T cells in melanoma and vitiligo-like leukoderma," J. Invest. Dermatol., 113: 1033-1038, 1999.
Rohayem, J. et al., "Antibody response to the tumor-associated inhibitor of apoptosis protein survivin in cancer patients," Cancer Res., Apr. 1, 2000;60 (7.):1815.-7., 60: 1815-1817.
Islam, A. et al., "High expression of Survivin, mapped to 17q25, is significantly associated with poor prognostic factors arid promotes cell survival in human neuroblastoma," Oncogene, 19:617-623, 2000.
Lee, K. H. et al., "Functional dissociation between local and systemic immune response during anti-melanoma peptide vaccination," J. Immunol., 161: 4183-4194, 1998.
Altman, J. D. et al., "Phenotypic analysis of antigen-specific T lymphocytes," Science, 274: 94-96, 1996.
Schrama, D. et al., "Oligoclonal I-Cell Receptor Usage of Melanocyte Differentiation Antigen-reactive I Cells in Stage IV Melanoma Patients," Cancer Res., 61: 493-496, 2001.
Scheibenbogen, C. et al., "A sensitive ELISPOT assay for detection of CD8+ T lymphocytes specific for HLA class I-binding peptide epitopes derived *from* influenza proteins in the blood of healthy donors and melanoma patients," Clin. Cancer Res., 3: 221-226, 1997.
de Vries, T. 3., Fourkour, A., Wobbes, I., Verkroost, G., Ruiter, D. 3., and van Muijen, C. N. Heterogeneous expression of immunotherapy candidate proteins gplOO, MART-I, and tyrosinase in human melanoma cell lines and in human melanocytic lesions, Cancer Res., 57: 3223-3229, 1997.
Jager, E. et al., "Inverse relationship of melanocyte differentiation antigen expression in melanoma tissues and CD8+cytotoxic-T-cell responses: evidence for immunoselection of antigen-loss variants in vivo," Int. J. Cancer, 66: 470-476, 1996.
Cormier, J. N. et al., "Comparative analysis of the in vivo expression of tyrosinase, MART-1/Melan-A, and gplOO in metastatic melanoma lesions: implications for immunotherapy," J. Immunother., 21: 27-31, 1998.
Maeurer, N. J., "Tumor escape from immune recognition: lethal recurrent melanoma in a patient associated with downregulation of

(56) References Cited

OTHER PUBLICATIONS the peptide transporter protein TAP-1 and loss of expression of the immunodominant MART-1/Melan-A antigen," J. Clin. Invest. 98: 1633-1641, 1996.
Tamm, I. et al., "IAP-famiiy protein survivin inhibits caspase activity and apoptosis induced by Fas (CD95), Bax, caspases, and anticancer drugs," Cancer Res., 58: 5315-5320, 1998.
Nakagawara, A., "Molecular basis of spontaneous regression of neuroblastoma: role of neurotrophic signals and genetic abnormalities," Hum. Cell, 11: 115-124, 1998.
Renkvist, N. et al., "A listing of human tumor antigens recognized by T cells," Cancer Immunol Immunother., 50: 3-15, 2001.
Gilboa, E., "The makings of a tumor rejection antigen.," Immunity., 11: 263-270, 1999.
Shinozawa, I. et al., "Disturbed expression of the anti-apoptosis gene, survivin, and EPR-1 in hematological malignancies," Leuk. Res, 24: 965-970, 2000.
Granziero, L. et al., "Survivin is expressed on CD4O stimulation and interfaces proliferation and apoptosis in B-cell chronic lymphocytic leukemia," Blood, 97: 2777-2783, 2001.
Andersen, N. H. et al., "Spontaneous cytotoxic I-cell responses against survivin-derived MHC class I-restricted T-cell epitopes in situ as well as ex vivo in cancer patients," Cancer Res, 61: 5964-5968, 2001.
Elvin, J., Potter, C., Elliott, I., Cerundolo, V., and Townsend, A., "A method to quantify binding of unlabeled peptides to class I MHC molecules and detect their allele specificity," J. Immunol Methods, 158: 161-171, 1993.
Ruppert, J., Sidney, J., Celis, F., Kubo, R. I, Grey, H. N., and Sette, A., "Prominent role of secondary anchor residues in peptide binding U.S. Appl. No. 16/039,999 molecules," Cell, 74: 929-937, 1993.
Rammensee, H., Bachmann, J., Emmerich, N. P., Bachor, O. A., and Stevanovic, S., "SYFPEITHI: database for MHC ligands and peptide motifs," Immunogenetics, 50: 213-219, 1999.
Schrama, D., Pedersen Ls, L. O., Keikavoussi, P., Andersen, N. H., Straten, P. P., Brocker, E. B., Kampgen, F., and Brocker, E. C., "Aggregation of antigen-specific I cells at the inoculation site of mature dendritic cells," J. Invest Dermatol., 119: 1443-1448, 2002.
Hicklin, D. J., Marincola, F. N., and Ferrone, S. HLA class I antigen downregulation in human cancers: T-cell immunotherapy revives an old story, Mol. Med. Today, 5: 178-186, 1999.
Sette, A., Vitiello, A., Reherman, B., Fowler, P., Nayersina, R., Kast, W. N., Melief, C. J., Oseroff, C., Yuan, F., and Ruppert, J., "The relationship between class I binding affinity and immunogenicity of potential cytotoxic T cell epitopes," J. Immunol., 153: 5586-5592, 1994.
Parkhurst, M. R., Salgaller, N. L., Southwood, S., Robbins, P. F., Sette, A., Rosenberg, S. A., and Kawakami, Y., "Improved induction of melanoma-reactive CTL with peptides from the melanoma antigen gplOO modified at HLA-A*0201-binding residues," J. Immunol., 157: 2539-2548, 1996.
Guichard, C., Zerbib, A., Le Gal, F. A., Hoebeke, J., Connan, F., Choppin, J., Briand, J. P., and Guillet, J. G., "Melanoma peptide MART-1(27-35) analogues with enhanced binding capacity to the human class I histocompatibility molecule HLA-A2 by introduction of a beta-amino acid residue: implication for recognition by tumor-infiltrating lymphocytes," J. Med. Chem., 43: 3803-3808, 2000.
Clay, T. M., Custer, M. C., McKee, M. D., Parkhurst, N., Robbins, P. F., Kerstann, K., Wunderlich, J., Rosenberg, S. A., and Nishimura, M. I., "Changes in the fine specificity of gplOO(209-217)-reactive T cells in patients following vaccination with a peptide modified at an HLA-A2.1 anchor residue," J. Immunol., 162: 1749-1755, 1999.
Melief, C. J., van der Burg, S. H., Toes, R. E., Ossendorp, F., and Offringa, R., Effective therapeutic anticancer vaccines based on precision guiding of cytolytic T lymphocytes. Immunol. Rev., 188: 177-182, 2002.
Yee, C., Thompson, J. A., Roche, P., Byrd, D. P., Lee, P. P., Piepkorn, N., Kenyon, K., Davis, N. N., Riddell, S. R., and Greenberg, P. D., "Melanocyte destruction after antigen-specific immunotherapy of melanoma: direct evidence oft cell-mediated vitiligo," J. Exp. Med., 192: 1637-1644, 2000.
Simon, R. M., Steinberg, S. M., Hamilton, M., Hildesheim, A., Khleif, S., Kwak, L. W., Mackall, C. L., Schlom, J., Topalian, S. L., and Berzofsky, J. A., "Clinical trial designs for the early clinical development of therapeutic cancer vaccines," J. Clin. Oncol., 19: 1848-1854, 2001.
Non-Final Office Action dated Mar. 23, 2007 in co-pending U.S. Appl. No. 10/715,417.
Final Office Action dated Dec. 12, 2007 in co-pending U.S. Appl. No. 10/715,417.
Non-Final Office Action dated Feb. 17, 2049 in co-pending U.S. Appl. No. 10/715,417.
Non-Final Office Action dated Feb. 18, 2009 in co-pending U.S. Appl. No. 10/543,755.
Berger et al., Int. Journal Cancer, 2004, 111: 229-237.
Blok, Vanessa T.; Daha, Mohamed R.; Tijsma Odette; Harris, Claire L., Morgan, B. Paul, Fleuren, Gert Jan, Gorter, Arko : A Bispecific Monoclonal Antibody Directed Against Both the Membrane-Bound Complement Regulator CD55 and the Renal Tumor-Associated Antigen G250 Enhances C3 Deposition and Tumor Cell Lysis by Complement, The Journal of immunology, 1998, 160: 3437-3413.
Boon et at, Ann. Rev. Inirnunot, 2006, 24: 175-208.
Celis et al. Mol Immunol. 1994 31(18): 1423-30.
Celis, J., Clin Invest., 2002, 110(12): 1765-1768.
Chaux et al., J. Immunol. 1999, 163: 2928-2936.
Conway et al., Three Differentially Expressed Survivin cDNA variants encode proteins with distinct antiapoptotic functions. Blood. 2000. 95(4): 1435-42.
Dibrino et al. J. Immunol. 1993. 151(110): 5930-5.
Encyclopedia Brittanica Online. 2004, www.search.eb.com/eb/orint?/eu=76559, two pages.
Engelhard V. Curro Opin. BioI. 1994. 6: 13-23.
Grube et al., CD8+ T cells reach to surviving antigen patients with multiple myeloma, Clin Cancer Res, 2007: 13(3), 1053-1060.
Guo et al., Nature 1992, 360; 364-6.
Harlow and Lane, Antibodies A Laboratory Manual. 1988. pp. 72-3, Cold Spring Harbor Laboratory, NY.
Karin et al., Journal Exp. Med. 1992. 180: 2227-2237.
Kuzushima; N. Hayashi, H. Kimura, T. Tsurumi : Efficient identification of HLA-A* 2402-restricted cytomegalovirus—specific C08+ T-cell epitopes by a computer algorithm and an enzyme-linked immunospot assay. Blood, Sep. 15, 2001, vol. 98, No. 6.
Marchand et al., Exp. Opinion Biol. Therapy, 2001, 1(3): 497-510.
Matthias Grube et al., Blood. 2005. 106(11), part 2, pp. 369B, abstract 3 5145.
Merck Manual. 16th Edition, Brikow, R. Ed., Rahway, NJ, Merck Research Laboratory, p. 21, 1992.
Morel et al., Immunity, 2000, 12: 107-117.
Muchmore et al. Crystal structure and mutagenic analysis of the inhibitor-of-apoptosis protein survivin. Molecular cell. 6(1): 173-82.
Nijman, H.W. et al., Eur. J. Immunol. 23:1215-19, 1993.
Ochoa-Garay et al. Mol. Immuno!. 1997.34(1): 273-81.
Offringa et al. Curro Opin. Immunol. 2000;12:576-85.
Rammensee et al. MHC Ligands and peptide Motifs. 1997. pp. 217-28 and 237-43, Springer, Landes Bioscience, USA.
Reker et al. Identification of novel survivin-derived CTL epitopes. Cancer Biol. & Therapy. 2004. 3(2): 173-9.
Reker et al. Journal of Immunotherapy. 2004. 27(6): 529-530.
Ruppert, J., R.T. Kudo, J. Sidney, H.M. Grey, A. Sette: Class I MHC-Peptide Interaction: Structural and Functional Aspects, Behring Inst. Mitt., No. 94, 48-60 (1994).
Sorensen et al. A survivin specific T-cell clone from a breast cancer patient displays universal tumor cell lysis. Cancer Biology and Therapy; 2008: vol. 7, Issue 12, 1885-1887.
Titzer et al., Vaccination of multiple myeloma patients with idiotype-pulsed dendritic cells: immunological and clinical aspects, British Journal of Haematology, 2000, 108, 805-816.
Hirohashi et al., "*An HLA-A24-restricted Cytotoxic T Lymphocyte Epitope of a Tumor-associated Protein, Survivin*," Clinical Cancer Research, Jun. 2002, vol. 8(6), pp. 1731-1739.

(56) References Cited

OTHER PUBLICATIONS

Schmidt et al., "*Survivin Is a Shared Tumor-Associated Antigen Expressed in a Broad Variety of Malignancies and Recognized by Specific Cytotoxic T-Cells*,"Biosis/Biosis Abstract, XP-002283859, PREV200300357946, Blood, Nov. 16, 2002, vol. 100(11):Abstract No. 3675.
Fortugno et al., "*Survivin Exists in Immunochemically Distinct Subcellular Pools and is Involved in Spindle Microtubule Function*," Journal of Cell Science Research Article (XP-002283857), 2002, vol. 115(3):575-585, The Company of Biologists, Ltd.
Schmidt et al., "*Survivin Is a Shared Tumor-Associated Antigen Expressed in a Broad Variety of Malignancies and Recognized by Specific Cytotoxic T-Cells*," Blood, Jul. 2003, vol. 102(2), pp. 571-576, The American Society of Hematology.
International Search Report dated Jun. 29, 2004 for International Application No. PCT/DK2004/000062.
Marchand, M. et al., "T. Tumor regressions Observed in patients with metastdtic melanoma treated with an antigenic peptide encoded by gene MACE-3 and presented by HLA-A1.," Int. .J. Cancer, 80: 219-230, 1999.
Grossman, D. et al., "Expression of the apoptosis inhibitor, survivin, in nonmelanoma skin cancer and gene targeting in a kertatinocyte cell line," Lab Invest, 79: 1121-1126, 1999.
Andersen, M. H. et al., "An assay for peptide binding to HLA-Cw*0102," Tissue Antigens, 54:185-190, 1999.
Cornelison, T. L., Human papillomavirus genotype 16 vaccines for cervical cancer prophylaxis and treatment, Curr. Opin. Oncol., 12:446-473, 2000.
Salgaller, M. L. et al., Recognition of multiple epitopes in the human melanoma antigen gplOO by peripheral blood lymphocytes stimulated in vitro with syntheitc peptides. Cancer Res., 55: 4972-4979, 1995.
Becker, J. et al., "Accumulation of identical T cells melanoma and vitiligo-like leukoderma," J. Invest. Dermatol., 113: 1033-1038, 1999.
Rohayem, J. et al., "Antibody response to the tumor-assmiated inhibitor of apotosis protein survivin in cancer patients." Cancer Res., Apr. 1, 2000:60; (7.):1815.-7., 60: 1815-1817.
Islam, A., et al., "High expression of Survivin, mapped to 17q25, is significantly associated with poor prognostic factors arid promotes cell survival an human neuroblastoma," Oncogene, 19:617-623, 2000.
Schrama, D. et al., "Oligoclonal I-Cell Receptor Usage of Melanocyte Differentiation Antigen-reactive 1 Cells in Stage IV Melanoma Patients," Cancer Res., 61: 493-496, 2001.
Scheibenbogen, C. et al., "A sensitive ELISPOT assay for detection of CD8+T lymphocytes specific for HLA class I-binding peptide epitopes derived *from* infuenza proteins in the blood of healthy donors and melanoma patients," Clin. Cancer Res., 3: 221-226, 1997.
de Vries, T. 3., Fourkour, A., Wobbes, I., Verkroost, G., Ruiter, D. and van Muijen, C. N. Heterogeneous expression of immunotherapy candidate proteins gplOO, MART-I, and tyrosinase in human melanoma cell lines and in human melanocytic lesions, Cancer Res., 57; 3223-3229, 1997.
Jager, E. et al., "Inverse relationship of a melanocyte differentiation antigen expression in melanoma tissues and CD8+ cytotoxic-T-cell responses: evidence for immunoselection of antigen-loss variants in vivo," Int. J. Cancer, 66: 470-476, 1996.
Cormier, J. N. et al., "Comparative analysis of the in vivo expression of tyrosinase, MART-l/Melan-A, and gplOO in metastatic melanoma lesions: implications for immunotherapy," J. Immunother., 21: 27-31, 1998.
Tamm, I., et al., "IAP-family protein survivin inhibits caspase activity anal apoptosis induced by Fas (CD95), Bax, caspases, and anticancer drugs," Cancer Res., 58: 5315-5320, 1998.
Renkvist, N. et al., "A listing of human tumor antigens recognize by T cells," Cancer Immunol Immunother., 50: 3-15, 2001.
Granziero, L. et al., "Survivin is espressed on CD4O stimulation and interfaces proliferation and apoptosis in B-cell chronic lymphocytic keukemia," Blood, 97: 2777-2783, 2001.
Andersen, N. H. et al., "Spontaneous cytoxic I-cell responses against survivin-derived MHV class I-restricted T-cell epitopes in situ as well as ex vivo in cancer patients," Cancer Res, 61: 5964-5968, 2001.
Ruppert, J., Sidney, J., Celis, F., Kubo, R. 1, Grey, H. N., and Sette: A., "Prominent role of secondary anchor residues in peptide binding to HLA-A2.1 molecules," Cell, 74: 929-937, 1993.
Rammensee, H., Bachmann, J., Emmerich, N. P., Bachor, 0. A., and Stevanovic, S., "SYFPEITHI: database for MHC ligands and peptide motifs," Immunogenetics, 50: 213-219, 1999.
Schrama, D., Pedersen Ls. L. O., Keikavoussi, P., Andersen, N. H., Straten, P. P., Brocker, E. B., Kampgen, F., and Brocker, E. C., "Aggregation of antigen-specific I cells at the inoculation site of mature dendritic cells," Invest Dermatol 119: 1443-1448, 2002.
Guichard, C., Zerbib, A., Le Gal, F. A., Hoebeke, J., Connan, F., Choppin, J., Briand, J.P., and Guillet, J. G., "Melanoma peptide MART-1(27-35) analogues with enhanced binding capacity to the human class I histocompatibility molecule HLA-A2 by introduction of a beta-amino acid residue: implications for recognition by tumor-infiltrating lymphocyes," J. Med. Chem., 43:3803-3808, 2000.
Melief, C. J., van der Burg, S. H., Toes, R. E., Ossendorp, F., and Offfinga, R., Effective therapeutic anticancer vaccines based on precision guiding of cytolytic T lymphocytes. Immunol. Rev., 188: 177-182, 2002.
Yee, C., Thompson, J. A., Roche, P., Byrd, D. P., Lee, P. P., Piepkorn, N., Kenyon, K., Davis, N. N., Riddell, S. R. and Greenberg, P. D., "Melanocyte destruction after antigen-specific immunotherapy of melanoma: direct evidence oft cell-mediated vitiligo," J. Med., 192: 1637-1644, 2000.
Hirohashi Y. et al., Biotherapy, 2001, vol. 15, No. 3, pp. 209-211, (partial English translaton,1 page).
Advisory Action in U.S. Appl. No. 10/715,417, dated Jun. 12, 2008.
Advisory Action in U.S. Appl. No. 10/715,417 dated Mar. 1, 2010.
Requirement Restriction in U.S. Appl. No. 10/715,417, dated Oct. 10, 2006.
Requirement Restriction in U.S. Appl. No. 10/354,090, dated Dec. 21, 2005.
Ambrosini et al., "Induction of Apoptosis and Inhibition of Cell Proliferation by Survivin Gene Targeting," The Joutnal of Biological Chemistry, vol. 273, No. 18, Issue of May 1, pp. 11177-11182 (1998).
Final Office Action dated Dec. 28, 2009 in co-pending U.S. Appl. No. 10/715,417.
International Preliminary Report on Patentibitity in International Application No. PCT/DK2004/000062, completed Feb. 24, 2005.
Lu, "cFos is Critical for MCF-7 breast Cancer Cell Growth", Oncogene, vol. 24, pp. 6514-6524, (2005).
Non-Final Office Action dated Feb. 17, 2009 in co-pending U.S. Appl. No. 10/715,417.
Blok, Vanessa T.; Daha, Mohamed R.; Tijsma, Odette; Harris, Claire L. Morgan, B. Paul, Fleuren, Gert Jan, Gorter, Arko : A Bispecfic Monoclonal Antibody Directed Against Both the Membrane-Bound Complement Regulator CD55 and the Renal Tumor-Associated Antigen G250 Enhances C3 Deposition and Tumor Cell Lysis by Complement. The journal of Immunology, 1998, 160: 3437-3443.
Campoli et al., Vaccine. 2002:20,A40-45.
Database: EMBL. Baculoviral IAP repeat-containing protein 5 (apoptosis inhibitor survivin) (apoptosis inhibitor 4) (TIAP) May 30, 2000. XP00392545, retrieved from EBI, Database accession No. 070201.
Engelhard V. Current Opinion in Immunology, 1994, 6: 13-23.
Grube et al, CD8+ T cells reactive to survivin antigen patients with multiple myeloma, Clin Cancer Res, 2007: 13(3), 1053-1060.
Karin et al., Journal Exp. Med. Dec. 1994, 180: 2227-2237.
Ochoa-Garay et al. Mol. Immunol, 1997,34(1): 273-81.
Ruppert, J., R.T. Kudo, J. Sidney, H.M. Grey, A. Sette, Class I MHC-Peptide Interaction; Structural and Functional Aspects, Behring Inst. Mitt., No. 94, 48-6 (1994).
Van den Eynde & Morel (2001) *Cur. Opin. Immunol.* 13: 147-153.

(56) References Cited

OTHER PUBLICATIONS

Van den Eynde, B. J. and Boon, "T. Tumor Antigens recognized by T lymphocytes", Int J. Clin. Lab. Res., vol. 27, p. 81-86, 1997.
Rosenberg, S. A., "Development of Cancer Immunotherapies based on identification of the genes encoding cancer Regression Antigens", J. Natl. Cancer Inst., vol. 20, No. 88, p. 1635-1644, 1996.
Marchand, M. et al., "T. Tumor Regressions observed in patients with metastatic melanoma treated with an antigenic peptide encoded by gene MAGE-3 and presented by HLA-A1.," Int. J. Cancer, vol. 80, p. 219-230, 1999.
Vonderheide, R. H. et al., "The Telomerase catalytic subunit is a widely expressed tumor-associated antigen recognized by cytotoxic T lymphocytes", Immunity, vol. 10, p. 673-679, 1999.
Lacasse, E. C. et al., "The inhibitors of apoptosis (IAPs) and their emerging role in cancer", Oncogene, vol. 17, p. 3247-3259, 1998.
Pardoll, D. M., "Cancer vaccines,"Nat. Med., 4:525-531, 1998.
Becker, J. C. et al., "Accumulation of identical T cells in melanoma and vitiligo-like leukoderma," J. Invest. Dermatol., 113: 1033-1038, 1999.
de Vries, T. J., Fourkour, A., Wobbes, I., Verkroost, G., Ruiter, D. 3., and van Muijen, C. N. "Heterogeneous expression of immunotherapy candidate proteins gp100, MART-1, and tyrosinase in human melanoma cell lines and in human melanocytic lesions," Cancer Res., 57: 3223-3229, 1997.
Andersen, M. H. et al., "Spontaneous cytotoxic 1-cell responses against survivin-derived MHC class I-restricted T-cell epitopes in situ as well as ex vivo in cancer patients," Cancer Res, 61: 5964-5968, 2001.
Schrama, D., Pedersen Ls, L. O., Keikavoussi, P., Andersen, M. H., Straten, P. P., Brocker, E. B., Kampgen, F., and Brocker, E. C., "Aggregation of antigen-specific I cells at the inoculation site of mature dendritic cells," J. Invest. Dermatol., 119: 1443-1448, 2002.
Hicklin, D. J., Marincola, F. M., and Ferrone, S. "HLA class I antigen downregrulation in human cancers: T-cell immunotherapy revives an old story," Mol. Med. Today, 5: 178-186, 1999.
Parkhurst, M. R., Salgaller, M. L., Southwood, S., Robbins, P. F., Sette, A., Rosenberg, S. A., and Kawakami, Y., "Improved induction of melanoma-reactive CTL with peptides from the melanoma antigen gp100 modified at HLA-A*0201-binding residues," J. Immunol. 157: 2539-2548, 1996.
Yee, C., Thompson, J. A., Roche, P., Byrd, D. R., Lee P. P. Piepkorn, M., Kenyon, K., Davis, M. M., Riddell, S. R., and Greenberg, P. D., "Melanocyte destruction after antigen-specific immunotherapy of melanoma: direct evidence of t cell-mediated vitiligo," J. Exp. Med., 192: 1637-1644, 2000.
Ambrosini, et al., (1998) *J. Biol. Chem.* 273: 11177-11182.
Ambrosini, et al. (1998) *The Journal of Biological Chemistry* 273(18); 11177-11182.
Berger et al., (2004) *Int. J. Cancer* 111: 229-237.
Bergmann, et al. (1994) *J. Virol.* 68(8): 5306-5310.
Bodey, et al., (2000) *Anticancer Research* 20: 2665-2676.
Boon, et al. (2006) *Ann. Rev. Immunol.* 24:174-208.
Blok, Vanessa T.; Daha, Mohamed R.; Tijsma, Odette; Harris, Claire L., Morgan, B. Paul, Fleuren, Gert Jan, Gorter, Arko : A Bispecific Monoclonal Antibody Directed Against Both the Membrane-Bound Complement Regulator CD55 and the Renal Tumor-Associated Antigen G250 Enhances C3 Deposition and Tumor Cell Lysis by Complement. The Journal of Immunology, 1998, 160; 3437-3443.
Campoli, et al., (2002) *Vaccine* 20: A40-45.
Celis, et al. (1994) *Mol Immunol.* 31(18): 1423-30.
Celis, et al. (2002) *J. Clin. Invest.* 110(12): 1765-1768.
Chaux, et al. (1999) *J. Immunol.* 163: 2928-2936.
Conway, et al. (2000) *Blood* 95(4): 1435-42.
Database EMBL. Baculoviral IAP repeat-containing protein 5 (apoptosis inhibitor survivin) (apoptosis inhibitor 4) (TIAP) 0May 30, 2000. XP002392545, retrieved from EBI, Database accession No. 070201.
Dibrino, et al. (1993) *J. Immunol.* 151(110); 5930-5.
Encyclopedia Britannica Online (www.search.eb.com/eb/print?eu=76559) [2004].
Eisenlhor, et al. (1992) *J. Exp. Med.* 175: 481-487.
Emens (2004) *Cancer Biol. & Therapy* 3(2) 180-183.
Engelhard (2004) *Current Opinion in Immunology* 6:13-23.
Gao, et al. (2000) *J. Immunother.* 23: 643-653.
Grube, et al. (2007) *Clin Cancer Res* 13(3): 1053-1060.
Grube, et al. (2005) *Blood* 106(11), part 2, pp. 369B, abstract 3 5145.
Guo, el al. (1992) Nature 360: 364-6.
Harlow and Lane, Antibodies A Laboratory Manual. 1988. pp. 72-73, Cold Spring Harbor Laboratory, NY.
Karin, et al. (1994) *Journal Exp. Med.* 180: 2227-2237.
Hirohashi, et al. (2001) *Biotherapy* 15(3): 209-211.
Lu (2005) *Oncogene* 24: 6516-6524.
Marchland, et al. (2001) *Exp. Opin. Bio. Ther.* 1(3): 497-510.
The Merck Manual 16$^{th}$ Edition (1992) Merck Research Laboratories, Rahway, NJ., Berkow, et al. Eds.
Morel, et al (2000) *Immunity* 12: 107-117.
Muchmore (2000) *Molecular Cell.* 6: 173-182.
Nijman, et al. (1993) *Eur. J. Immunol.*,23. 1215-19.
Offringa, et al. (2000) *Current Opin. Immunol.* 12: 576-85.
Perkins, et al. (1991) *J. Immunol.* 146(7): 2137-2144.
Rammensee, et al. MHC Ligands and peptide Motifs, 1997. pp. 217-228 and 237-243, Springer, Landes Bioscience, USA.
Reker, et al. (2004) *Cancer Biol. & Therapy.* 3(2): 173-9.
Reker, et al. (2004) *Journal of Immunotherapy* 27(6); S29-S30.
Shastri, et al. (1995) *J. Immunol.* 155: 4339-4346.
Sorensen, et al. (2008) *Cancer Biology and Therapy* 7(12): 1885-1887.
Theobald, et al. (1998) *J. Exp. Med.* 188(6): 1017-1028.
Titzer, et al. (2000) *British Journal of Haematology* 108: 805-816.
Van de Eynde & Morel (2001) *Cur. Opin. Immunol.* 13: 147-153.
Wang, et al. (1992) *Cell. Immunol.* 143(2): 284-297.
Marchand, M. et al., "T. Tumor Regressions obserbved in patients with metastdtic melanoma treated with an antigenic peptide encoded by gene MACE-3 and presented by HLA-A1.," Int. J. Cancer, vol. 80, p. 219-230, 1999.
Brossart, P. et al., "W. Her-2/neu-derived peptides are tumor-associated antigens expressed by human renal cell and colon carcinoma lines and are recognized by in vitro induced specific cytotoxic T lymphocytes", Cancer Res., vol. 58, p. 732-736, 1998.
Brossart, P. et al., "Identification of HLA-A2-restricted T-cell epitopes derived from the MUC1 tumor antigen for broadly applicable vaccine therapies", Blood, vol. 93, p. 4309-4317, 1999.
Vonderheide, R. et al., "The Telomerase catalytic subunit is a widely express tumor-associated antigen recognized by cytotoxic T lymphocytes", Immunity, vol. 10, pp. 673-679, 1999.
Lacasse, E. C. et al., "The inhibitors of apoptosis (IAPs) and their emerging role in cancer", Oncogene, vol. 17, pp. 3247-3259, 1998.
Cornelison, T. L., Human papillomavirus genotype 16 vaccines or cervical cancer prophylaxis and treatment, Curr. Opin. Oncol., 12:466-473, 2000.
Valmori, D. et al., Enhanced generation of specific tumor-ractive CTL in vitro by selected Melan-A/MART-1 immunodominant peptide analogues. J. Immunol., 160: 1750-1758, 1998.
Rohayem, J. et al., "Antibody response to the tumor-associated inhibitor of apoptosis protein survivin in cancer patients," Cancer Res., Apr. 2000, 1:60; (7.):1815.-7., 60: 1815-1817.
Islam, A. et al., "High expression of Survivin, mapped to 17q25, is significantly associated with poor prognostic factors and promotes cell survival in human neuroblastoma," Oncogene, 19:617-623, 2000.
Lee, K. H. et al., "Functional dissociation between local and systemic immune response during anti-melanoma peptide vaccination," Immunol., 161: 4183-4194, 1998.
Altman, J. D. et al., "Phenotypic analysis of antigen-specific T lymphocytes,"0 Science, 274: 94-96, 1996.
de Vries, T. 3., Fourkour, A., Wobbes, I., Verkroost, G., Rutter, D. 3., and van Muijen, C. N. Heterogeneous expression of immunotherapy candidate proteins gplOO MART-I, and tyrosinase in human melanoma cell lines and in human melanocytic lesions, Cancer Res., 57: 3223-3229, 1997.
Maeurer, N. J., "Tumor escape from immune recognition: lethal recurrent melanoma in a patient associated with downregulation of

(56) References Cited

OTHER PUBLICATIONS the peptide transporter protein TAP-1 and loss of expression of the immunodominant MART-1/Melan-A antigen," 1 Clin. Invest, 98: 1633-1641, 1996.
Tamm, I. et al., "1AP-family protein survivin inhibits caspase activity and apoptosis induced by Fas (CD95), Bax, caspases, and anticancer drugs," Cancer Res., 58: 5315-5320, 1998.
Nakagawara, A., "Molecular basis of spontaneous regression neuroblastoma: role of neurotrophic signals and genetic abnormalities," Hum. Cell, 115-124, 1998.
Gilboa, E., "The makings of a tumor rejection antigen.," Immuniity., 11: 263-270, 1999.
Altieri, D. C. et al., "Validating survivin as a cancer therapeutic target," Nat. Rev. Cancer, 3: 46-54, 2003.Olie, R. A. et al., "A novel antisense oligonucleotide targeting survivin expression induces apoptosis and sensitizes Jung cancer cells to chemotherapy," Cancer Res, 60: 2805-2809, 2000.
Ruppert, J., Sidney, J., Celis, F., Kubo, R. I, Grey, H. N., and Sette, A., "Prominent role of secondary anchor residues in peptide binding To HLA-A2.1 molecules," Cell, 74: 929-937, 1993.
Rammensee, H., Bachmann, J., Emmerich, N. P., Bachor, 0, A., and Stevanovie, S., "SYFPEITHI: database for MHC ligands and peptide motifs," Immunogenetics, 50: 213-219, 1999.
Parkhurst, M. R., Salgaller, N. L., Southwood, S., Robbins, P. F., Sette, A., Rosenberg, S. A., and Kawakami, Y., "Improved induction of melanoma-reactive CTL with peptides from the melanoma antigen gplOO modified at HLA-A*0201-binding residues," J. Immunal 157: 2539-2548, 1996.
Simon, R. M., Steinberg, S. M., Hamilton, M., Hildesheim, A., Khleif, S., Kwak, L. W., Mackall, C. L., Schlom, J., Topalian, S. L., and Berzolsky, J. A., "Clinical trial designs for the early clinical development of therapeutic cancer vaccines," J. Clin. Oncol., 19: 1848-1854, 2001.
Andersen et al (Cancer Res. 2001, 61: 869-872).
Andersen, Mads Hald, "HLA-A24 and survivin: possibilities in therapeutic vaccination against cancer" Journal of Translation Medicine 2006, 4:38 (pp. 1-4).
Fournier and Schirrmacher (Expert. Rev. Vaccines 8(1); 51-66, 2009).*
Schrieber et al (Seminar. Immunol. 22: 105-112, 2010).*
Klebanoff et al (Immunol. Rev. 2011, 239: 27-44).*
Petersen et al (J. Mol. Med. 2009, 87: 1045-1051).*
Campbell, Monoclonal Antibody Technology. 1884. pp. 1-32, Elsevier Sciences Publishers, Amsterdam.
Gileadi, et al. (1999) *Eur. J. Immunol.* 29: 2213-2222.
Schmitz, et al. (2000) *Cancer Research* 60: 4845-4849.
Van der Eynde, B. J. et al., "Tumor Antigens recognized by T lymphocytes", Int. J. Clin. Lab. Res., vol. 27, p. 81-86, 1997.
Rosenberg, S. A., "Development of Cancer Immunotherapies based on identification of the genes encoding cancer Regression Antigens", J. Natl. Cancer Inst., vol. 22, No. 88, p. 1635-1644, 1996.
Altieri, D. C. et al., "Survivin apoptosis:an interloper between cell death and cell proliferation in cancer",Lab Invest, 79:1327-1333, 1999.
Ambrosini, G. et al., "Induction of apoptosis and inhibition of cell proliferation by survivin, in human melanoma," J. Invest Dermatol., 113:1076-1081, 1999.
Grossman, D. et al., "Expression and targeting of the apoptosis inhibitor, survivin, in human melanoma," J. .Invest Dermatol., 113: 1076-1081, 1999.
Andersen, M. H. et al., Phosphorylated Peptides Can Be Transported by TAP Molecules, Presented by Class I MHC Molecules, and Recognized by Phosphopeptide-Specific CTL. J. Immunol., 163:3812-3188, 1999.
McCutcheon, M. et al., "A sensitive ELISPOT assay to detect low-frequency human T lymphocytes," J. Immunol. Methods, 210:149-166, 1997.
Pass, H. A. et al., "Immunization of patients with melanoma peptide vaccines: immunologic assessment using the ELISPOT assay," Cancer J. Sci. Am., 4: 316-323, 1998.
Berke, Z. et al., "Peptides spanning the junctional region of both the abl/bcr and the bcr/abl fusion proteins bind common HLA class I molecules," Leukemia, 14:419-426, 2000.
Falk, K.et al., "Allele-specific motifs revealed by sequencing of self-peptides eluted from MHC molecules," Nature, 351:290-296, 1991.
Lee, S. P. et al., "CTL control of EVB in nasopharyugeal carcinoma (NPC): EBV-specific CTL responses in the blood and tumors of NPC patients and the antigen-processing function of the tumor cells," Immunol., 165: 573-582, 2000.
Swana, H. S. et al., Tumor content of the antiapoptosis molecule survivin and recurrence of bladder cancer. N. Engl. J. Med., 341: 452-453, 1999.
Salgaller, H. L. et. al., "Immunization against epitopes in the human melanoma antigen gplOO following patient immunization with synthetic peptide," Cancer Res., 56:4749-4757, 1996.
Valmori, D. et al., Enhanced generation of specific tumor-reactive CTL in vitro by selected Melan-A/MART-1 immunodominant peptide analogues. J. Immunol., 160: 1750-1758, 1998.
Kugler, A. et al., "Regression of human metastatic renal cell carcinoma after vaccination with tumor cell-dendritic cell hybrids," Nat. Med., 6:332-336, 2000.
Adida, C. et al., "Prognostic significance of survivin expression in diffuse large B-cell lymphomas," Blood, 96: 1921-1925, 2000.
Kawasaki, H., "Inhibition of apoptosis by survivin predicts shorter survival rates in colorectal cancer," Cancer Res., 58:5071-5074, 1998.
Schmitz, M. et al., "Generation of survivin-specific CD8+ T effector cells by dendritic cells pulsed with protein or selected peptides," Cancer Res., 60:4845-4849, 2000.
Andersen, M. H. et al., "Identification of a Cytotoxic T Lymphocyte Response to the Apoptosis inhibitor Protein Survivin in Cancer Patients," Cancer Res., 61:869-872, 2001.
Rosenberg, S. A. et al., "Immunologic and therapeutic evaluation of a synthetic peptide vaccine for the treatment of patients with metastatic melanoma," Nat. Med., 4: 321-327, 1998.
Luxembourg, A. T. et al., "Biomagnetic isolation of antigen-specific CCD8+ T cells usable in immunotherapy," Nat. Biotechnol., 16: 281-285, 1998.
Kirkin, A. F. et al., "Generation of human-melanoma specific T lymphocyte clones defining novel cytolytic targets with panels of newly established melanoma cell lines," Cancer Immunol. Immunother., 41: 71-81, 1995.
thor Straten, P. et al., "In Situ I-Cell Responses against Melanoma Comprise High Numbers of Locally Expanded I-Cell Clonotypes," J. .Immunol., 163: 443-447, 1999.
Kessler, J. H. et al., "Efficient identification of novel HLA-A(*)0201-presented cytotoxic T lymphocyte epitopes in the widely expressed tumor antigen PRAME by proteasome-mediated digestion analysis.," J. Exp. Med., 193: 73-88, 2001.
Riker, A. et al., "Immune selection after antigen-specific immunotherapy of melanoma," Surgery, 126: 112-120, 1999.
Grossman, D. et al., "Inhibition of melanoma tumor growth in vivo by survivin targeting.," Proc. Natl. Acad. Sci. USA, 98: 635-640, 2001.
Monzo, M. et al., "A novel anti-apoptosis gene: Re-expression of survivin messenger RNA as a prognosis marker in non-small-cell lung cancers," J. Clin. Oncol., 17: 2100-2104, 1999.
Melief, C. J. et al., "Strategies for immunotherapy of cancer," Adv. Immunol., 75:235-82.: 235-282, 2000.
Li, F. et al., "Control of apoptosis and mitotic spindle checkpoint by survivin," Nature, 396: 580-584, 1998.
Zaffaroni, N. et al., "Survivin expression and resistance to anticancer treatments: perspectives for new therapeutic interventions," Drug Resist. Updat., 5: 65-72, 2002.
Ambrosini, C. et al., "A novel anti-apoptosis gene, survivin, expressed in cancer and lymphoma," Nat. Med., 3: 917-921, 1997.
Andersen, N. H. et al., "Survivin--a universal tumor antigen," Histol. Histopathol., 17: 669-675, 2002.
Currier, J. R. et al., "A panel of MHC class I restricted viral peptides for use as a quality control for vaccine trial ELISPOT assays," J. .Immunol. Methods, 260: 157-172, 2002.

(56) References Cited

OTHER PUBLICATIONS thor Straten, P., Barbed, A., Seremet, I., Saeterdal, I., Zeuthen, 3., and Guldberg, P. Detection and characterization of alpha-beta-T-cell clonality by denaturing gradient gel electrophoresis (DCGE)., Biotechniques, 25: 244-250,1998.

Mahotka, C., Wenzel, N., Springer, F., Gabbert, H. E., and Gerharz, C. D., "Survivin-deltaEx3 and survivin-2B: two novel splice variants of the apoptosis inhibitor survivin with different antiapoptotic properties," Cancer Res., 59: 6097-6102, 1999.

Seliger, B., Cabrera, T., Garrido, F., and Ferrone, S. HLA class I antigen abnormalities and immune escape by malignant cells, Semin. Cancer Biol., 12: 3-13, 2002.

Moudgil, K. D. and Sercarz, E. E., "Can antitumor immune responses discriminate between self and nonself?," Immunol. Today, 15: 353-355, 1994.

Jager, E., Ringhoffer, M., Altmannsberger, M., Arand, M., Karbach, J., Jager, D., Oesch, F., and Knuth, A., "Immunoselection in vivo: independent loss of MHC class I and melanocyte differentiation antigen expression in metastatic melanoma," Int. J. Cancer, 71: 142-147, 1997.

Thurner, B., Haendle, I., Roder, C., Dieckmann, D., Keikavoussi, P., Jonuleit, H., Bender, A., Maczek, C., Schreiner, D., von den, D. P., Brocker, E. B., Steinman, R. M., Enk, A., Kampgen, E., and Schuler, G., "Vaccination with mage3A1 peptide-pulsed mature, monocyte-derived dendritic cells expands specific cytotoxic T cells and induces regression of some metastases in advanced stage IV melanoma.," J. Exp. Med., 190: 1669-1678, 1999.

Olie, R. A. et al., "A novel antisense oligonucleotide targeting survivin expression induces apoptosis and sensitizes lung cancer cells to chemotherapy," Cancer Res, 60: 2805-2809, 2000.

Salgaller, M. L. et al., "Recognition of multiple epitopes in the human melanoma antigen gp100 by peripheral blood lymphocytes stimulated in vitro with synthetic peptides." Cancer Res., 55: 4972-4979, 1995.

Salgaller, M. L. et al., "Immunization against epitopes in the human melanoma antigen gp100 following patient immunization with synthetic peptide," Cancer Res., 56:4749-4757, 1996.

Cormier, J. N. et al., "Comparative analysis of the in vivo expression of tyrosinase, MART-1/Melan-A, and gp100 in metastatic melanoma lesions: implications for immunotherapy," J. Immunother., 21: 27-31, 1998.

Altieri, D. C. et al., "Validating survivin as a cancer therapeutic target," Nat. Rev. Cancer, 3: 46-54, 2003.

Andersen, M. H. et al., "Survivin--a universal tumor antigen," Histol. Histopathol., 17: 669-675, 2002.

Sette, A., Vitiello, A., Reherman, B., Fowler, P., Nayersina, R., Kast, W. M., Melief, C. J., Oseroff, C., Yuan, L., Ruppert, J. et al., "The relationship between class I binding affinity and immunogenicity of potential cytotoxic T cell epitopes," J. Immunol., 153: 5586-5592, 1994.

Guichard, G., Zerbib, A., Le Gal, F. A., Hoebeke, J., Connan, F., Choppin, J., Briand, J. P., and Guillet, J. G., "Melanoma peptide MART-1(27-35) analogues with enhanced binding capacity to the human class I histocompatibility molecule HLA-A2 by introduction of a beta-amino acid residue: implications for recognition by tumor-infiltrating lymphocytes," J. Med. Chem., 43: 3803-3808, 2000.

Clay, T. M., Custer, M. C., McKee, M. D., Parkhurst, M., Robbins, P. F., Kerstann, K., Wunderlich, J., Rosenberg, S. A., and Nishimura, M. I., "Changes in the fine specificity of gp100(209-217)-reactive T cells in patients following vaccination with a peptide modified at an HLA-A2.1 anchor residue," J. Immunol., 162: 1749-1755, 1999.

* cited by examiner

SURVIVIN-DERIVED PEPTIDES AND USES THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application *is a reissue application of U.S. Pat. No. 9,534,030, issued on Jan. 3, 2017, which* is a divisional patent application of U.S. patent application Ser. No. 10/543,755 filed Jun. 1, 2006, now U.S. Pat. No. 8,318,174, which is a 371 national stage filing of PCT/DK2004/000062, filed Jan. 30, 2004, which is a continuation of U.S. patent application Ser. No. 10/354,090, filed Jan. 30, [2004] *2003*, now abandoned, and which is also a continuation of U.S. patent application Ser. No. 10/715,417, filed Nov. 19, 2003, now U.S. Pat. No. 7,892,559, which is a continuation-in-part of U.S. application Ser. No. 10/354,090, filed Jan. 30, 2003, now abandoned, which claims priority to U.S. Provisional Patent Application No. 60/352,284, filed Jan. 30, 2002, the disclosures of each of which are hereby incorporated by reference.

*SEQUENCE LISTING*

*This application contains a Sequence Listing which has been submitted in ASCII format via EFS-Web and is hereby incorporated by reference herein in its entirety. The ASCII text file created on Sep. 19, 2018, is named SequenceListing.txt and is 17,706 bytes in size.*

FIELD OF INVENTION

The present invention relates to novel survivin-derived peptides and their use for diagnostic and therapeutic purposes, specifically in cancer. In particular, the novel peptides are MHC Class I-restricted T-cell epitopes that are capable of eliciting cytotoxic T-cell responses in cancer patients including in situ and ex vivo responses. Specifically, such novel peptides are derived from the apoptosis inhibitor protein survivin, a recognized tumor associated antigen (TAA).

TECHNICAL BACKGROUND AND PRIOR ART

The process by which the mammalian immune system recognizes and reacts to foreign or alien materials is a complex one. An important facet of the system is the T-cell response. This response requires that T cells recognize and interact with complexes of cell surface molecules referred to as human leukocyte antigens (HLA) constituting the human major histocompatibility complex (MHC), and peptides. The peptides are derived from larger molecules, which are processed by the cells, which also present the HLA/MHC molecule. The interaction of T cells and complexes of HLA/peptide is restricted, requiring a T cell that is specific for a particular combination of an HLA molecule and a peptide. If a specific T cell is not present, there is no T-cell response even if its partner complex is present. Similarly, there is no response if the specific complex is absent, but the T cell is present.

The mechanism by which T cells recognize cellular abnormalities has also been implicated in cancer. E.g. in WO92/20356, a family of genes is disclosed which are processed into peptides which, in turn, are expressed on cells surfaces, and can lead to lysis of the tumour cells by specific CTLs. These genes are referred to as the MAGE family and are said to code for "tumour rejection antigen precursors" or "TRAP" molecules, and the peptides derived therefrom are referred to as "tumour rejection antigens" or "TRAs".

In WO 94/05304, nonapeptides are disclosed which bind to the HLA-A1 molecule. The reference discloses that given the known specificity of particular peptides for particular HLA molecules, one should expect a particular peptide to bind one HLA molecule, but not others. This is significant, because different individuals possess different HLA phenotypes. As a result, while identification of a particular peptide as being a partner for a specific HLA molecule has diagnostic and therapeutic ramifications, these are only relevant for individuals with that particular HLA phenotype.

Several peptides presented by MHC molecules have been characterized and it has been found that some of these may carry posttranslational modifications possibly having an impact on the functionality of the HLA-peptide complex. Thus, a number of studies have associated alterations in the pattern of phosphorylation with malignant transformation. Furthermore, it has been shown that phosphorylation could have a neutral, negative or even a positive effect on peptide binding to class I MHC and that phosphopeptide-specific CTL, which discriminated between the phosphorylated and the non-phosphorylated versions of the peptide, could be generated, showing that such CTL most likely are part of the class I MHC-restricted CTL repertoire. Recently, it has been shown that phosphorylated peptides indeed are processed naturally and presented by MHC class I molecules in vivo. Additionally, the presence of phosphorylated peptides in extracts from isolated class I molecules from several different EBV-transformed B-cells has been established.

Thus, it is well established that peptide epitopes derived from tumor associated antigens (TAAs) can be recognized as antigens by cytotoxic T lymphocytes (CTLs) in the context of MHC molecules (1). However, although it is generally accepted that most if not all, tumours are antigenic, only a few are indeed immunogenic in the sense that tumour progression is readily controlled by the immune system.

To overcome this limitation, several immunotherapeutic trials have been initiated, e.g. vaccinations with TAA-derived peptides. For melanoma, the tumour for which the largest number of CTL-defined TAAs has been characterized, powerful CTL responses against antigens have been induced by vaccination and some patients experienced a complete remission of their disease (2,3). However, most of the peptide epitopes used in these vaccination trials are melanocyte specific, and these peptides cannot be applied for tumours of non-melanocyte origin. Furthermore, expression of these TAAs is heterogeneous among tumours from different patients and can even vary among metastases obtained from one patient. However, during the last couple of years a number of tumour specific peptide antigens, which are expressed in a number of different cancers, have been identified, i.e. HER-2 (4), Muc-1 (5) and telomerase (6).

It has also been shown that by proper manipulation tumor antigens present in tumors can be exposed to the immune system. Studies have shown that the CD8+ CTL arm of the immune response, alone or in combination with CD4+ $T_h$ cells, constitutes the primary anti-tumor effector arm of the adaptive immune response. Up till now the focus has mainly been on the CTL arm of the immune response. However, it is becoming more and more clear that the CD4 T cell response plays an essential role in tumor rejection, especially in the induction phase or in the extension of a CTL response in vivo. Consequently, the incorporation of class II-restricted tumor antigens into effective tumor vaccination protocols might increase the effectiveness of the vaccines.

Apoptosis is a genetic program of cellular suicide, and Inhibition of apoptosis has been suggested to be an important mechanism involved in cancer formation by extending the life span of cells favouring the accumulation of transforming mutations (7). Survivin is a recently identified member of the family of inhibitors of apoptosis proteins (IAPs). In a global gene expression analysis of about 4 million transcripts, survivin was identified as one of the top genes invariably up-regulated in many types of cancer but not in normal tissue (8). Solid malignancies overexpressing survivin include lung, colon, breast, pancreas, and prostate cancer as well as hematopoietic malignancies (9). Additionally, series of melanoma and non-melanoma skin cancers have been reported to be invariably survivin positive (10, 11). The overexpression of survivin in most human cancers suggests a general role of apoptosis inhibition in tumor progression, a notion substantiated by the observation that in the case of colorectal and bladder cancer, as well as neuroblastoma, expression of survivin was associated with an unfavourable prognosis. In contrast, survivin is undetectable in normal adult tissues. These characteristics qualify survivin as a suitable TAA for both diagnostic and therapeutic purposes.

Thus, during the last decade a large number of TAAs have been identified which are recognized by CTLs in a major histocompatibility complex (MHC)-restricted fashion. As survivin is overexpressed in most human cancers and inhibition of its function results in increased apoptosis, this protein may serve as a target for therapeutic CTL responses. The survivin protein and the potential diagnostic and therapeutic use hereof are disclosed in (8) and U.S. Pat. No. 6,245,523, which are incorporated herein by reference. Survivin is a 16.5 kDa cytoplasmic protein containing a single BIR and a highly charged carboxy-terminal coiled region instead of a RING finger, which inhibits apoptosis induced by growth factor (IL-3) withdrawal when transferred in B cell precursors. The gene coding for survivin is nearly identical to the sequence of Effector Cell Protease Receptor-1 (EPR-1), but oriented in the opposite direction, thus suggesting the existence of two separate genes duplicated in a head-to-head configuration. Accordingly, survivin can be described as an antisense EPR-1 product. Functionally, inhibition of survivin expression by up-regulating its natural antisense EPR-1 transcript results in massive apoptosis and decreased cell growth.

U.S. Pat. No. 6,245,523 discloses the isolation of purified survivin and it provides nucleic acid molecules that encode the survivin protein, and antibodies and other molecules that bind to survivin. U.S. Pat. No. 6,245,523 also discloses anti-apoptotically active fragments of the survivin protein and variants hereof wherein an amino acid residue has been inserted N- or C-terminal to, or within, the disclosed survivin sequence. It is specifically disclosed that such peptides should contain key functional residues required for apoptosis, i.e. Trp at position 67, Pro at position 73 and Cys at position 84.

The present invention is based on the discovery that MHC Class I restricted peptides can be derived from the survivin protein, which are capable of binding to MHC Class I HLA molecules and thereby eliciting both ex vivo and in situ CTL immune responses in patients suffering from a wide range of cancer diseases. These findings strongly suggest that survivin acts as a TRAP molecule, which is processed by cells into peptides having TRA functionality. Evidently, these findings open the way for novel therapeutic and diagnostic approaches which, due to the fact that survivin appears to be expressed universally by tumour cells, are generally applicable in the control of cancer diseases.

SUMMARY OF THE INVENTION

Accordingly, the invention pertains in a first aspect to a MHC Class I-restricted epitope peptide derived from survivin, said epitope having at least one of the following characteristics:

(i) capable of binding to the Class I HLA molecule to which it is restricted at an affinity as measured by the amount of the peptide that is capable of half maximal recovery of the Class I HLA molecule ($C_{50}$ value) which is at the most 50 μM as determined by the assembly binding assay as described herein, (ii) capable of eliciting INF-γ-producing cells in a PBL population of a cancer patient at a frequency of at least 1 per $10^4$ PBLs as determined by an ELISPOT assay, and/or (iii) capable of in situ detection in a tumour tissue of CTLs that are reactive with the epitope peptide.

Preferably, the peptide of the invention has at least two, most preferably all of these three features.

In further aspects the invention provides a pharmaceutical composition and a composition for ex vivo or in situ diagnosis of the presence in a cancer patient of survivin reactive T-cells among PBLs or in tumour tissue, which composition comprises a peptide as defined above.

In yet further aspects the invention relates to a diagnostic kit for ex vivo or in situ diagnosis of the presence in a cancer patient of survivin reactive T-cells among PBLs or in tumor tissue, which kit comprises a peptide according of the invention, and a complex of such a peptide and a Class I HLA molecule or a fragment of such molecule.

In another aspect there is also provided a method of detecting in a cancer patient the presence of survivin reactive T-cells, the method comprising contacting a tumour tissue or a blood sample with a complex as defined above and detecting binding of the complex to the tissue or the blood cells.

In still further aspects the invention pertains to a molecule that is capable of binding specifically to a peptide of the invention such as an antibody or a fragment hereof, and to a molecule that is capable of blocking the binding of such a molecule.

An important aspect of the invention relates to the use of the peptides of the invention for the preparation of a medicament for the treatment of cancer. A further aspect relates to the use of the composition or the molecule as mentioned above for the preparation of a medicament for the treatment of cancer.

Still further aspects relate independently to a method for treating cancer in a mammal, such as a human, comprising the administration to a patient suffering from the disease an effective amount of the peptide, composition or a molecule of the invention.

DETAILED DISCLOSURE OF THE INVENTION

The novel MHC Class I-restricted peptide of the invention is characterised by having at least one of several features, one of which is the ability to bind to the Class I HLA molecule to which it is restricted at an affinity, which, when it is measured by the amount of the peptide that is capable of half maximal recovery of the Class I HLA molecule ($C_{50}$ value) in an assembly assay as described herein, is at the most 50 μM. This assembly assay is carried out as described previously (12,13), and it is based on stabilisation of the HLA molecule after loading of peptide to the peptide transporter deficient cell line T2. Subsequently, correctly folded stable HLA heavy chains are immunoprecipitated using conformation dependent antibodies and the peptide binding is quantitated.

This assay provides a simple means of screening candidate peptides for their ability to bind to a given HLA allele molecule at the above affinity. In preferred embodiments, the peptide of the invention In one having a $C_{50}$ value, which is at the most 30 μM, such as a $C_{50}$ value, which is at the most 20 μM including $C_{50}$ values of at the most 10 μM, at the most 5 μM and at the most 2 μM.

As mentioned above, the HLA system represents the human major histocompatibillty (MHC) system. Generally, MHC systems control a range of characteristics: transplantation antigens, thymus dependent immune responses, certain complement factors and predisposition for certain diseases. More specifically, the MHC codes for three different types of molecules, i.e. Class I, II and III molecules, which determine the more general characteristics of the MHC. Of these molecules, the Class I molecules are so-called HLA-A, HLA-B and HLA-C molecules that are presented on the surface of most nucleated cells and thrombocytes.

The peptides of the present invention are characterised by their ability to bind to (being restricted to) a particular MHC Class I HLA molecule. Thus, in one embodiment the peptide is one which is restricted to a MHC Class I HLA-A molecule including HLA-A1, HLA-A2, HLA-A3, HLA-A9, HLA-A10, HLA-A11, HLA-Aw19, HLA-A23(9), HLA-A24(9), HLA-A25(10), HLA-A26(10), HLA-A28, HLA-A29(w19), HLA-A30(w19), HLA-A31(w19), HLA-A32(w19), HLA-Aw33(w19), HLA-Aw34(10), HLA-Aw36, HLA-Aw43, HLA-Aw66(10), HLA-Aw68(28), HLA-A69(28). More simple designations are also used throughout the literature, where only the primary numeric designation is used, e.g. HLA-A19 or HLA-A24 instead of HLA-Aw19 and HLA-A24(9), respectively. In specific embodiments, the peptide of the invention is restricted to a MHC Class I HLA species selected from the group consisting of HLA-A1, HLA-A2, HLA-A3, HLA-A11 and HLA-A24.

The peptides of the invention are derived from the known sequence of survivin, e.g. the sequence disclosed in U.S. Pat. No. 6,245,523. The selection of peptides potentially having the ability to bind to a particular HLA molecule can be made by the alignment of known sequences that bind to a given particular HLA molecule to thereby reveal the predominance of a few related amino acids at particular positions in the peptides. Such predominant amino acid residues are also referred to herein as "anchor residues" or "anchor residue motifs". By following such a relatively simple procedure based on known sequence data that can be found in accessible databases, peptides can be derived from the survivin protein molecule which are likely to bind to the particular HLA molecule. Representative examples of such analyses for a range of HLA molecules are given in the below table:

| HLA allele | Position 1 | Position 2 | Position 3 | Position 5 | Position 6 | Position 7 | C-terminal |
|---|---|---|---|---|---|---|---|
| HLA-A1 | | T, S | D, E | | | L | Y |
| HLA-A2 | | L, M | | | V | | L, V |
| HLA-A3 | | L, V, M | F, Y | | | | K, Y, F |
| HLA-A11 | | V, I, F, Y | M, L, F, Y, I | | | | K, R |
| HLA-A23 | | I, Y | | | | | W, I |
| HLA-A24 | | Y | | I, V | F | | I, L, F |
| HLA-A25 | | M, A, T | I | | | | W |
| HLA-A26 | E, D | V, T, I, L, F | | | I, L, V | | Y, F |
| HLA-A28 | E, D | V, A, L | | | | | A, R |
| HLA-A29 | | E | | | | | Y, L |
| HLA-A30 | | Y, L, F, V | | | | | Y |
| HLA-A31 | | | L, M, F, Y | | | | R |
| HLA-A32 | | I, L | | | | | W |
| HLA-A33 | | Y, I, L, V | | | | | R |
| HLA-A34 | | V, L | | | | | R |
| HLA-A66 | E, D | T, V | | | | | R, K |
| HLA-A68 | E, D | T, V | | | | | R, K |
| HLA-A69 | | V, T, A | | | | | V, L |
| HLA-A74 | | T | | | | | V, L |
| HLA-B5 | | A, P | F, Y | | | | I, L |
| HLA-B7 | | P | | | | | L, F |
| HLA-B8 | | | K | K, R | | | L |
| HLA-B14 | | R, K | | | | | L, V |
| HLA-B15 (B62) | | Q, L, K, P, H, V, I, M, S, T | | | | | F, Y, W |
| HLA-B17 | | | | | | | L, V |
| HLA-B27 | | R | | | | | Y, K, F, L |
| HLA-B35 | | P | | | | | I, L, M, Y |
| HLA-B37 | | D, E | | | | | I, L, M |
| HLA-B38 | | H | D, E | | | | F, L |
| HLA-B39 | | R, H | | | | | L, F |
| HLA-B40 (B60,61) | | E | F, I, V | | | | L, V, A, W, M, T, R |
| HLA-B42 | | L, P | | | | | Y, L |
| HLA-B44 | | E | | | | | F, Y, W |
| HLA-B46 | | M, I, L, V | | | | | Y, F |
| HLA-B48 | | Q, K | | | | | L |
| HLA-B51 | | A, P, G | | | | | F, Y, I, V |
| HLA-B52 | | Q | F, Y | | | | I, V |
| HLA-B53 | | P | | | | | W, F, L |

-continued

| HLA allele | Position 1 | Position 2 | Position 3 | Position 5 | Position 6 | Position 7 | C-terminal |
|---|---|---|---|---|---|---|---|
| HLA-B54 | | P | | | | | |
| HLA-B55 | | P | | | | | A, V |
| HLA-B56 | | P | | | | | A, V |
| HLA-B57 | | A, T, S | | | | | F, W, Y |
| HLA-B58 | | A, T, S | | | | | F, W, Y |
| HLA-B67 | | P | | | | | L |
| HLA-B73 | | R | | | | | P |
| HLA-Cw1 | | A, L | | | | | L |
| HLA-Cw2 | | A, L | | | | | F, Y |
| HLA-Cw3 | | A, L | | | | | L, M |
| HLA-Cw4 | | Y, P, F | | | | | L, M, F, Y |
| HLA-Cw6 | | Y | | | | | L, Y, F, Y |
| HLA-Cw8 | | Y | | | | | L, I, |
| HLA-Cw16 | | A, L | | | | | L, V |

Thus, as an example, nonapeptides potentially having the ability to bind to HLA-A1 would have one of the following sequences: Xaa-T-D-Xaa-Xaa-Xaa-L-Xaa-Y, Xaa-T-E-Xaa-Xaa-Xaa-L-Xaa-Y; Xaa-S-D-Xaa-Xaa-Xaa-L-Xaa-Y or Xaa-S-E-Xaa-Xaa-Xaa-L-Xaa-Y (Xaa indicating any amino acid residue). In a similar manner, sequences potentially having the ability to bind to any other HLA molecule can be designed.

It will be appreciated that the person of ordinary skill in the art will be able to identify further "anchor residue motifs" for a given HLA molecule.

Thus, in useful embodiments, the peptides of the invention include peptides, the sequences of which comprise, for each of the specific HLA alleles listed in the table, any of the amino acid residues as indicated in the table.

Thus, a simple approach to identifying peptides of the invention includes the following steps: selecting a particular HLA molecule, e.g. one occurring at a high rate in a given population, carrying out an alignment analysis as described above to identify "anchor residue motifs" in the survivin protein, isolating or constructing peptides of a suitable size that comprise one or more of the identified anchor residues and testing the resulting peptides for (i) capability to bind to the particular HLA molecule using the assembly assay as described herein, (ii) the capability of the peptides to elicit INF-γ-producing cells in a PBL population of a cancer patient at a frequency of at least 1 per $10^4$ PBLs as determined by an ELISPOT assay as described herein, and/or (iii) the capability of the peptides to detect in situ in a tumour tissue CTLs that are reactive with the epitope peptides being tested.

In specific embodiments, the peptide of the invention is an HLA-A2 restricted survivin-derived peptide having a sequence selected from the following: FLKLDRERA (survivin$_{101-109}$) (SEQ ID NO:1), TLPPAWQPFL (survivin$_{5-14}$) (SEQ ID NO:2), ELTLGEFLKL (survivin$_{95-104}$) (SEQ ID NO:3), LLLGEFLKL (SEQ ID NO:4) and LMLGEFLKL (SEQ ID NO:5). (The designations in brackets indicate the positions of the residues in the survivin protein as disclosed in U.S. Pat. No. 6,245,523). LLLGEFLKL (SEQ ID NO:4) is a sequence derived from survivin$_{96-104}$ by substituting "T" in position 2 of the peptide with an "L" and LMLGEFLKL (SEQ ID NO:5) is derived from survivin$_{96-104}$ by substituting "T" in position 2 with "M".

In further useful embodiments, the peptide of the invention is a peptide, which is restricted by a MHC Class I HLA-B molecule including any of the following: HLA-B5, HLA-B7, HLA-B8, HLA-B12, HLA-B13, HLA-B14, HLA-B15, HLA-B16, HLA-817, HLA-B18, HLA-B21, HLA-Bw22, HLA-B27, HLA-B35, HLA-B37, HLA-B38, HLA-B39, HLA-B40, HLA-Bw41, HLA-Bw42, HLA-B44, HLA-B45, HLA-Bw46 and HLA-Bw47. In specific embodiments, the MHC Class I HLA-B species to which the peptide of the invention is capable of binding is selected from HLA-B7, HLA-B35, HLA-B44, HLA-B8, HLA-B15, HLA-B27 and HLA-B51.

In specific embodiments, the peptide of the invention is an HLA-B35-restricted survivin-derived peptide having a sequence selected from the following: CPTENEPDL (survivin$_{46-54}$) (SEQ ID NO:6), EPDLAQCFF (survivin$_{51-59}$) (SEQ ID NO:7), CPTENEPDY (SEQ ID NO:8) and EPDLAQCFY (SEQ ID NO:9). (The designations in brackets indicate the positions of the residues in the survivin protein as disclosed in U.S. Pat. No. 6,245,523). CPTENEPDY (SEQ ID NO:8) is a sequence derived from survivin$_{46-54}$ by substituting "L" in the C-terminal of the peptide with a "Y" and EPDLAQCFY (SEQ ID NO:9) is derived from survivin$_{51-59}$ by substituting an "F" residue in the C-terminal 2 with a "Y".

In further specific embodiments, the peptide of the invention is a HLA-A1 restricted peptide having a sequence selected from the following: Survivin$_{38-46}$ (Sur38Y9) (a C changed to a Y at P9, MAEAGFIHY) (SEQ ID NO:38), Survivin$_{47-56}$ (Sur47Y10) (a Q changed to a Y at P10, PTENEPDLAY (SEQ ID NO:39)), Survivin$_{92-101}$ (Sur92-101) (QFEELTLGEF) (SEQ ID NO:27), and Survivin$_{93-101}$ (Sur93T2 (a E changed to a T at P2, FTELTLGEF (SEQ ID NO:36)). The peptide of the invention may also be a HLA-A3 restricted peptide such as Survivin$_{18-27}$ (Sur18K10) (a F changed to a K at P10, RISTFKNWPK (SEQ ID NO:58) and/or a HLA-A11 restricted peptide such as Survivin$_{53-62}$ (Sur53-62) (DLAQCFFCFK) (SEQ ID NO:45) and/or a HLA-A2 restricted peptide such as Survivin$_{18-28}$ (Sur18-28) (RISTFKNWPFL) (SEQ ID NO:66).

In further useful embodiments, the peptide of the invention is a peptide, which is restricted to a MHC Class I HLA-C molecule including any of the following: HLA-Cw1, HLA-Cw2, HLA-Cw3, HLA-Cw4, HLA-Cw5, HLA-Cw6, HLA-Cw7 and HLA-Cw16.

Preferably, the peptide of the invention comprises less than 50 amino acid residues, and more preferably it comprises at the most 20 amino acid residues, such as at the most 10 amino acid residues. In specific embodiments, the peptide is a heptapeptide, an octopeptide, a nonapeptide, a decapeptide or an undecapeptide.

The peptide of the invention is, as mentioned above, derived from a survivin protein or a fragment hereof. The survivin protein from which the peptide can be derived is survivin protein from any animal species in which the protein is expressed. In preferred embodiments, the survivin starting protein is from a mammal species including a rodent species, rabbit and a primate species such as humans. Based on the sequence of the selected survivin protein, the peptide of the invention is derived by any appropriate chemical or enzymatic treatment of the survivin starting material that results in a peptide of a suitable size as indicated above, or it can be synthesised by any conventional peptide synthesis procedures with which the person of ordinary skills in the art is familiar.

The peptide of the invention may have a sequence which is a native sequence of the survivin protein from which is derived. However, peptides having a higher affinity to any given HLA molecule may be derived from such a native sequence by modifying the sequence by substituting, deleting or adding at least one amino acid residue, e.g. on the basis of the procedure described above whereby anchor residue motifs in respect of the given HLA molecule are identified.

Accordingly, to increase the immuogenicity of survivin-derived peptides, amino acid substitutions can be introduced at anchor positions, but not at TCR contact residues, to increase peptide binding to the HLA class I molecule. This has resulted in more immunogenic epitopes, e.g., this has enhanced the capacity to induce cancer-reactive CTL and it has been demonstrated to be more suitable for the induction of clinically meaningful CTL responses. Importantly, however, the target cancer cells do only express and present the native survivin-derived peptide on the cell-surface. In that respect, it is of crucial importance that therapy-induced CTL specific for the modified survivin-derived peptides cross-react with the native analogues.

The present invention also encompasses variants and functional equivalents of the survivin-derived peptides as disclosed herein. "Functional equivalents" as used in the present context is established by means of reference to the corresponding functionality of a predetermined fragment of the sequence in question. Functional equivalence can be established by e.g. similar binding affinities to HLA class I molecules, or similar potency demonstrated by the ELISPOT assay.

Functional equivalents or variants of a survivin-derived peptide as described herein will be understood to exhibit amino acid sequences gradually differing from the preferred, predetermined sequences, as the number and scope of insertions, deletions and substitutions including conservative substitutions, increases. This difference is measured as a reduction in homology between a preferred, predetermined sequence and the survivin-derived variant or survivin-derived functional equivalent.

The homology between amino acid sequences may be calculated using algorithms well known in the art. Fragments sharing homology with fragments comprising or consisting of consecutive survivin-derived amino acid residues are to be considered as falling within the scope of the present invention when they are preferably at least about 90% homologous, such as at least 94% homologous, including 95%, 96%, 97%, 98% or 99% homologous with a predetermined survivin-derived peptide.

Furthermore, it may be advantageous to carry out post-translational modifications of the peptides of the invention. It has been shown that exposure of breast carcinoma MCF-7 or cervical carcinoma HeLa cells to anticancer agents including ADRIAMYCIN® (doxorubicin), TAXOL® (paclitaxel), or UVB resulted in a 4-5-fold increased survivin expression. Changes in survivin levels after anticancer treatment did not involve modulation of survivin mRNA expression and were independent of de novo gene transcription. Conversely, inhibition of survivin phosphorylation on $Thr^{34}$ by the cyclin-dependent kinase inhibitor flavopiridol resulted in loss of survivin expression, and nonphosphorylatable survivin $Thr^{34}$→Ala exhibited accelerated clearance as compared with wild-type survivin. Sequential ablation of survivin phosphorylation on $Thr^{34}$ enhanced tumor cell apoptosis induced by anticancer agents independently of p53 and suppressed tumor growth without toxicity in a breast cancer xenograft model in vivo. These data suggest that $Thr^{34}$ phosphorylation critically regulates survivin levels in tumor cells and that sequential ablation of $p34^{cdc2}$ kinase activity may remove the survivin viability checkpoint and enhance apoptosis in tumor cells.

Accordingly, it is contemplated that the survivin-derived peptides of the invention encompass phosphorylated peptides. Native survivin phosphopeptide antigens may be identified by scanning for the presence of MHC peptide binding motifs around the phosphorylation site Thr34. Thus, possible survivin-derived phosphopeptide sequences Include T P E R M A E A G F, a putative HLA-B35- and/or HLA-B7- and/or a HLA-B51-restricted peptide antigen. Additional native phosphopeptides encompassed herein include: HLA-A2: C A C T P E R M A and C T P E R M A E A; HLA-A3: F L E G C A C T P; HLA-B7/HLA-B35/HLA-B51: W P F L E G C A C T (Phoshorylated Thr residue marked in bold).

A significant feature of the peptide of the invention is its capability to recognise or elicit INF-γ-producing responder T cells, i.e. cytotoxic T cells (CTLs) that specifically recognise the particular peptide in a PBL population or tumour cells of a cancer patient (target cells). This activity is readily determined by subjecting PBLs or tumour cells from a patient to an ELISPOT assay as described in reference (16) and in the following examples. Prior to the assay, it may be advantageous to stimulate the PBL population or the tumour cells to be assayed by contacting the cells with the peptide to be tested. Preferably, the peptide Is capable of eliciting or recognising INF-γ-producing T cells at a frequency of at least 1 per $10^4$ PBLs as determined by an ELISPOT assay as used herein. More preferably the frequency is at least 5 per $10^4$ PBLs, most preferably at least 10 per $10^4$ PBLs, such as at least 50 or 100 per $10^4$ PBLs.

The ELISPOT assay represents a strong tool to monitor survivin peptide specific T-cell responses. However, although it has been shown that ELISPOT reactivity in most cases correlates with the capacity of the CLLs to lyse target cells, the conclusive evidence for this notion can only be given directly. Such direct evidence is provided herein, as it was demonstrated (see Example 2) that survivin reactive cells isolated by means of HLA/peptide complexes possess the functional capacity of lysing target cells. Additionally, it was demonstrated that the isolated CTLs specifically recognising a peptide of the invention were capable of lysing HLA-matched tumour cells of different origin, e.g. melanomas and breast cancer. This finding strongly suggests that cancer cells in general process and present the same endogenous survivin peptide. Therefore, a major implication of the findings herein is that the peptides of the invention are expressed and complexed with HLA molecules on a variety of cancer cells of different histological origins. This renders these cancer cells susceptible to destruction by CTLs and emphasizes the potential usefulness of survivin immunization to control the growth of different neoplasms. The presence of spontaneous CTL-responses in PBLs and tumour cells to HLA-restricted survivin-derived peptide epitopes from patients suffering from three unrelated cancer types, i.e., breast cancer, melanoma and CLL, further substantiates the universal immunotherapeutic potential of this tumour antigen.

Accordingly, in another preferred embodiment the peptide of the invention is capable of eliciting INF-γ-producing cells in a PBL population of a patient having a cancer disease where survivin is expressed including a haematopoietic malignancy including chronic lymphatic leukemia and chronic myeloid leukemia, melanoma, breast cancer, cervix cancer, ovary cancer, lung cancer, colon cancer, pancreas cancer and prostate cancer. Specifically, the peptide of the invention is able to elicit an immune response in the form of T cell having cytotoxic effect against survivin expressing cells of a cancer cell line, including a cell line selected from the breast cancer cell line MCF-7 and the melanoma cell line FM3.

In addition to their capacity to elicit immune responses in PBL populations and cancer cell lines, it was demonstrated that the peptides of the invention are also capable of eliciting cytolytic immune responses in situ, i.e. in solid tumour tissues. This was demonstrated by providing HLA-peptide complexes, e.g. being multimerised and being provided with a detectable label, and using such complexes for immunohistochemistry stainings to detect in a tumour tissue CTLs that are reactive with the epitope peptide of the invention. Accordingly, a further significant feature of the peptide of the invention is that it is capable of in situ detection in a tumour tissue of CTLs that are reactive with the epitope peptide.

It is contemplated that the peptides of the invention, in addition to their capacity to bind to HLA molecules resulting in the presentation of complexes of HLA and peptides on cell surfaces, which complexes in turn act as epitopes or targets for cytolytic T cells, may elicit other types of immune responses, such as B-cell responses resulting in the production of antibodies against the complexes and/or a Delayed Type Hypersensitivity (DTH) reaction. The latter type of immune response is defined as a redness and palpable induration at the site of injection of the peptide of the invention.

It is well known, that the different HLA molecules are of different prevalence in the major human populations. Accordingly, there is a requirement for identifying peptide epitopes restricted to several HLA class I molecules to extend the patient cohort that can be treated according to the methods of the present invention. The characterisation of multiple survivin epitopes with different HLA restriction elements broadens the clinical potential of this target antigen in two important ways: (i) It increases the number of patients eligible for immunotherapy based on survivin-derived peptides. The HLA-A2 antigen is expressed by around 50% of the Caucasian and Asian populations, the HLA-A1 and HLA-A3 antigens are both expressed by around 25% of Caucasians and 5% of Asians, whereas the HLA-A11 antigen is expressed by around 15% of Caucasians and 30% of Asians. Even though these numbers cannot be summed up due to co-expression, a combination of peptides restricted by a multiplicity of these would certainly encompass most cancer patients, (ii) The collective targeting of several restriction elements in each patient Is likely to decrease the risk of immune escape by HLA-allele loss. Loss of a single HLA allele is a significant component of MHC alterations described for cancer cells, whereas total loss of Class I expression is a rather infrequent event. Thus, with the identification of survivin epitopes restricted to different HLA alleles, it is now possible to target more than one HLA-molecule simultaneously in patients with allelic overlap.

Accordingly, based on the disclosure of the present invention the person of skill in the art would be able to develop highly immunogenic multi-epitope vaccines. Preferably, such vaccines should be designed so as to facilitate a simultaneous delivery of the best-suited survivin-derived peptides optionally in combination with other suitable peptides and/or adjuvants as described hereinafter.

Furthermore, as previously described, there has been an increased focus on eliciting tumor-specific T helper cell immunity, i.e., vaccinating with class II-MHC restricted epitopes despite the fact that tumors generally do not express class II MHC. This Is based on the recent finding that the induction and efficacy of the vaccine-induced anti-tumor response in many cases requires the cooperation of tumor-specific CD4 positive $T_h$ cells. Thus, an important factor driving the development of vaccines having a more complex composition is the desire to target multiple tumor antigens e.g. by designing vaccines comprising or encoding a collection of carefully selected CTL and $T_h$ cell epitopes.

Obviously, multi-epitope vaccines constitute an efficient way to raise immunity against epitopes derived from several different antigens without the need for introducing (genes encoding) potentially hazardous proteins such as oncoproteins. Such vaccines also permit selective induction of immunity against subdominant and cryptic T cell epitopes, which can be especially important in the case of tumor-associated autoantigens for which tolerance may exist for the epitopes that are prominently presented in normal tissues. Furthermore, antigen-presenting cells may fail to present certain epitopes that are expressed on tumor cells because of functional differences between the immunoproteasomes of antigen-presenting cells and the 'constitutive' proteasomes present in most tumor cells. In the case of peptide-based vaccines, such epitopes can be administered in an 'MHC-ready' form, which enables presentation through exogenous loading independently of antigen uptake and processing by host antigen-presenting cells.

It is evident that the findings of the present invention provide the basis for therapeutic as well as diagnostic applications of the survivin-derived peptides.

Accordingly, in a further aspect the present invention provides a pharmaceutical composition comprising one or more of the peptides of the invention alone or in suitable combination with other proteins or peptide fragments. In specific embodiments such other proteins or peptide fragments include but are not limited to proteins involved in regulation of cell apoptosis or peptide fragments hereof. Suitable examples of such proteins can be selected from the Bcl-2 protein family, e.g., the Bcl-2 protein, the Bcl-w protein, the Mcl-1 protein, the Bcl-XL protein, and peptide fragments derived from any of the proteins. Other known apoptosis inhibitors include members of the inhibitor of apoptosis protein (IAP) family such as X-IAP, C-IAP1 and C-IAP2 these proteins are all relatively ubiquitously expressed whereas the inhibitor of apoptosis polypeptide ML-IAP has a rather selective expression, and is predominantly detected in melanomas. Thus, fragments of ML-IAP capable of eliciting a specific T-cell response i.e a cytotoxic T-cell response or a helper T-cell response may optionally be included in the composition of the present invention.

Useful peptide fragments of ML-IAP include ML-$IAP_{245}$ (RLQEERTCKV) (SEQ ID NO:75), ML-$IAP_{280}$ (QLCPICRAPV) (SEQ ID NO:76), ML-$IAP_{90}$ (RLASFYDWPL) (SEQ ID NO:77), ML-$IAP_{154}$ (LLRSKGRDFV) (SEQ ID NO:78), ML-IAP$_{230}$ (VLEPPGARDV) (SEQ ID NO:79), ML-IAP$_{98}$ (PLTAEVPPEL) (SEQ ID NO:80), ML-IAP$_{34}$ (SLGSPVLGL) (SEQ ID NO:81), ML-IAP$_{54}$ (QILGQLRPL) (SEQ ID NO:82), ML-IAP$_{99}$ (LTAEVPPEL) (SEQ ID NO:83), ML-IAP$_{83}$ (GMGSEELRL) (SEQ ID NO:84) and ML-IAP$_{288}$ (ELPTPRREV) (SEQ ID NO:85).

Additionally, the composition according to the present invention may be proved as a multiepitope vaccine comprising class I restricted epitope and/or class II restricted epitopes as defined hereinbefore.

Example of a presently preferred multiepitope vaccines include "tailor made" combinations of survivin-derived peptide eptiopes depending of the tissue type of the given patient, e.g., a subject carrying HLA-A2, HLA-A3, and HLA-B35 phenotypes could be vaccinated with a vaccine comprising sur1M2, sur9, sur18K10, sur46Y9, sur51Y9. Additionally, the pharmaceutical composition of the invention may advantageously comprise at least one further immunogenic protein or peptide fragment hereof selected from a protein or peptide fragment not belonging to or derived from the survivin protein. In specific embodiments, the immunogenic protein or peptide fragment thereof is derived from the Bcl-2 protein family as described hereinbefore. A further immunogenic Bcl-2-derived peptide is an HLA-A2 restricted peptide having a sequence selected from the following: Bcl$_{172}$, Bcl$_{180}$, Bcl$_{208}$, and Bcl$_{214}$ As the peptides of the invention are relatively small molecules it may be required in such compositions to combine the peptides with various materials such as adjuvants, to produce vaccines, immunogenic compositions, etc. Adjuvants, broadly defined, are substances which promote immune responses. Frequently, the adjuvant of choice is Freund's complete or incomplete adjuvant, or killed B. pertussis organisms, used e.g. in combination with alum precipitated antigen. A general discussion of adjuvants is provided in Goding, Monoclonal Antibodies: Principles & Practice (2nd edition, 1986) at pages 61-63. Goding notes, however, that when the antigen of interest is of low molecular weight, or is poorly immunogenic, coupling to an immunogenic carrier is recommended. Examples of such carrier molecules include keyhole limpet haemocyanin, bovine serum albumin, ovalbumin and fowl immunoglobulin. Various saponin extracts have also been suggested to be useful as adjuvants in immunogenic compositions. Recently, it has been proposed to use granulocyte-macrophage colony stimulating factor (GM-CSF), a well known cytokine, as an adjuvant (WO 97/28816).

Accordingly, the invention encompasses a therapeutic composition further comprising any adjuvant substance including any of the above or combinations thereof. It is also contemplated that the antigen, i.e. the peptide of the invention and the adjuvant can be administered separately in any appropriate sequence.

The choice of antigen in the pharmaceutical composition of the invention will depend on parameters determinable by the person of skill in the art. As it has been mentioned, each of the different peptides of the invention is presented on the cell surfaces by a particular HLA molecule. As such, if a subject to be treated is typed with respect to HLA phenotype, a peptide/peptides are selected that is/are known to bind to that particular HLA molecule.

Alternatively, the antigen of interest is selected based on the prevalence of the various HLA phenotypes in a given population. As an example, HLA-A2 is the most prevalent phenotype in the Caucasian population, and therefore, a composition containing a survivin-derived peptide binding to HLA-A2 will be active in a large proportion of that population. However, the composition of the invention may also contain a combination of two or more survivin-derived peptides, each interacting specifically with a different HLA molecule so as to cover a larger proportion of the target population. Thus, as examples, the pharmaceutical composition may contain a combination of a peptide restricted to a HLA-A molecule and a peptide restricted to a HLA-B molecule, e.g. including those HLA-A and HLA-B molecules that correspond to the prevalence of HLA phenotypes in the target population, such as e.g. HLA-A2 and HLA-B35. Additionally, the composition may comprise a peptide restricted to an HLA-C molecule.

It is comtemplated that useful immunogenic compositions of the inventions in addition to a survivin-derived peptide as defined herein may comprise an immunologically effective amount of the survivin protein as such as it is defined herein or an immunogenic fragment hereof.

The amount of the immunogenic peptide of the invention in the pharmaceutical composition may vary, depending on the particular application. However, a single dose of the immunogen is preferably anywhere from about 10 μg to about 5000 μg, more preferably from about 50 μg to about 2500 μg such as about 100 μg to about 1000 μg. Modes of administration include intradermal, subcutaneous and intravenous administration, implantation in the form of a time release formulation, etc. Any and all forms of administration known to the art are encompassed herein. Also any and all conventional dosage forms that are known in the art to be appropriate for formulating injectable immunogenic peptide composition are encompassed, such as lyophilised forms and solutions, suspensions or emulsion forms containing, if required, conventional pharmaceutically acceptable carriers, diluents, preservatives, adjuvants, buffer components, etc.

The immunoprotective effect of the composition of the invention can be determined using several approaches. Examples hereof are provided in the following examples. A further example on how to determine a CTL response provoked by the immunogenic composition is provided in WO 97/28816, supra. A successful immune response may also be determined by the occurrence of DTH reactions after immunisation and/or the detection of antibodies specifically recognising the peptide(s) of the vaccine composition.

In preferred embodiments, the pharmaceutical composition of the invention is an immunogenic composition or vaccine capable of eliciting an immune response to a cancer disease. As used herein, the expression "immunogenic composition or vaccine" refers to a composition eliciting at least one type of immune response directed against cancer cells. Thus, such an immune response may be any of the types mentioned above: A CTL response where CTLs are generated that are capable of recognising the HLA/peptide complex presented on cell surfaces resulting in cell lysis, i.e. the vaccine elicits the production in the vaccinated subject of effector T-cells having a cytotoxic effect against the cancer cells; a B-cell response giving rise to the production of anti-cancer antibodies; and/or a DTH type of immune response.

In useful embodiments an immunogenic response directed against a cancer disease is elicited by administering the peptide of the invention either by loading MHC class I molecules on antigen presenting cells (APCs) from the patient, by isolating PBLs from the patient and incubating the cells with the peptide prior to injecting the cells back into the patient or by isolating precursor APCs from the patient and differentiating the cells into professional APCs using cytokines and antigen before injecting the cells back into the patient. Thus, in one embodiment of the present invention, a method for treating cancer patients is one wherein the peptide is administered by presenting the peptide to the patient's antigen presenting cells (APCs) ex vivo followed by injecting the thus treated APCs back into the patient. There are at least two alternative ways of performing this. One alternative is to isolate APCs from the cancer patient and incubate (load) the MHC class I molecules with the peptide. Loading the MHC class I molecules means incubating the APCs with the peptide so that the APCs with MHC class I molecules specific for the peptide will bind the peptide and therefore be able to present it to T cells. Subsequently, the APCs are re-injected into the patient. Another alternative way relies on the recent discoveries made in the field of dendritic cell biology. In this case, monocytes (being dendritic cell precursors) are isolated from the patient and differentiated in vitro into professional APC (or dendritic cells) by use of cytokines and antigen. This is described in Examples 3 and 5, where adherent PBLs (being mainly monocytes) are cultured in vitro together with GM-CSF, IL-4 and TNF-α. Subsequently, the in vitro generated DCs are pulsed with the peptide and injected into the patient.

Due to the fact that survivin appears to be expressed in most cancer forms, it is very likely that vaccines of the invention can be provided to control any type of cancer disease where survivin is expressed. Thus, as examples, the vaccine composition of the invention is immunologically active against a haematopoietic malignancy including chronic lymphatic leukemia and chronic myeloid leukemia, melanoma, breast cancer, cervix cancer, ovary cancer, lung cancer, colon cancer, pancreas cancer and prostate cancer.

From the above description, the skilled person will readily realise that the peptides of the invention are useful as cancer diagnostic tools, particularly so, as the peptides are derived from survivin expressed in all cancer types. Therefore, the peptides of the invention provide the basis for developing universally applicable diagnostic and prognostic procedures in respect of cancer diseases. Thus, in other useful embodiments the composition of the invention is a composition for ex vivo or in situ diagnosis of the presence in a cancer patient, e.g. based on the detection of survivin reactive T-cells among PBLs or in tumour tissue.

Accordingly, there is, in still further aspects, provided a diagnostic kit for ex vivo or in situ diagnosis of the presence of survivin reactive T-cells among PBLs or in tumor tissue comprising one or more peptides of the invention, and a method of detecting in a cancer patient the presence of survivin reactive T-cells, the method comprising contacting a tumor tissue or a blood sample with a complex of a peptide of the invention and a Class I HLA molecule or a fragment of such molecule and detecting binding of the complex to the tissue or the blood cells.

Another useful diagnostic or prognostic approach is based on generating antibodies in a heterologous animal species, e.g. murine antibodies directed against a human survivin-derived peptide of the invention, which can then be used, e.g. to diagnose for the presence of cancer cells presenting the peptide. For such Immunisation purposes, the amount of peptide may be less than that used in the course of in vivo therapy, such as that mentioned above. In general, a preferred dose can range from about 1 ng to about 750 ng of peptide. It is also possible to produce monoclonal antibodies based on immunisation with a peptide of the invention. Accordingly, the present invention also relates to a molecule, in particular a monoclonal or polyclonal antibody including a fragment hereof, that is capable of binding specifically to a peptide of the invention and to a molecule that is capable of blocking such a binding, e.g. an antibody raised against the monoclonal or polyclonal antibody directed against a peptide of the invention.

In one aspect, the invention provides a complex of a peptide of the invention and a Class I HLA molecule or a fragment of such molecule, which is useful as a diagnostic reagent such as it is described supra. The complex is made by any conventional means including those described in the following examples. Such a complex may be monomeric or multimeric.

The present invention provides the means for alleviating or curing a cancer disease. Accordingly, it is a further aspect of the invention to use the peptides as defined hereinbefore for the preparation of a medicament for the treatment of cancer. A still further aspect of the present invention relates to the use of a molecule or a composition as defined hereinbefore for the preparation of a medicament for the treatment of cancer. Preferably, a cancer disease associated with the expression of survivin, including as examples: a haematopoietic malignancy including chronic lymphatic leukemia and chronic myeloid leukemia, melanoma, breast cancer, cervix cancer, ovary cancer, lung cancer, colon cancer, pancreas cancer and prostate cancer. The use comprises administering to a patient suffering from the disease an effective amount of the pharmaceutical composition according to the invention, a molecule that is capable of binding specifically to a peptide of the invention and/or a molecule that is capable of blocking the binding of such a molecule.

In some cases it will be appropriate to combine the use of the invention with a conventional cancer treatment such as radiotherapy or chemotherapy.

Figure 2:
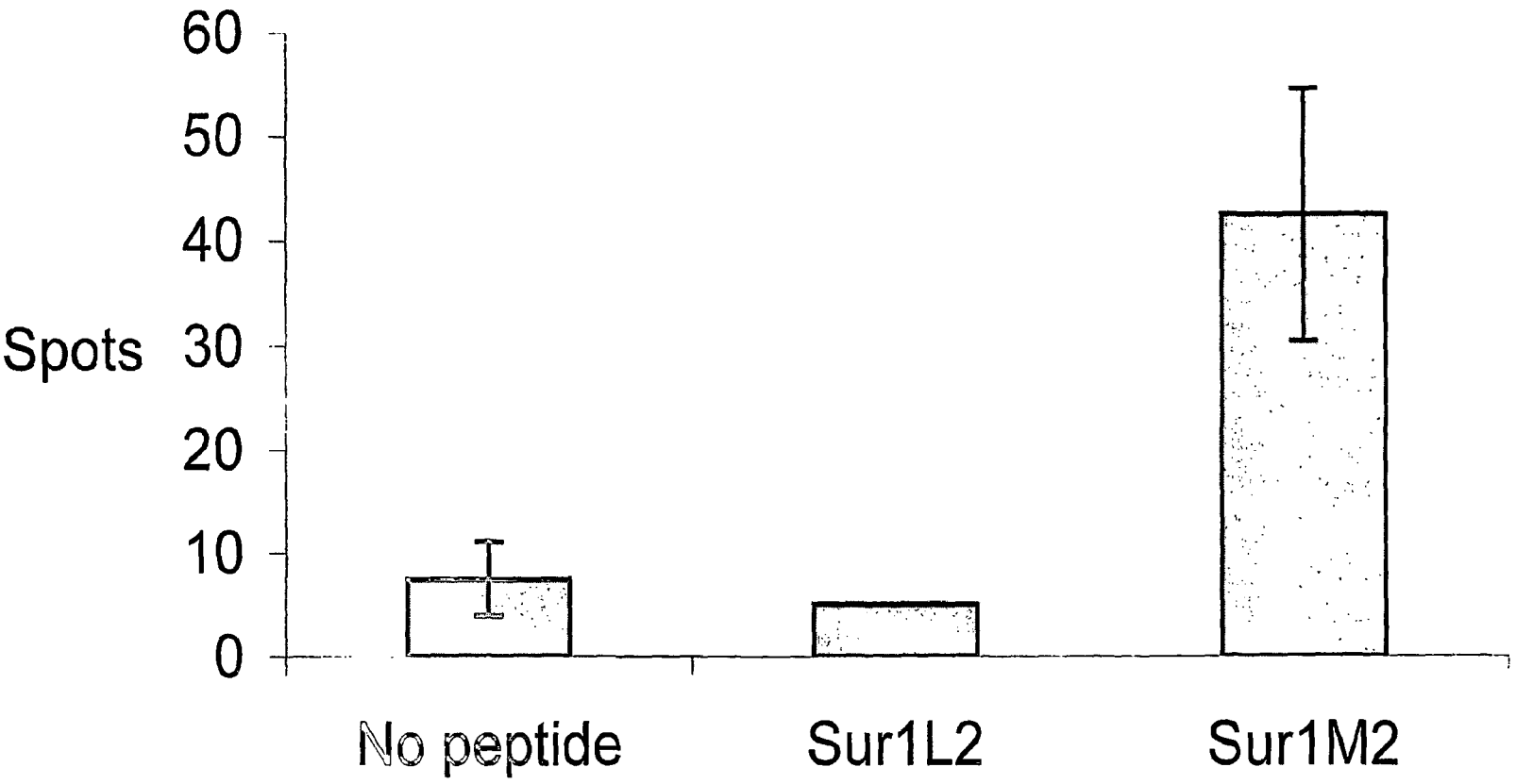
Figure 3:
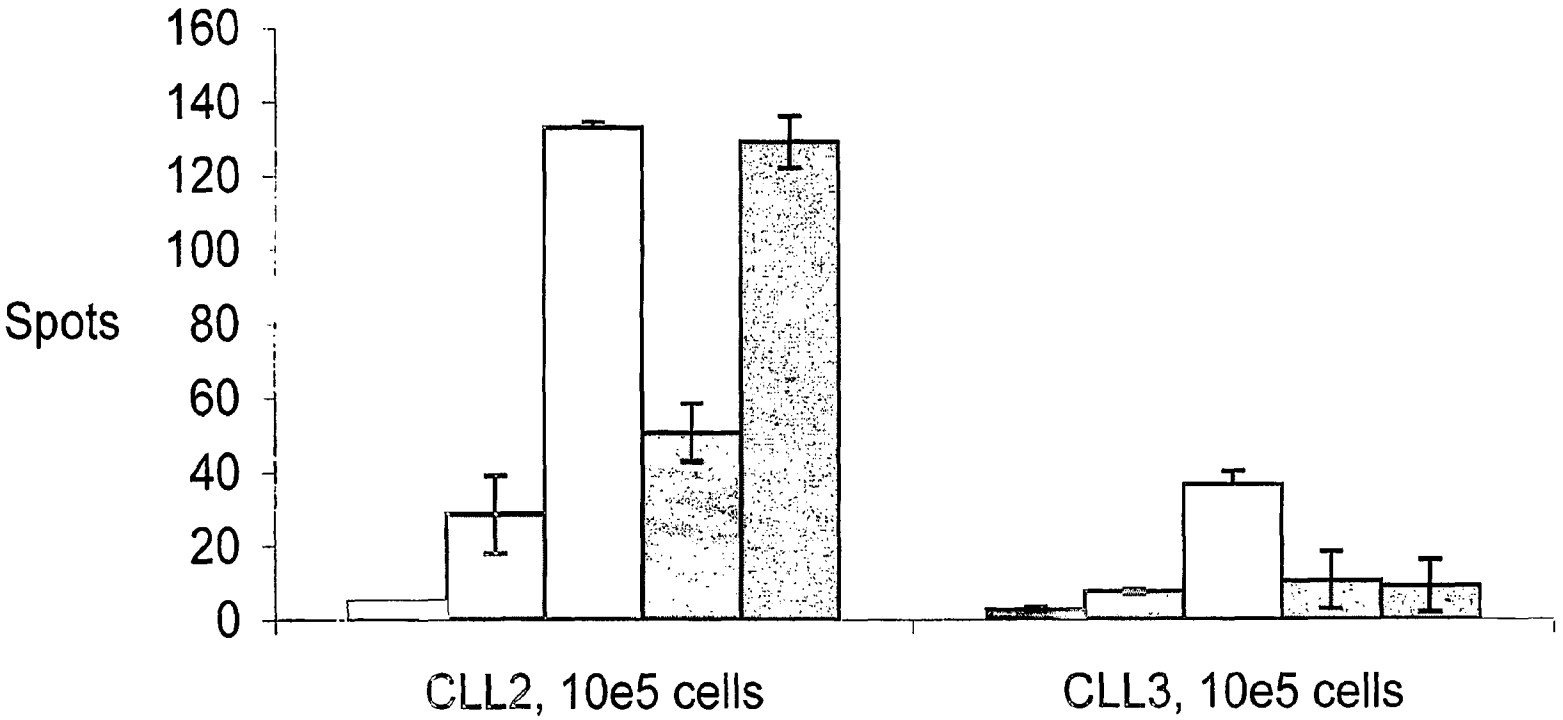
Figure 4:
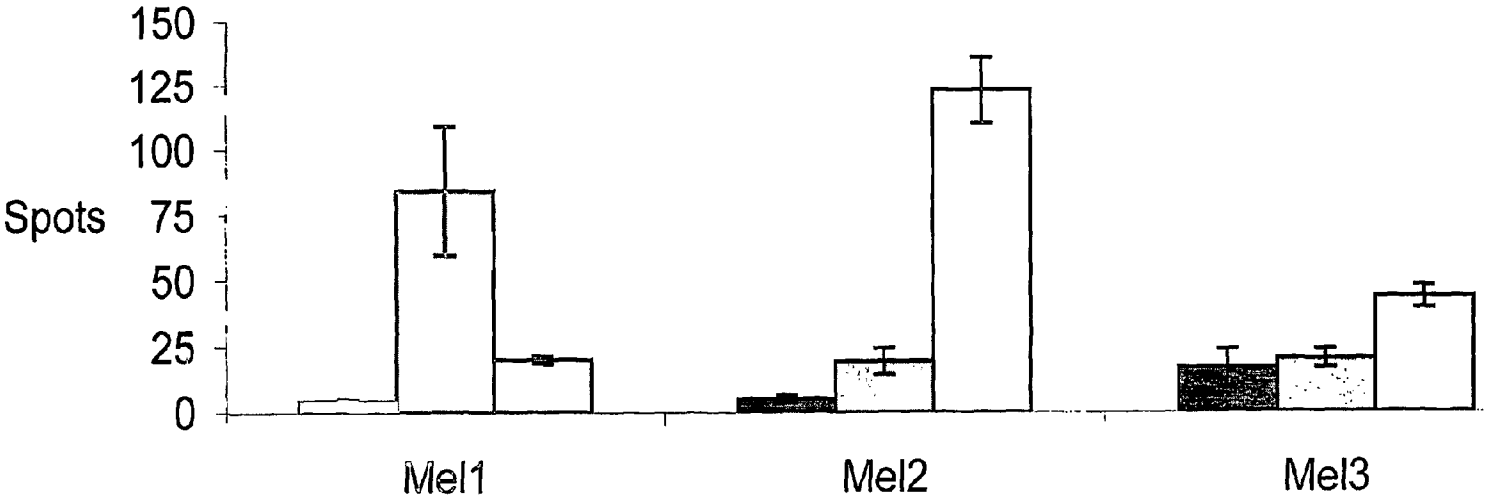
Figure 5:
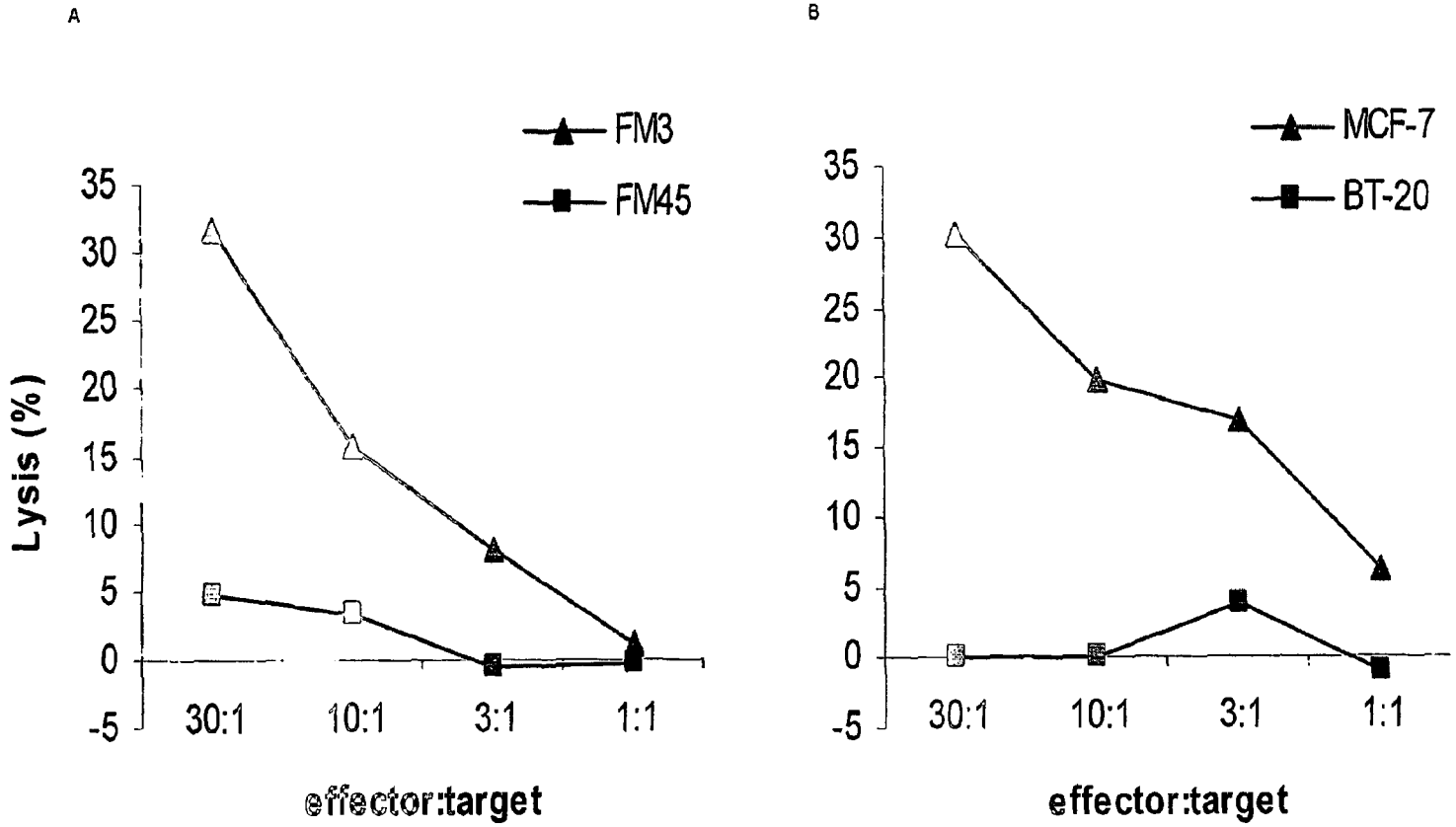
Figure 6:
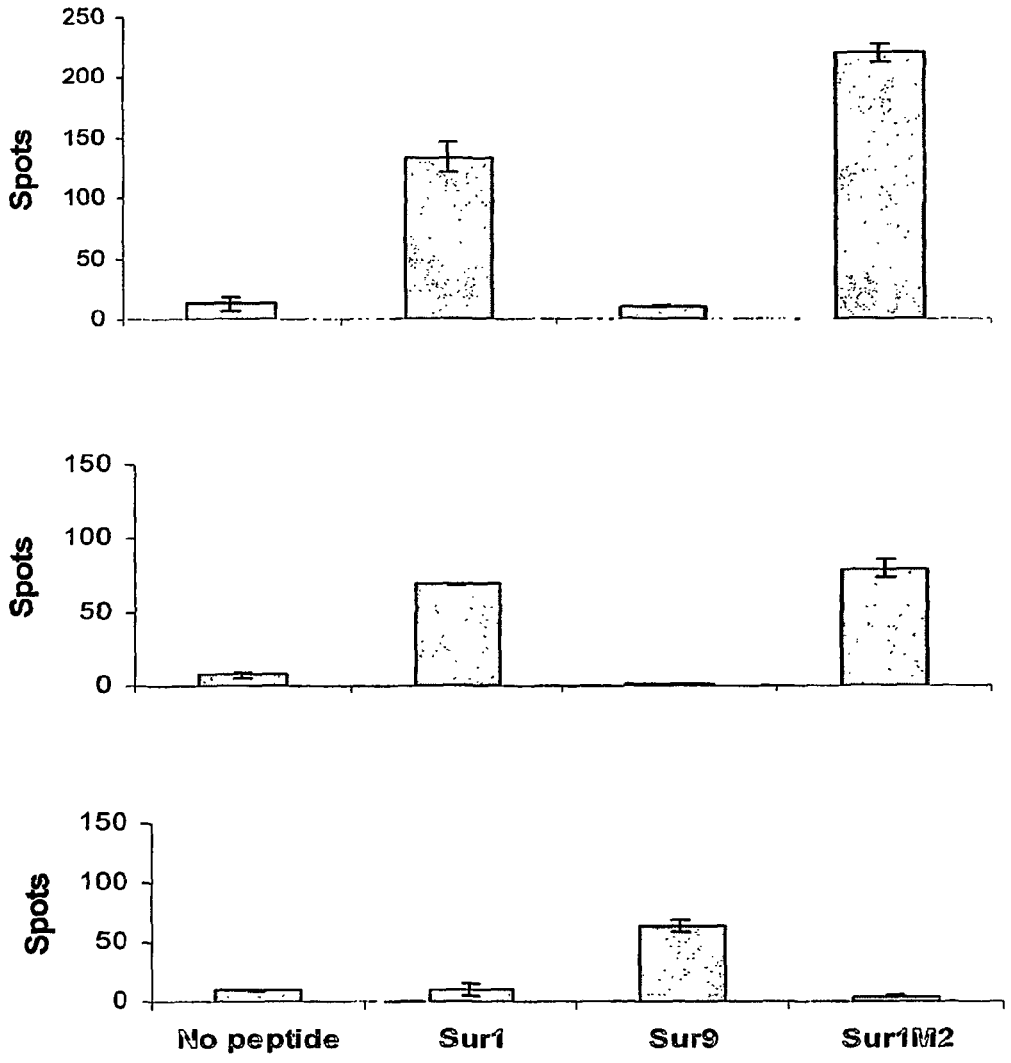
Figure 7:
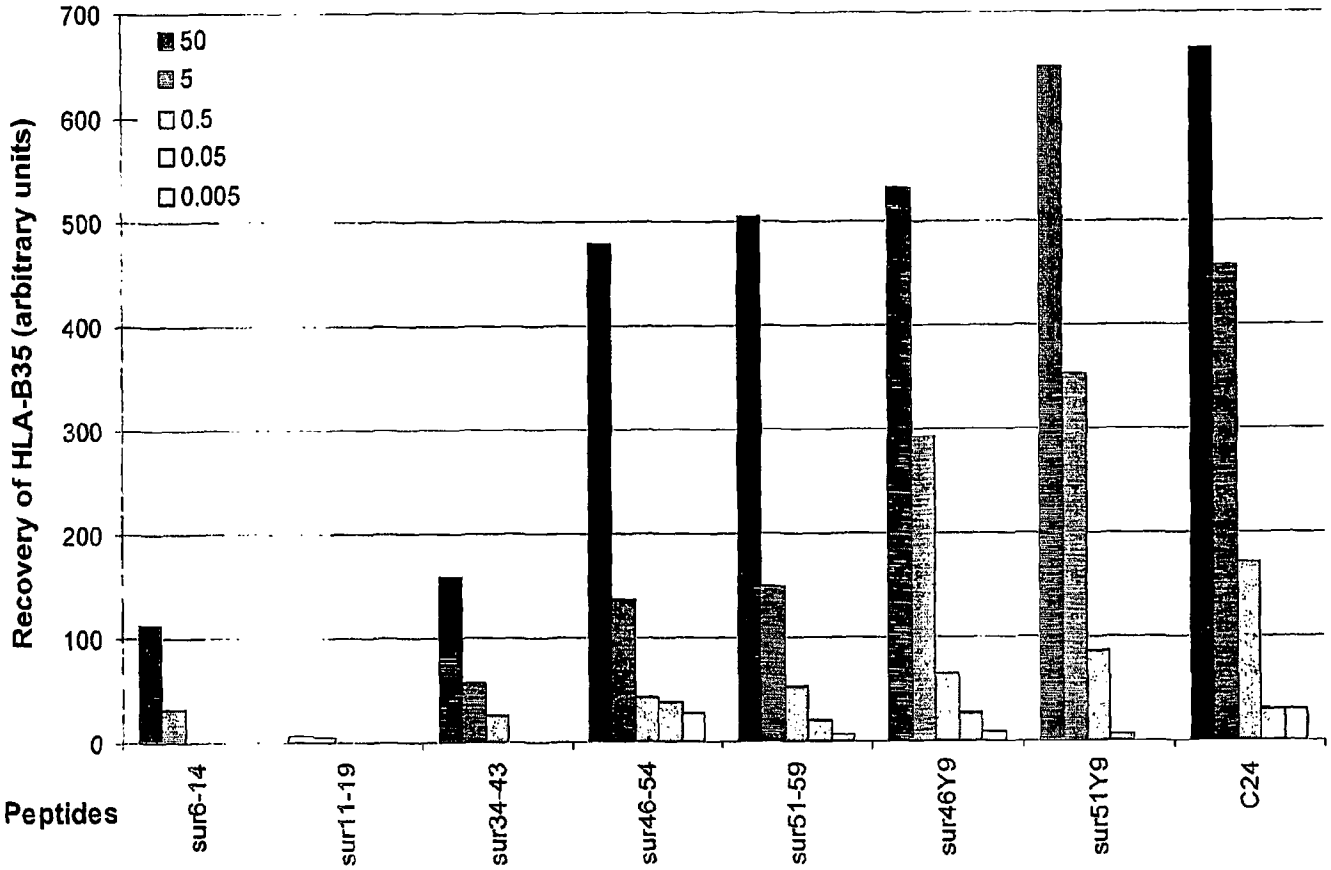
Figure 8:
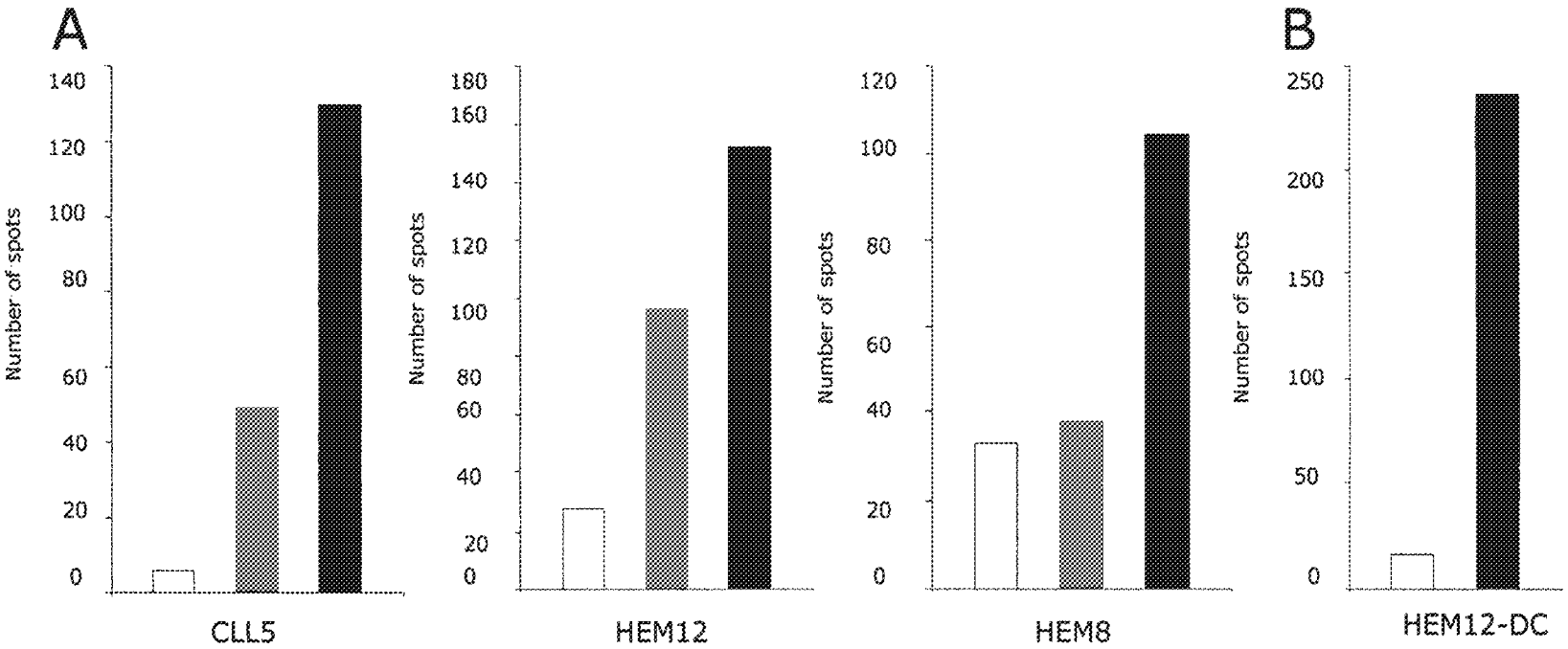
Figure 9:
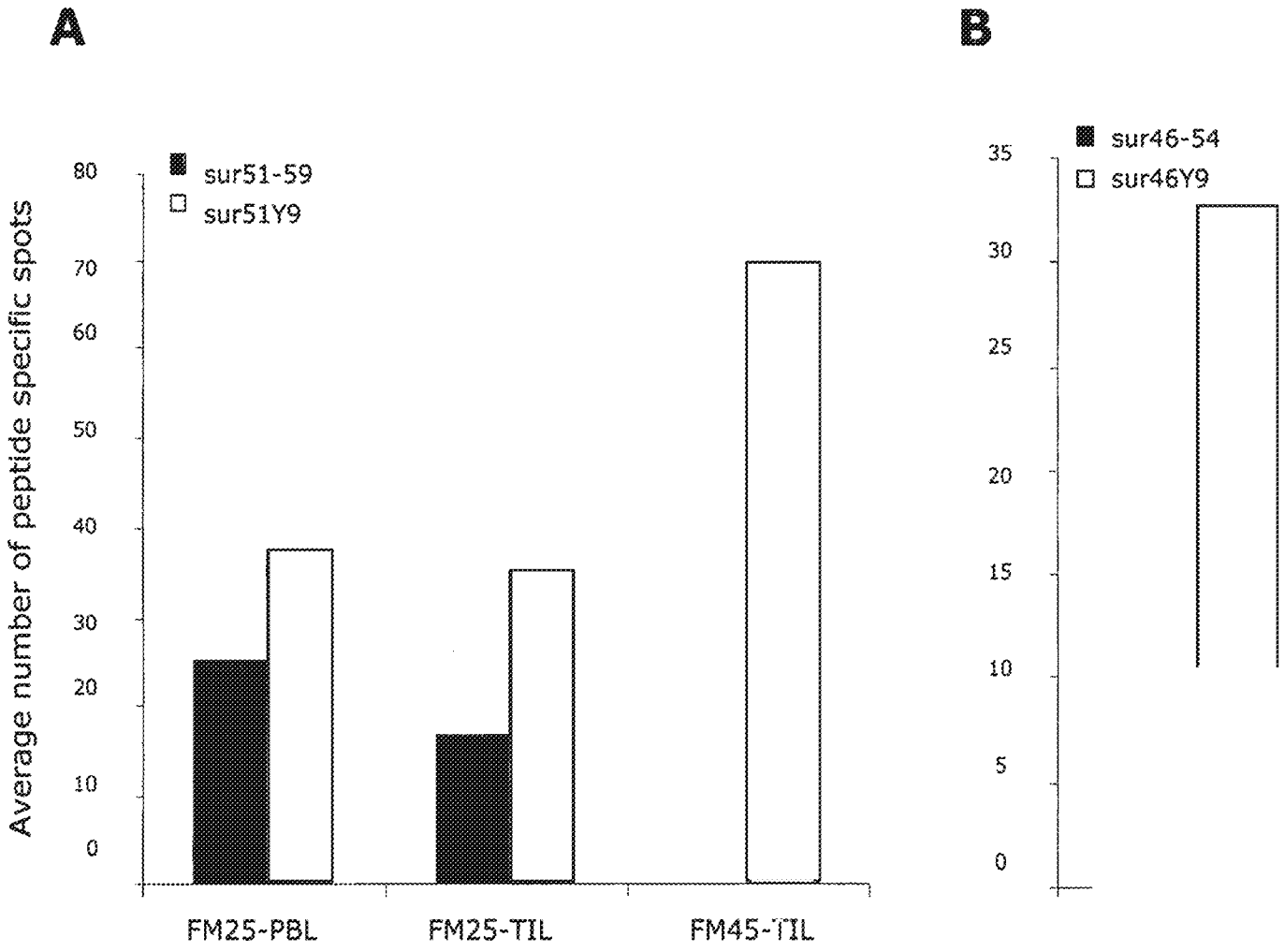
Figure 10:
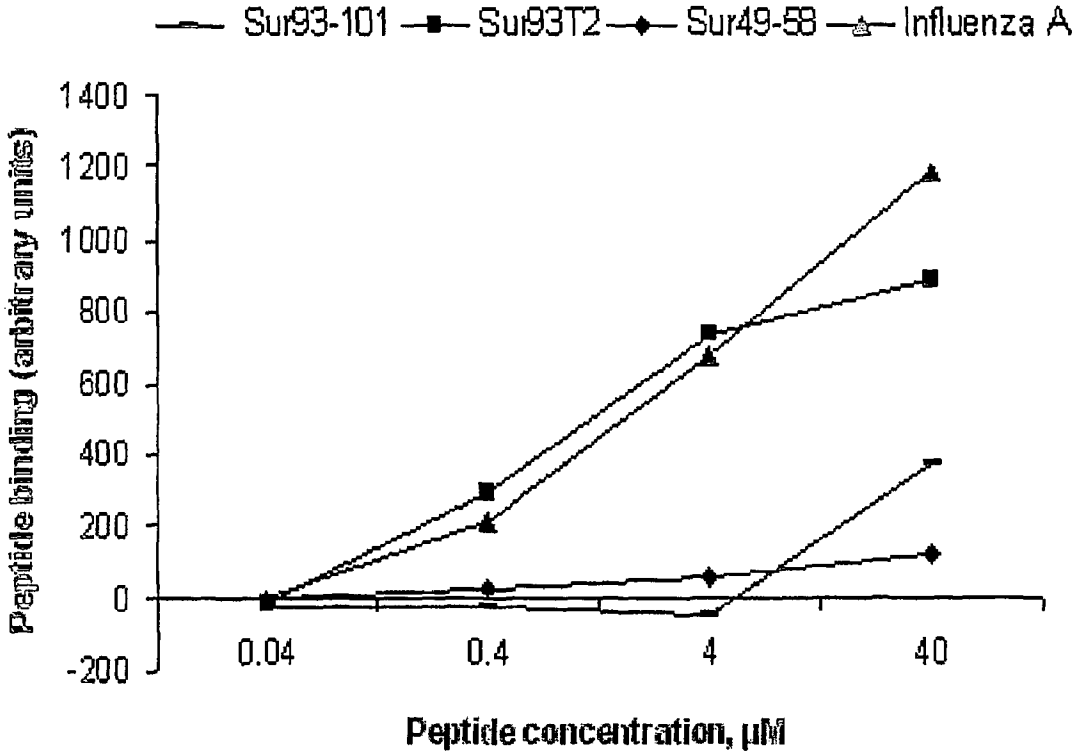
Figure 11:
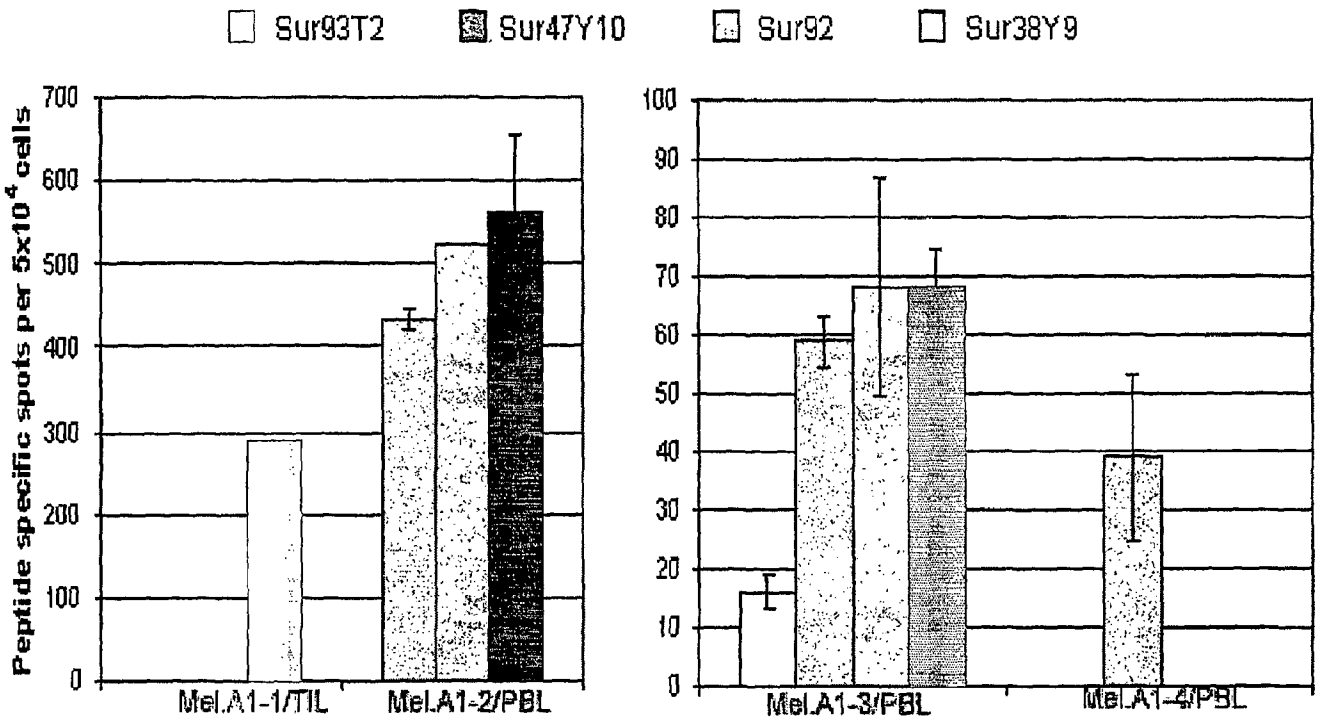
Figure 12:
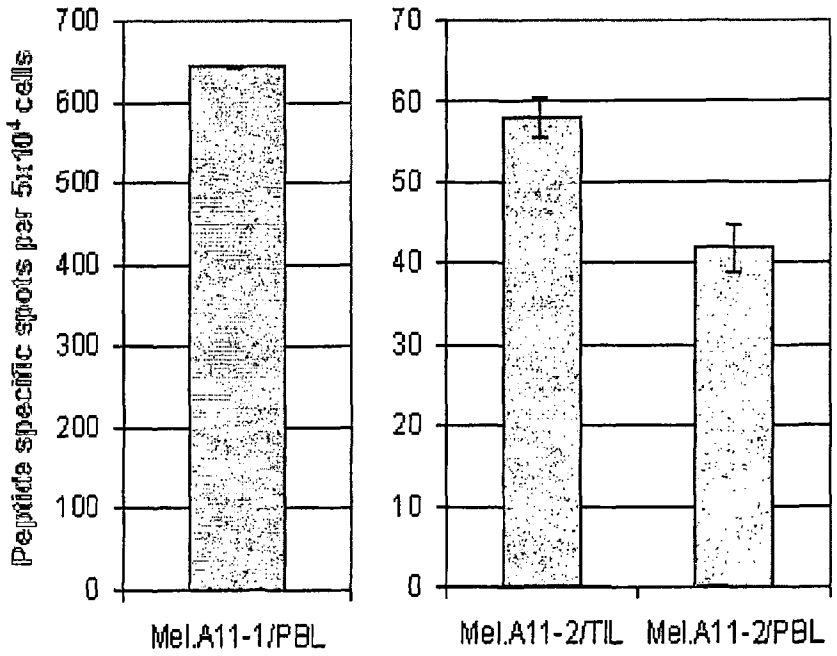
Figure 13:
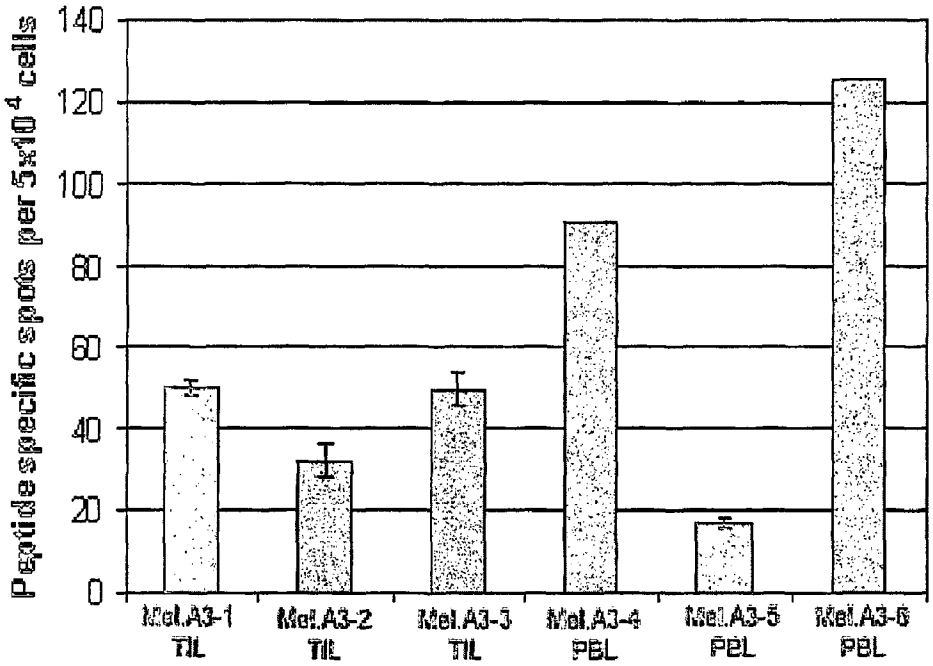
Figure 14:
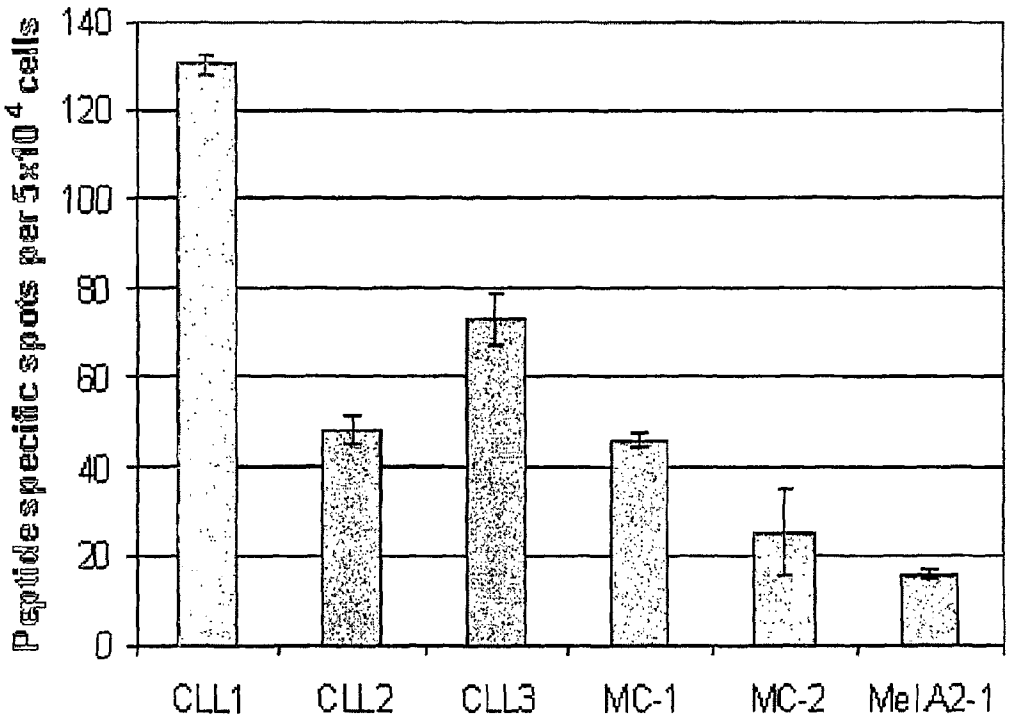
Figure 15:
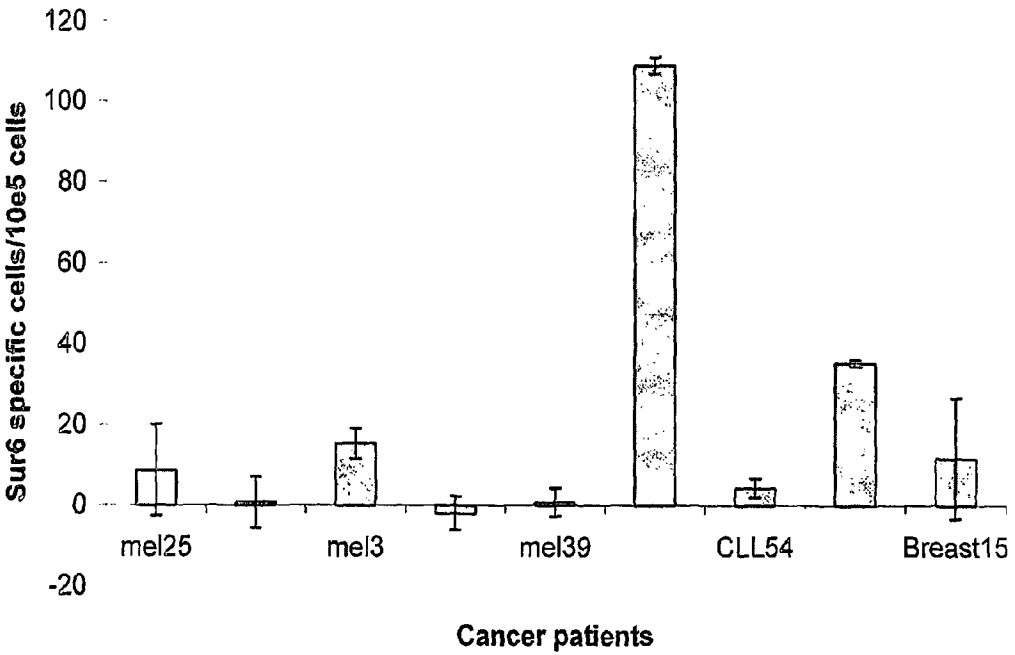
Figure 16:
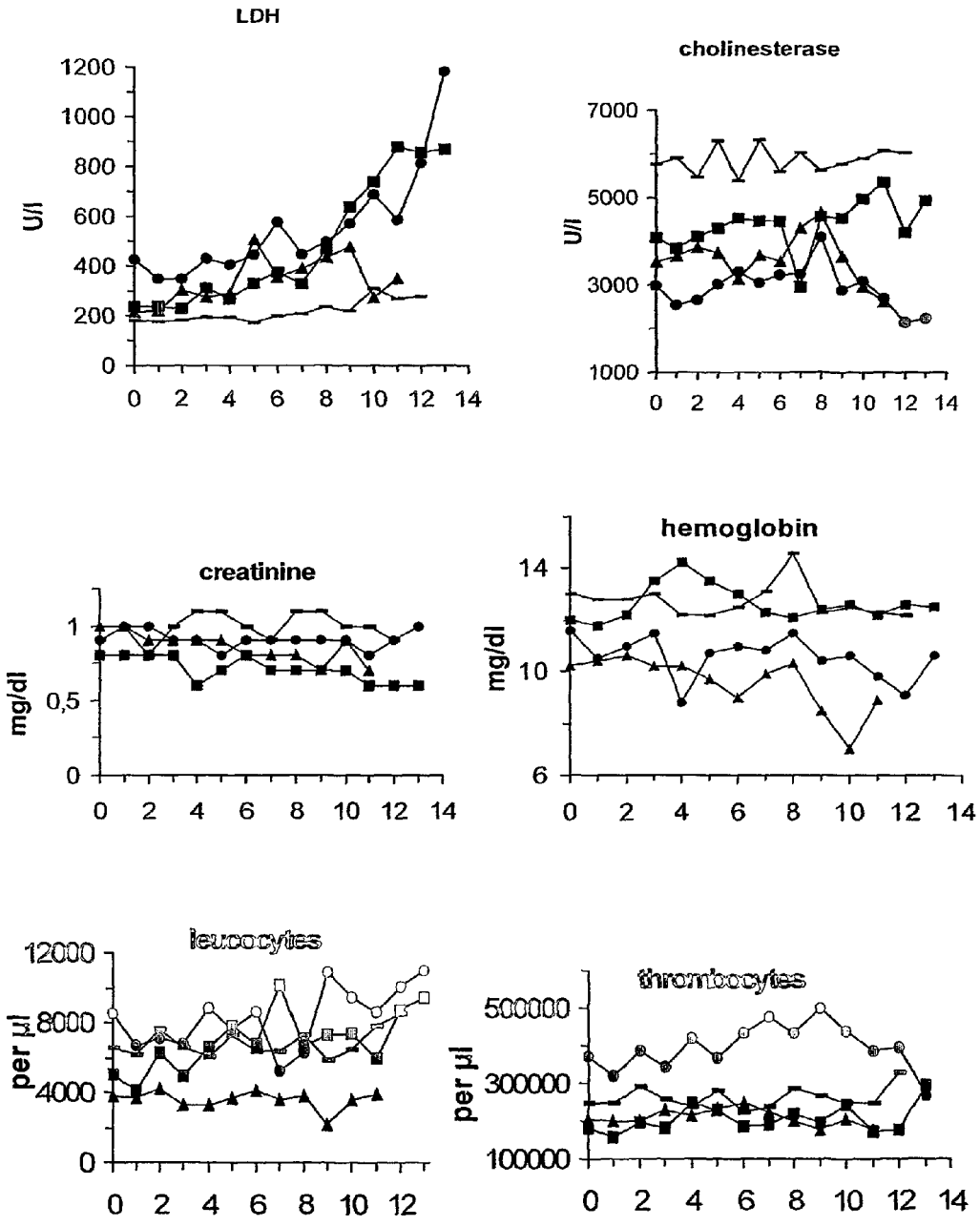

The invention will now be described in further details in the below, non-limiting examples and the figures, wherein FIG. 1 illustrates T-cell response as measured in an ELISPOT in patient CLL1 to no peptide, Surl (LTLGEFLKL, SEQ ID NO:10) peptide and Sur9 (ELTLGEFLKL, SEQ ID NO:3) peptide. PBLs were stimulated once with peptide before plated at $6\times10^5$ cells per well in duplicate. The average number of spots per peptide was calculated using a CCD scanning device and a computer system, FIG. 2 illustrates T-cell response as measured in an ELISPOT in patient CLL1 to no peptide, the peptide analogue Sur1L2 (LLLGEFLKL, SEQ ID NO:4), and the peptide analogue Sur1M2 (LMLGEFLKL, SEQ ID NO:5). PBLs were stimulated once with peptide before plated at $10^4$ cells per well in duplicate. The average number of spots per peptide was calculated using a CCD scanning device and a computer system, FIG. 3 shows responses as measured in an ELISPOT in patient CLL2 and CLL3 to no peptide (black bar), the Sur1 (LTLGEFLKL, SEQ ID NO:10) peptide (grey bar), the Sur9 (ELTLGEFLKL, SEQ ID NO:3) peptide (white bar), the analogue peptide Sur1L2 (LLLGEFLKL, SEQ ID NO:4) (light grey bar), and the analogue peptide Sur1M2 (LMLGEFLKL, SEQ ID NO:5) (dark grey bar). Each experiment was performed with $10^5$ cells per well in duplicate, and the average number of spots was calculated, FIG. 4 represents T cells that were Isolated from tumour infiltrated lymph nodes from patient Mel1, Mel2, and Mel3, stimulated once in vitro and analyzed in an ELISPOT assay for response to no peptide (black bar) the peptides Sur1 (LTLGEFLKL, SEQ ID NO:10) (grey bar) and Sur9 (ELTLGEFLKL, SEQ ID NO:3) (white bar). Each experiment was performed in duplicate with $10^5$ cells per well. In each experiment two wells without addition of peptide was also included. The average number of spots per peptide was calculated for each patient, FIG. 5 shows functional activity of survivin specific CTLs. CTLs were isolated from a melanoma infiltrated lymph node using survivin coated magnetic beads. (A) Specific lysis of melanoma cell lines; the HLA-A2 positive FM3 (triangle) and the HLA-A2 negative FM45 (square). (B) Specific lysis of breast cancer cell lines; the HLA-A2 positive MCF-7 (triangle) and the HLA-A2 negative BT-20 (square), FIG. 6 shows frequency of survivin reactive CTLs in PBL from breast cancer patients. Reactivity was examined in three breast cancer patients (top, middle, and bottom, respectively) by the ELISPOT. For each patient the assays were performed in the absence of peptide, in the presence of sur1 peptide, in the presence of sur9, and in the presence of the modified sur1M2 peptide. $1\times10^4$ effector cells per well were used. The graph depicts the quantification of reactive cells; grey columns represent the average number of IFN-γ producing cells, FIG. 7 illustrates HLA-35 binding of survivin-derived peptides and analysis of the peptide-mediated recovery of HLA-B35 molecules by survivin-derived peptides. Lysates of metabolically labeled T2-B35 cells were incubated at 4° C. in the presence of 50, 5, 0.5, 0.05 and 0.005 mM of peptide. The recovery of HLA-B35 was analyzed in an assembly assay and quantified subsequent to IEF-gel electrophoresis, using ImageGauge phosphorimager software (FUJI photo film Co., LTD., Japan). The $C_{50}$ value is the concentration of the peptide required for half-maximal binding to HLA-B35, FIG. 8 shows spontaneous T-cell responses observed in PBLs from cancer patients. A) The number of IFNγ spot forming cells measured in ELISPOT assay without peptide (white bars), with sur51-59 (black bars) or sur46-54 (gray bars), among in vitro stimulated PBLs from patient CLL5 ($10^5$ cells/well), HEM12 ($10^5$ cells/well), and HEM8 ($5\times10^4$ cells/well). B) The number of spot forming cells among $1.7\times10^5$ PBLs from HEM12, cultured for 10 days with peptide-pulsed matured autologous dendritic cells. The columns represent the average of two measurements, FIG. 9 demonstrates spontaneous T-cell responses against native and modified survivin peptides in melanoma patients. A) The number of spot forming cells measured in ELISPOT assay against sur51-59 and sur51Y9 from patient FM25 in PBLs ($4\times10^3$ cells/well) and TILs ($7\times10^4$ cells/well) as well as TILs from FM45 ($10^4$ cells/well). B) The number of spot forming cells measured in ELISPOT assay against sur46 and sur46Y9 measured in TILs from FM74 ($5\times10^3$ cells/well). The columns represent the average of two measurements with the non-specific IFNγ release subtracted, FIG. 10 illustrates binding affinity of survivin-derived peptides to HLA-A1. Class I MHC heavy chain bands were quantified on a Phosphorimager. The mount of stabilized HLA-A1 heavy chain is directly related to the binding affinity of the added peptide. The peptide-mediated recovery of HLA-A1 (arbitrary units) induced by 40, 4, 0.4, 0.04 μM of Sur93-101 (line), Sur93T2 (square), Sur49-58 (circle) or Influenza A, PB1 591-599 (triangle), FIG. 11 shows spontaneous responses against HLA-A1 restricted peptides. Spontaneous T-cell responses against survivin-derived peptides as measured by ELISPOT assay. The average number of peptide specific IFNγ spots formed in response to Sur92-101, Sur38Y9, Sur47Y10, and Sur93T2 among $5\times10^4$ in vitro stimulated PBL or TIL from melanoma patients. The peptide specific responses showed were observed among analyses of 6 PBL samples and 3 TIL samples from melanoma (MeI) patients. Non-specific IFNγ spots are subtracted. Bars: range of duplicates, FIG. 12 shows spontaneous responses against HLA-A11 restricted peptides. Spontaneous T-cell responses against survivin-derived peptides as measured by the ELISPOT assay. The average number of peptide specific IFNγ spots formed in response to Sur53-62 among $5\times10^4$ in vitro stimulated PBL or TIL from cancer patients. The peptide specific responses showed were observed among analyses of 5 melanoma (MeI) patients (5 PBL, 1 TIL) and 2 CLL (CLL) patients (PBL). Non-specific IFNγ spots are subtracted. Bars: range of duplicates, FIG. 13 illustrates spontaneous responses against HLA-A3 restricted peptides. Spontaneous T-cell responses against survivin-derived peptides as measured by the ELISPOT assay. The average number of peptide specific IFNγ spots formed in response to Sur18K10 among $5\times10^4$ in vitro stimulated PBL or TIL from melanoma patients. The peptide specific responses showed were observed among analyses of 23 PBL samples and 4 TIL samples from melanoma (MeI) patients. Non-specific IFNγ spots are subtracted. Bars: range of duplicates, FIG. 14 illustrates spontaneous responses against HLA-A2 restricted peptides. Spontaneous T cell responses against survivin-derived peptides as measured by the ELISPOT assay. The average number of peptide specific IFNγ spots formed in response to the 11mer peptide, Sur18-28 among $5\times10^4$ in vitro stimulated PBL from cancer patients. The peptide specific responses showed were observed among analyses of 10 PBL samples from 2 melanoma (MeI), 6 CLL (CLL), and 2 mamma carcinoma (MC) patients. Non-specific IFNγ spots are subtracted. Bars: range of duplicates, FIG. 15 illustrates spontaneous T cell responses against survivin-derived peptides as measured by the ELISPOT assay. The average number of peptide specific IFNγ spots formed in response to sur6-14 (LPPAWQPFL) among $10^5$ in vitro stimulated PBL from five melanoma patients (mel25, mel26, mel3, mel6, mel39), two CLL patients (CLL1, CLL54) and 2 breast cancer patients (breast11, breast 15). Non-specific IFNγ spots are subtracted, FIG. 16 illustrates the laboratory values of stable detection of LDH, cholinesterase, creatinine, hemoglobin, leucocytes and thrombocytes following vaccination therapy of four patients (▲ RW, ● KN, – WWE, ■ GB), and FIG. 17 demonstrates kinetic analysis of immunity to survivin peptides assessed by IFNγ ELISPOT. PBMCs were obtained before the first DC vaccination and three months thereafter. The numbers of IFNγ spot-forming cells above background are depicted.

In the following table, amino acid sequences for peptides used herein and their respective SEQ ID NOs are listed:

| SEQ ID NO: | DESIGNATION | SEQUENCE |
|---|---|---|
| 1 | Sur6 | FLKLDRERA |
| 2 | Sur8 | TLPPAWQPFL |
| 3 | Sur9 | ELTLGEFLKL |
| 4 | Sur1L2 | LLLGEFLKL |
| 5 | Sur1M2 | LMLGEFLKL |
| 6 | Sur 46-54 | CPTENEPDL |

-continued

| SEQ ID NO: | DESIGNATION | SEQUENCE |
|---|---|---|
| 7 | Sur51-59 | EPDLAQCFF |
| 8 | Sur46Y9 | CPTENEPDY |
| 9 | sur51Y9 | EPDLAQCFY |
| 10 | Sur1 | LTLGEFLKL |
| 11 | C1 | ILKEPVHGV |
| 12 | Sur2 | RAIEQLAAM |
| 13 | Sur3 | KVRRAIEQL |
| 14 | Sur4 | STFKNWPFL |
| 15 | Sur5 | SVKKQFEEL |
| 16 | Sur7 | TAKKVRRAI |
| 17 | Sur10 | ETAKKVRRAI |
| 18 | Sur 6-14 | LPPAWQPFL |
| 19 | Sur 11-19 | QPFLKDHRI |
| 20 | Sur 34-43 | TPERMAEAGF |
| 21 | C24 | YPLHEQHQM |
| 22 | Sur14-22 | LKDHRISTF |
| 23 | Sur38-46 | MAEAGFIHC |
| 24 | Sur93-101 | FEELTLGEF |
| 25 | Sur47-56 | PTENEPDLAQ |
| 26 | Sur49-58 | ENEPDLAQCF |
| 27 | Sur92-101 | QFEELTLGEF |
| 28 | C1 | VSDGGPNLY |
| 29 | sur14Y9 | LKDHRISTY |
| 30 | sur93Y9 | FEELTLGEY |
| 31 | sur92Y9 | QFEELTLGEY |
| 32 | sur34Y9 | TPERMAEAGY |
| 33 | sur49Y9 | ENEPDLAQCY |
| 34 | Sur92T2 | QTEELTLGEF |
| 35 | Sur92S2 | QSEELTLGEF |
| 36 | Sur93T2 | FTELTLGEF |
| 37 | Sur93S2 | FSELTLGEF |
| 38 | Sur38Y9 | MAEAGFIHY |
| 39 | Sur47Y10 | PTENEPDLAY |
| 40 | Sur 5-13 | TLPPAWQPF |
| 41 | Sur 53-61 | DLAQCFFCF |
| 42 | Sur 54-62 | LAQCFFCFK |
| 43 | Sur 95-103 | ELTLGEFLK |
| 44 | Sur 112-120 | KIAKETNNK |

-continued

| SEQ ID NO: | DESIGNATION | SEQUENCE |
|---|---|---|
| 45 | Sur 13-22 | FLKDHRISTF |
| 47 | Sur 53-62 | DLAQCFFCFK |
| 50 | Sur 103-112 | KLDRERAKNK |
| 51 | Sur 112-121 | KIAKETNNKK |
| 52 | Sur 113-122 | IAKETNNKKK |
| 53 | C3 | ILRGSVAHK |
| 54 | Sur5K9 | TLPPAWQPK |
| 55 | Sur53K9 | DLAQCFFCK |
| 56 | Sur54L2 | LLQCFFCFK |
| 57 | Sur13K9 | FLKDHRISTK |
| 58 | Sur18K10 | RISTFKNWPK |
| 59 | Sur113L2 | ILKETNNKKK |
| 60 | SurEx3-A3-1 | TIRRKNLRK |
| 61 | SurEx3-A3-2 | PTIRRKNLRK |
| 62 | Sur2b-A3-1 | RITREEHKK |
| 63 | C4 | AVFDRKSDAK |
| 64 | C6 | QPRAPIRPI |
| 65 | C7 | RPPIFIRRL |
| 66 | Sur4-14 | PTLPPAWQPFL |
| 67 | Sur18-28 | RISTFKNWPFL |
| 68 | Sur54-64 | LAQCFFCFKEL |
| 69 | Sur86-96 | FLSVKKQFEEL |
| 70 | Sur88-98 | SVKKQFEELTL |
| 71 | Sur103-113 | KLDRERAKNKI |
| 72 | Ebv, BMLF1 | GLCTLVAML |
| 73 | Hiv, Pol | ILKEPVHGV |
| 74 | Influenza A, nucleoprotein 265-273 | ILRGSVAHK |

Example 1

Identification of a Cytotoxic T-Lymphocyte Response to the Apoptosis Inhibitor Protein Survivin in Cancer Patients Summary Using CTL epitopes derived from survivin, specific T-cell reactivity against such antigens in peripheral blood from chronic lymphatic leukemia (CLL) patients and in tumor-infiltrated lymph nodes from melanoma patients by ELISPOT analysis have been studied. CTL responses to survivin-derived peptide epitopes were detected in three out of six melanoma patients and in three out of four CLL patients. No T-cell reactivity was detected in PBL from six healthy controls. Thus, survivin-derived peptides may serve as important and widely applicable targets for anti-cancer immunotherapeutic strategies.

Introduction

The survivin protein was scanned for the presence of HLA-A*0201 (HLA-A2) binding peptide motifs and after successful identification, the peptides were used to test for specific T-cell reactivity in leukemia and melanoma patients by ELISPOT assay. In both patient cohorts CTL responses to two survivin-derived peptide epitopes were detected, whereas no T-cell reactivity could be detected in the healthy controls. These data suggest that survivin represent a widely expressed tumor antigen recognized by autologous T cells.

Materials and Methods

Patients and Normal Controls

Peripheral vein blood samples from 4 patients diagnosed with CLL (designated CLL1-4) and blood samples from 6 normal individuals were collected into heparinised tubes. PBLs were isolated using LYMPHOPREP® (density gradient medium) separation and frozen in fetal calf serum (FCS) with 10% di-methylsulphoxide. Additionally, T lymphocytes from tumor-infiltrated lymph nodes were obtained from 6 melanoma patients (designated mel1-6). Freshly resected lymph nodes were minced into small fragments, crushed to release cells into culture and cryopreserved. PBLs were available from 4 of the melanoma patients. All individuals included were HLA-A2 positive as determined by FACS analysis using the HLA-A2 specific antibody BB7.2. The antibody was purified from hybridoma supernatant. Patient samples were obtained from the State University Hospital, Herlev, Denmark. Informed consent was obtained from the patients prior to any of these measures.

Survivin-Derived Peptides

All peptides were obtained from Research Genetics (Huntsville, Ala., USA) and provided at >90% purity as verified by HPLC and MS analysis. The peptides used are listed in Table 1.

Assembly Assay for Peptide Binding to Class I MHC Molecules

Assembly assays for binding of the synthetic peptides to class I MHC molecules metabolically labeled with [35S]-methionine were carried out as described (12,13). The assembly assay is based on stabilization of the class I molecules after loading of peptide to the peptide transporter deficient cell line T2. Subsequently, correctly folded stable MHC heavy chains are immunoprecipitated using conformation-dependent antibodies. After IEF electrophoresis, gels were exposed to phospholmager screens, and peptide binding was quantified using the IMAGEQUANT® PhosphorImager program (image analysis software) (Molecular Dynamics, Sunnyvale, Calif.).

Antigen Stimulation of PBLs

To extend the sensitivity of the ELISPOT assay, PBLs were stimulated once in vitro prior to analysis (14,15). Fresh and previously frozen PBLs gave similar results in the ELISPOT assay. On day 0, PBLs or crushed lymph node were thawed and plated in 2 ml/well at a concentration of 2×106 cells in 24-well plates (Nunc, Denmark) in AIM V medium (Life Technologies, Roskilde, Denmark), 5% heat-inactivated human serum and 2 mM of L-glutamine in the presence of 10 μM of peptide. In each experiment a well without peptide was included. Two days later 300 IU/ml recombinant interleukin-2 (IL-2) (Chiron, Ratingen, Germany) was added to the cultures. The cultured cells were tested for reactivity in the ELISPOT assay on day 12.

ELISPOT Assay

The ELISPOT assay used to quantify peptide epitope-specific interferon-γ-releasing effector cells was performed as in (16). Briefly, nitrocellulose bottomed 96-well plates (MULTISCREEN® MAIP N45 (96-well assay plate), Millipore, Hedehusene, Denmark) were coated with anti-IFN-γ antibody (1-D1K, Mabtech, Nacka, Sweden). The wells were washed, blocked by AIM V® medium (serum-free

TABLE 1

Peptides examined in this study and their binding affinity to HLA-A2

| Name | Protein[a] | Sequence | SEQ ID NO: | $C_{50}$ (μM)[b] |
|---|---|---|---|---|
| C1 | HIV-1 $pol_{476-484}$ | ILKEPVHGV | 11 | 0.7 |
| Sur1 | $Survivin_{96-104}$ | LTLGEFLKL | 10 | >100 |
| Sur2 | $Survivin_{133-141}$ | RAIEQLAAM | 12 | Not binding |
| Sur3 | $Survivin_{130-138}$ | KVRRAIEQL | 13 | >100 |
| Sur4 | $Survivin_{20-28}$ | STFKNWPFL | 14 | Not binding |
| Sur5 | $Survivin_{88-96}$ | SVKKQFEEL | 15 | Not binding |
| Sur6 | $Survivin_{101-109}$ | FLKLDRERA | 1 | 30 |
| Sur7 | $Survivin_{127-135}$ | TAKKVRRAI | 16 | Not binding |
| Sur8 | $Survivin_{5-14}$ | TLPPAWQPFL | 2 | 30 |
| Sur9 | $Survivin_{95-104}$ | ELTLGEFLKL | 3 | 10 |
| Sur10 | $Survivin_{126-135}$ | ETAKKVRRAI | 17 | Not binding |
| Sur1L2 | | LLLGEFLKL | 4 | 1 |
| Sur1M2 | | LMLGEFLKL | 5 | 1 |

[a]The value range listed in subscript indicates the position of the peptide in the survivin sequence as disclosed in U.S. Pat. No. 6,245,523

[b]The $C_{50}$ value is the concentration of the peptide required for half maximal binding to HLA-A2 determined as described below media), and cells were added in duplicates at different cell concentrations. Peptides were then added to each well and the plates were incubated overnight. On the following day, medium was discarded and the wells were washed prior to addition of biotinylated secondary antibody (7-B6-1-Biotin, Mabtech). The plates were incubated for 2 hours, washed and Avidin-enzyme conjugate (AP-Avidin, Calbiochem, Life Technologies) was added to each well. Plates were incubated at RT for 1 hour and the enzyme substrate NBT/BCIP® (nitro-blue tetrazolium and 5-bromo-4-chloro-3'-indolyphosphate) (Gibco, Life Technologies) was added to each well and incubated at room temperature for 5-10 min. The reaction was terminated by washing with tap water upon the emergence of dark purple spots. The spots were counted using the ALPHA IMAGER SYSTEM® (imaging system) (Alpha Innotech, San Leandro, Calif. USA) and the peptide specific CTL frequency could be calculated from the numbers of spot-forming cells. The assays were all performed in duplicate for each peptide antigen.

Results

Binding of Survivin Derived Peptides to HLA A2

The amino acid sequence of the survivin protein was screened for the most probable HLA-A2 nona- and decamer peptide epitopes, using the main HLA-A2 specific anchor residues (17). Ten survivin-derived peptides were synthesized and examined for binding to HLA-A2. An epitope from HIV-1 pol476-484 (ILKEPVHGV, SEQ ID NO:11) (Table 1) was used as a positive control. The peptide concentration required for half maximal recovering of class I MHC ($C_{50}$ value) was 0.7 μM for the positive control. In comparison, the peptide designated Sur9 (ELTLGEFLKL, SEQ ID NO:3) bound at an affinity of $C_{50}$=10 μM. The peptides designated Sur6 (FLKLDRERA, SEQ ID NO:1) and Sur8 (TLPPAWQPFL, SEQ ID NO:2), respectively bound to HLA-A2 at $C_{50}$=30 μM, whereas Sur1 (LTLGEFLKL, SEQ ID NO:10) and Sur3 (KVRRAIEQL, SEQ ID NO:13) bound weaker ($C_{50}$>100 μM). Five of the peptides examined (Sur2, Sur4, Sur5, Sur7, and Sur10) did not bind to HLA-A2.

Since Sur1 is a weak HLA-A2 binder, two analogue peptides designated Sur1L2 and Sur1M2, respectively in which a better anchor residue (leucine or methionine) replaced the native threonine at position 2 were synthesized. Both of these peptides bind with almost similar high affinity to HLA-A2 as the positive control ($C_{50}$=1 μM).

CTL Response to Survivin in CLL Patients

PBLs from four HLA-A2 positive CLL patients were stimulated once in vitro before examination in the ELISPOT assay. This procedure was chosen to extend the sensitivity of the ELISPOT. All of the above 10 survivin-derived peptides were included in the first line of experiments. Responses were detected to Sur1 and Sur9 and only data for these peptides are given in the figures. FIG. 1 shows CTL reactivity to Sur1 and Sur9 as determined in patient CLL1. Each spot represents a peptide reactive, INF-γ-producing cell. The average number of spots per peptide was calculated using a CCD scanning device and a computer system. Fifty-two Sur9 peptide specific spots (after subtraction of spots without added peptide) per $6\times10^5$ were detected in the CLL1 patient (FIG. 1). No response was detected to the weak HLA-A2 binding peptide Sur1, however the patient responded strongly to the strong HLA-A2 binding peptide analogue Sur1M2 (35 peptide specific spots per $10^4$ cells) (FIG. 2). No response was detected to the other strong HLA-A2 binding peptide analogue Sur1L2 in this patient (FIG. 2). Patient CLL2 responded strongly to Sur9 (128 peptide specific spots per $10^5$ cells) and weakly to Sur1 (22 peptide specific spots per $10^5$ cells) (FIG. 3). The response to the Sur1L2 analogue was only slightly increased relative to the natural epitope, whereas the patient responded similarly strongly to the Sur1M2 peptide as to the decamer peptide Sur9. In patient CLL3 a weak response to Sur9 was observed (FIG. 3). No response to Sur1 or the modified Sur1 peptides were observed in the patient. No survivin responses were detected in the last patient CLL4 (data not shown). PBLs from 6 healthy HLA-A2 positive controls were analyzed to investigate whether a response to survivin could be detected in healthy individuals. No response was observed in any of the controls to any of the survivin-derived peptides.

CTL Response to Survivin in Melanoma Patients

T lymphocytes isolated from tumour infiltrated lymph nodes from HLA-A2 positive melanoma patients were examined. The freshly resected lymph node was minced into small fragments and crushed to release cells into culture. Cells were stimulated once with peptide in vitro before examination in the ELISPOT assay. Survivin specific T cells were detested in three of the six patients analyzed. A strong Sur9 response was detected in patient Mel2 and Mel3. A weaker response to the Sur1 peptide was also detected in these patients (FIG. 4). In Mel1 the response to the weakly binding peptide Sur1 was stronger than the response to the stronger HLA-A2 binder Sur9 (FIG. 4). No response was detected in the tumor-infiltrated lymph nodes from the last three melanoma patients (Mel4-6). PBLs from two of the survivin reacting patients, Mel1 and Mel2, and from two of the non-reacting patients, Mel4 and Mel5, were examined. No response could be detected to either Sur9 or Sur1 in PBLs from any of these patients (data not shown).

Example 2

Spontaneous Cytotoxic T-Cell Responses to Survivin-Derived MHC Class I-Restricted T-Cell Epitopes In Situ and Ex Vivo in Cancer Patients Summary Spontaneous cytotoxic T-cell responses to survivin-derived MHC class I restricted T-cell epitopes were demonstrated in situ as well as ex vivo in breast cancer, leukemia, and melanoma patients. Moreover, survivin reactive T cells isolated by magnetic beads coated with MHC/peptide complexes were cytotoxic to HLA-matched tumours of different tissue types. Being a universal tumor antigen, survivin may serve as a widely applicable target for anti-cancer immunotherapy.

Materials and Methods

Construction of HLA-Peptide Complexes for T-Cell Staining and T-Cell Sorting

A recognition site for enzymatic biotinylation using biotin protein ligase (BirA) in fusion with the 5'-end of the extracellular domains of HLA A*0201 (residues 1-275) was expressed in E. coli BL21 (DE3). The recombinant protein was purified by size (SEPHADEX G 25® (gel filtration), Pharmacia) and ion exchange (MONO-Q®, Pharmacia) chromatography from inclusion bodies solubilised in 8 M urea. The HLA A*0201 was folded in vitro by dilution in the presence of the modified survivin peptide Sur1M2 (LMLGEFLKL, SEQ ID NO:5) or the MAA peptide gp100154-163, and subsequently biotinylated as described previously (35, 36).

After gel filtration on a Pharmacia SEPHADEX G 25® (gel filtration) column to remove unbound biotin, the protein was multimerised with streptavidin-FITC conjugated dextran molecules (kindly provided by L. Winther, DAKO, Denmark) to generate multivalent HLA-dextran compounds for immunohistochemistry. The HLA A*0201 construct was a kind gift of Dr. Mark M. Davis (Dept. of Microbiology and Immunology, Stanford University, Palo Alto, Calif.). Cell separation was performed as previously described (37). Briefly, 5×106 streptavidin-conjugated magnetic beads (Dynal, Oslo, Norway) were washed twice in 200 μl cold PBS, 0.5 μg peptide/A*0201 monomers were added and the mixture incubated for 15 min. at room temperature. After two washes these beads were mixed with PBLs at a ratio of 1:10 and subsequently incubated for 1 h followed by a precipitation of bead-bound cells in a magnetic field. The precipitation step was repeated once.

Immunohistochemistry Stainings

For staining with FITC-conjugated multimeric peptide/MHC complexes, tissue sections were dried overnight and subsequently fixed in cold acetone for 5 min. All incubation steps were performed at room temperature and in the dark: (i) 45 min. of the primary antibody (1:100 diluted), (ii) Cy 3-conjugated goat anti-mouse (1:500 diluted; code 115-165-100, Jackson ImmunoResearch, obtained from Dianova, Hamburg, Germany) for 45 min. and finally (iii) the multimers for 75 min. Between each step the slides were washed two times for 10 min. in PBS/BSA 0.1%. The slides were mounted in VECTASHIELD® (antifade mounting medium) and kept in the refrigerator until observed under the confocal microscope.

Cytotoxicity Assay

Conventional [51Cr]-release assays for CTL-mediated cytotoxicity were carried out as described in (13). Target cells were autologous EBV-transformed B-cell lines, the HLA-A2 positive breast cancer cell line MCF-7 (available at ATCC®), the HLA-A2 positive melanoma cell line FM3 (38), the HLA-A2 negative breast cancer cell line BT-20 (available from ATCC®) and the HLA-A2 negative melanoma cell line FM45 (38). All cancer cell lines expressed survivin as examined by RT-PCR (data not shown).

ELISPOT Assay

The ELISPOT assay was used to quantify peptide epitope-specific IFN-γ releasing effector cells and has been described previously (39). Briefly, nitrocellulose bottomed 96-well plates (MULTISCREEN® (96-well assay plate) MAIP N45, Millipore) were coated with an anti-IFN-γ antibody (1-D1K, Mabtech, Sweden) and non-specific binding was blocked using AIM V® medium (serum-free media) (GibcoBRL, Life Technologies Inc., Gaithersburg, Md., USA). Lymphocytes were added at different cell concentrations together with the specific peptides and T2 cells and incubated overnight at 37° C. Following two washes the biotinylated detection antibody (7-B6-1-Biotin, Mabtech) was added. Specific binding was visualised using alkaline phosphatase-avidin together with the respective substrate (GibcoBRL). The reaction was terminated upon the appearance of dark purple spots, which were quantitated using the ALPHA IMAGER SYSTEM® (imaging system) (Alpha Innotech, San Leandro, Calif., USA). The peptides used for the ELISPOT were Sur1, Sur9 and the Sur1 analogue peptide Sur1M2 as described in Example 1.

Results

In Situ Staining of HLA-A2/Survivin Reactive T Cells

In Example 1 two survivin-derived peptide epitopes recognized by T cells in leukemia and melanoma, i.e., Sur1 were identified. The weak binding affinity of Sur1 to HLA-A2 was improved substantially by replacing threonine at position 2 with a better anchor residue (methionine; Sur1M2). This measure enabled the construction of stable HLA-A2/peptide complexes. These complexes were multimerised using dextran molecules, which were conjugated with streptavidin and FITC. Multimerised MHC-complexes were used to stain acetone-fixed, frozen material. Using a confocal laser microscope, Sur1M2/HLA-A*0201 reactive CTLs could readily be detected in situ in the tumor microenvironment. We depicted such cells in the primary tumor and the sentinel lymph node of a stage III melanoma patient as well as in a primary breast cancer lesion. To ensure the specificity of the staining, a series of negative controls was carried out. Neither the use of peptide/HLA-dextran multimers with peptides derived from the melanoma differentiation antigen gp100 on the same tumour, nor Sur1M2/HLA-dextran multimers in case of a tumour sample obtained from an HLA-A2 negative donor resulted in a positive staining.

Isolated Survivin Reactive CTLs Lyse Tumour Cell Lines of Different Origin

To characterise the functional capacity of survivin-reactive CTLs, these cells were isolated by means of magnetic beads coated with HLA-A2/Sur1M2-complexes (36). A freshly resected melanoma infiltrated lymph node was minced into small fragments and crushed to release cells Into culture. Cells were stimulated once with peptide in vitro prior to isolation. One day after isolation IL-2 was added, and on day 5 the capacity of these cells to kill tumour cells was tested either by ELISPOT or in standard 51Cr release assays. First, by means of ELISPOT analysis it was possible to establish that CTLs isolated using the modified Sur1M2/HLA-A2-complex also responded to the native Sur1 peptide (data not shown). Second, the cytotoxicity of the survivin reactive CTLs against the HLA-A2 positive melanoma cell-line FM3 (FIG. 5 A) and the HLA-A2 positive breast-cancer cell line MCF-7 (FIG. 5 B) was tested. The isolated T cells effectively lysed both HLA-A*0201 cell lines. In contrast, no cytotoxicity was observed against the HLA-A2 negative melanoma cell line FM45 (FIG. 5 A) or the HLA-A2 negative breast cancer cell line BT-20 (FIG. 5 B).

Survivin Reactivity Measured in PBL by ELISPOT

The presence of survivin reactive T cells in PBLs from ten HLA-A2 positive breast cancer patients was examined by the ELISPOT. Before analysis, PBLs were stimulated once in vitro to extend the sensitivity of the assay. Reactivity to the following survivin peptides was examined: Sur1, Sur9 and Sur1M2. Survivin specific T cells were detected in six out of the ten HLA-A2 positive breast cancer patients. Representative examples are given in FIG. 6. In PBLs from two patients a response against Sur1 and the modified analogue Sur1M2, but not against Sur9 (FIG. 6, top, middle) was detected, in three patients a response to Sur9 was detected, but not to Sur1 or Sur1M2 (FIG. 6 bottom), and one patient responded only to Sur1M2. In contrast, no survivin responses were detected in PBLs from 20 healthy HLA-A2 positive donors. Similarly, PBLs from fourteen HLA-A2 positive melanoma patients were examined. Survivin responses were present in seven of these patients (Table 2). Two patients responded to the Sur9 peptide, three to the Sur1M2 peptide, one to both Sur1 and SurM2, and one to all three peptides. In Example 1, T-cell response to survivin in 3 chronic lymphatic leukemia (CLL) patients was tested (Table 2; CLL1, CLL2, CLL3). These studies were extended using PBLs from three additional CLL patients. Notably, all patients produced a T-cell response to at least one survivin epitope (Table 2; CLL5, CLL6, CLL7). In addition, PBLs from one patient suffering from chronic myeloid leukemia (CML) was examined. In this patient, a response to all three peptides was identified (data not shown). The data are summarized in Table 2.

TABLE 2

| Patients with survivin peptide-specific T lymphocytes in PBLs as measured by ELISPOT | | | |
|---|---|---|---|
| Patient | Sur1 | Sur9 | Sur1 M2 |
| Melanoma a) | | | |
| P4 | — | — | 97 |
| P11 | — | — | 112 |
| P13 | — | — | 71 |
| P15 | 61 | — | 101 |
| P17 | — | 172 | — |
| P39 | — | 127 | — |
| P64 | 112 | 70 | 128 |
| Breast cancer b) | | | |
| B1 | 122 | — | 208 |
| B2 | 67 | — | 72 |
| B3 | — | 54 | — |
| B4 | — | 45 | — |
| B5 | — | 19 | — |
| B6 | — | — | 24 |
| CLL c) | | | |
| CLL1 | — | 27 | 320 |
| CLL2 | — | 39 | — |
| CLL3 | 23 | 127 | 122 |
| CLL5 | — | 100 | 124 |
| CLL6 | — | 121 | 360 |
| CLL7 | 68 | 132 | 174 |

a) Frequency of reactive cells per $10^4$; 14 patients examined.
b) Frequency of reactive cells per $10^4$; 10 patients examined.
c) Frequency of reactive cells per $10^5$; 7 patients examined.

Example 3

HLA-B35-Restricted Immune Responses to Survivin-Derived Peptides in Cancer Patients Summary In this study, two survivin-derived epitopes, which are restricted to HLA-B35 were identified and characterized. Specific T-cell reactivity against both of these epitopes was present in the peripheral blood from patients with different haematopoietic malignancies and melanoma. Substitutions of the C-terminal anchor residue improved the recognition by tumor infiltrating lymphocytes from melanoma patients. Furthermore, spontaneous cytotoxic T-cell responses to survivin in situ in a primary melanoma lesion was demonstrated. These epitopes extends the applicability of future vaccine strategies based on survivin peptides in relation to malignancies as well as the HLA profile of the patients involved.

In Examples 1 and 2, HLA-A2 restricted survivin-derived T-cell epitopes were studied. Since HLA-A2 is only expressed in about 30% of the Caucasian population (63), peptide epitopes restricted to other HLA class I molecules need to be identified to extend the fraction of patients that could be treated. In this study, two novel T-cell epitopes from survivin restricted to HLA-B35, which is expressed in 9% of the Caucasian population (63), were identified, and spontaneous immune responses to these survivin peptides were detected in patients with different haematopoietic malignancies and melanoma.

Materials and Methods

Patients

Peripheral vein blood samples from cancer patients were collected, PBLs were isolated using LYMPHOPREP® (density gradient medium) separation, HLA-typed (Department of Clinical Immunology, University Hospital, Copenhagen) and frozen in FCS with 10% DMSO. Ten HLA-B35 positive patients were selected for further analysis. These patients suffered from melanoma, CLL, follicular lymphoma (FL), diffuse large B-cell lymphomas (DLBCL) and Multiple Myeloma (MM), respectively. At the time blood samples were collected patients had not been medically treated within the previous four months. Additionally, tumor-infiltrating lymphocytes (TIL) isolated from lymph nodes were collected from three of the melanoma patients and frozen in FCS with 10% DMSO.

Peptides

Seven synthetic survivin-derived peptides were used in this study: Sur6-14, Sur11-19, Sur34-43, Sur46-54, Sur51-59, Sur46Y9, Sur51Y9, and one EBV-derived peptide, EBNA3A 457-466 (63). All peptides were obtained from Research Genetics (Huntsville, Ala.) and provided at >90% purity, as verified by HPLC and MC analyses. The peptides are listed in Table 3 below.

TABLE 3

| HLA-B35 binding of survivin-derived peptides | | | | |
|---|---|---|---|---|
| Name | Protein and position | Sequence | SEQ ID NO: | $C_{50}$ (μM) |
| Sur6-14 | $Survivin_{6-14}$ | LPPAWQPFL | 18 | >100 |
| Sur11-19 | $Survivin_{11-19}$ | QPFLKDHRI | 19 | Not binding |
| Sur34-43 | $Survivin_{34-43}$ | TPERMAEAGF | 20 | >100 |
| Sur46-54 | $Survivin_{46-54}$ | CPTENEPDL | 6 | 20 |
| Sur51-59 | $Survivin_{51-59}$ | EPDLAQCFF | 7 | 13 |
| Sur46Y9 | Modified peptide | CPTENEPDY | 8 | 4 |
| Sur51Y9 | Modified peptide | EPDLAQCFY | 9 | 1.5 |
| C24 | $EBNA3A_{458-466}$ | YPLHEQHQM | 21 | 0.8 |

Assembly Assay for Peptide Binding to MHC Class I Molecules

The assembly assay described in Examples 1 and 2 was used to measure binding affinity of the synthetic peptides to HLA-B35 molecules metabolically labeled with [S35]methionine. Briefly, the assay is based on peptide-mediated stabilization of empty HLA molecules released, upon cell lysis, from the TAP deficient cell line T2, stably transfected with HLA-B35 (kindly provided by Dr J. Haurum, Symphogen ApS, Lyngby, Denmark). Stably folded HLA-molecules were immunoprecipitated using the conformation-dependent mAb W6/32. The HLA molecules were separated by IEF electrophoresis, gels were exposed to phosphorimager screens (Imaging plate, FUJI photo film Co., LTD., Japan), analyzed and the amount of correctly folded HLA molecules were quantified using ImageGauge phosphorimager software (FUJI photo film Co., LTD., Japan).

Antigen Stimulation of PBLs

To extend the sensitivity of the ELISPOT assay, lymphocytes were stimulated once in vitro with peptide prior to analysis (14, 15). PBLs or TILs were thawed and stimulated with 50 μM of the individual peptide epitopes in 96-well plates for 2 h at 26° C. ($5\times10^5$-$10^6$ cells per peptide), and pooled for further 10 days of culture at 37° C. in x-vivo with 5% human serum (HS), in 24 well plates (Nunc, Roskilde, Denmark), with $2\times10^6$ cells per well. At the second day of incubation 40 μg/ml IL-2 (Apodan A/S, Denmark) were added. At day 10, the cultured cells were tested for reactivity in the ELISPOT assay.

The ELISPOT Assay

The ELISPOT assay used to quantify peptide specific, IFN-γ releasing effector cells in PBLs or TILs collected from cancer patients was performed as described in Example 1. Briefly, nitrocellulose-bottomed 96-well plates (MULTI-SCREEN® (96-well assay plate) MAIP N45; Millipore, Hedehusene, Denmark) were coated with mAb against human IFN-γ, 7.5 μg/ml (1-D1K; Mabtech, Nacka, Sweden). Wells were washed and blocked in x-vivo (X-VIVO 15® BioWhittacker (chemically defined, serum-free media), Molecular Applications Aps, Denmark) and cells were added in duplicates at different concentrations. For antigen presentation, $10^4$ T2-B35 cells, with and without 10 μM peptide, were added per well. Plates were incubated overnight, the cells discarded, and wells washed prior to addition of biotinylated secondary antibody (7-B6-1-Biotin; Mabtech). Plates were incubated 2 h at room temperature, washed and avidin-alkaline phosphatase conjugate was added (AP-Avidin; Calbiochem, Life Technologies, Inc.). After 1 h of incubation at room temperature, the enzyme substrate nitroblue tetrazolium/5-bromo-4-chloro-3-indolyl phosphate (Code No. K0598, DakoCytomation Norden A/S) was added, and dark purple spots emerged in 3-7 min. The reaction was terminated by washing with tap water. Spots were counted using the ALPHA IMAGER SYSTEM® (imaging system) (Alpha Innotech, San Leandro, Calif.), and the frequency of peptide specific T cells were calculated from the number of spot forming cells.

All assays were performed in duplicates for each peptide antigen, and lymphocytes cultured in the same well, were tested in equal cell numbers with and without peptide, to measure the number of peptide specific cells in the culture.

Maturation of Dendritic Cells (DCs)

Adherent cells were isolated from PBLs after 2 h of culture. These were cultured for 10 additional days in RPMI 1640 (GIBCO®, Invitrogen Corporation, UK) with 10% FCS. 800 ng/ml GM-CSF (PreproTech, London, UK) and 40 ng/ml IL-4 (PreproTech) were added every third day. At day 10, DCs were matured for 24 h by adding 50 ng/ml TNF-.alpha. (PreproTech). After maturation, DCs were released and pulsed with 20 μM peptide in the presence of 3 μg/ml. β2-microglobulin for 2 h at 26° C.

Isolation of Peptide Specific T Cells

Antigen specific cells were isolated using sur51Y9/HLA-B35-coated magnetic beads as described in Example 2. Biotinylated monomers of HLA-B35 with sur51Y9 (obtained from ProImmune, Oxford, UK) were coupled to streptavidin coated magnetic beads (DYNABEADS® M-280 (magnetic beads), Dynal A/S, Oslo, Norway) by incubating 2.5 μg monomers with $5\times10^6$ beads in 40 μl PBS for 20 min. at room temperature. The magnetic complexes were washed three times in PBS, using a magnetic device (Dynal A/S, Oslo, Norway) and subsequently mixed with PBLs at a ratio of 1:10 in PBS with 5% BSA, and rotated very gently for 1 h. Antigen specific CD8+ T cells associating with the magnetic complexes were gently washed two or three times. Isolated cells were resuspended several times in x-vivo supplemented with 5% human serum and incubated for 2 h before the magnetic beads were released and removed from the cell suspension. The isolated antigen specific CD8+ T cells were used in ELISPOT assay to analyze the cross-reactivity between the native and modified peptide.

TCR Clonotype Mapping by Denaturing Gradient Gel Electrophoresis (DGGE)

DGGE clonotype mapping of the human TCR BV regions 1-24 has been described in details (66). Briefly, RNA was isolated using the PURESCRIPT® Isolation Kit (RNA isolation kit) (Gentra Systems Inc. MN) and transcribed cDNA was amplified by PCR using primers for the variable regions of the TCR beta chains in conjunction with a common constant region primer. The computer program MELT87 was used to ensure that the amplified DNA molecules were suited for DGGE analysis provided a 50 bp GC-rich sequence (GC-clamp) was attached to the 5'-end of the constant region primer. DGGE analysis was done in 6% polyacrylamide gels containing a gradient of urea and formamide from 20% to 80%. Electrophoresis was performed at 160 V for 4.5 hours in 1×TAE buffer at a constant temperature of 54° C.

Immunohistochemistry Stainings

Multimerised peptide/HLA complexes were used to identify antigen specific T cells in situ in tumor lesions of cancer patients using the procedure described in Example 2. Biotinylated sur51Y9/HLA-B35 monomer was supplied by Proimmune limited, Oxford, UK. The biotinylated monomers of sur51Y9/HLA-B35 were multimerised with streptavidin-FITC-conjugated dextran molecules (kindly provided by L. Winther, DAKO, Glostrup, Denmark) to generate multivalent HLA-dextran compounds for immunohistochemistry. Tissue sections were dried overnight and subsequently fixed in cold acetone for 5 min. All the incubation steps were performed in the dark at room temperature: (a) 45 min of the primary antibody (1:100 diluted) (b) Cy 3-conjugated goat-anti-mouse antibody (1:500 diluted; code 115-165-100; Jackson ImmunoResearch, obtained from Dianova, Hamburg, Germany) for 45 min; and finally (c) the multimers for 75 min. Between each step, the slides were washed two times for 10 min in PBS/BSA 0.1%. The slides were mounted in VECTASHIELD® (antifade mounting medium) and kept in the refrigerator until observed under the confocal microscope (Leica).

Results

Identification of HLA-835 Binding Survivin-Derived Peptides

The amino acid sequence of survivin was screened for nonameric and decameric peptides with anchor residues, according to the peptide-binding motif of HLA-B35 (67). Five peptides were selected containing proline as the N-terminal anchor in position 2 and phenylalanine, leucine, isoleucine or tyrosine as C-terminal anchor residues (Table 3). Assembly assay revealed two peptides, sur51-59 (EPDLAQCFF, SEQ ID NO:7) and sur46-54 (CPTENEPDL, SEQ ID NO:6) that were able to stabilise HLA-B35 efficiently. Additionally, two peptides, sur34-43 (TPERMAEAGF, SEQ ID NO:20) and sur6-14 (LPPAWQPFL, SEQ ID NO:18) showed a weak stabilization, whereas the remaining peptide did not stabilize HLA-B35 at all. The peptide concentration required for half maximal recovery of HLA-B35 (C50) was estimated at 13 μM for sur51-59 and 20 μM for sur46-54. In comparison, the positive control-epitope C24 from EBNA3A458-466 (YPLHEQHQM, SEQ ID NO:21) had an estimated $C_{50}$ value of 0.8 μM.

To enhance the binding affinity of sur46-54 and sur51-59 the C-terminal amino acid was replaced with tyrosine, a better anchor residue (67). The recovery of HLA-B35 mediated by the modified peptides was analyzed in the assembly assay, and $C_{50}$ values were estimated at 1.5 μM for sur51Y9 and 4 μM for sur46Y9 (FIG. 7).

Spontaneous Immune Responses Against Native Peptide Epitopes

Initially, five patients were analyzed for spontaneous immune responses to the four native HLA-B35 binding peptides sur51-59, sur46-54, sur34-43 and sur6-14. These five patients had different haematopoietic malignancies: HEM8 and HEM18 suffered from MM, HEM12 from FL, HEM9 had DLBCL, and CLL5 had CLL.

INF-γ ELISPOT assays were performed on PBLs after 10 days of in vitro stimulation to detect peptide precursor CTLs. Spontaneous immune responses were detected against two of the native HLA-B35 binding peptides, sur51-59 and sur46-54. Two patients, HEM12 and CLL5 showed a response to both sur51-59 and sur46-54, whereas HEM8 only showed a response to sur51-59 (FIGS. 8A and B). No response could be detected in the two remaining patients, HEM9 and HEM18, and no response could be detected to the poorly binding peptides sur34-46 and sur6-14 in any patients.

An alternative approach to in vitro stimulation was used in patient HEM12, i.e. PBLs were co-cultured with matured autologous dendritic cells pulsed with sur51-59 to stimulate a CTL response in vitro. PBLs from this culture showed strong reactivity towards sur51-59 in ELISPOT (FIG. 8B).

Increased Recognition of Modified Peptides

As described above, peptide modifications to enhance the HLA-B35 affinity resulted in a 5-10-fold higher affinity for HLA-B35 relative to the native peptides. A group of five melanoma patients were analyzed for spontaneous immune responses to both the native and modified peptides by means of ELISPOT assay. PBL samples were analyzed after in vitro stimulation, whereas TIL samples were analyzed directly. Spontaneous immune responses were observed in either PBLs or TILs from three of the five patients. FM25 showed reactivity against sur51-59 and sur51Y9 in both PBL and TIL samples (FIG. 9A). FM45 responded only to the modified peptide sur51Y9, with a strong response detectable in TILs. No PBLs were available from this patient (FIG. 9A). FM74 showed a strong response to sur46Y9 in TIL, but no response to the native peptide was detectable (FIG. 9B). A weak response to sur46Y9 was also observed in PBLs from FM74 (data not shown).

Cross-Reactivity Between the Native and Modified Peptide

The high affinity of sur51Y9 to HLA-B35 enables the production of stable monomers of HLA-B35 with sur51Y9. Having established the presence of survivin reactive T lymphocytes in tumor infiltrated lymph nodes and PBLs from different cancer patients, magnetic beads were coated with such HLA-B35/Sur51Y9-complexes and these were used to isolate survivin peptide reactive T lymphocytes from PBL from patient CLL5. This patient showed a strong response to sur51-59. Beads were tightly bound to the cell surface of the specific cells, as visualized by microscopy (data not shown), permitting precipitation of antigen specific cells by a magnetic field. The isolated sur51Y9 specific cells responded strongly to sur51-59, (FIG. 9), whereas no response could be detected in the remaining PBLs (data not shown). The isolation was analyzed by the RT-PCR/DGGE based TCR clonotype mapping. This technique allows the analysis for T-cell clonality in complex cell populations, even if only small numbers of cells are available. These analyses showed that 8 distinct clones were isolated (data not shown).

Antigen Specific T Cells Present In Situ in a Melanoma Lesions

Sur51Y9/HLA-B35 monomers were multimerised using dextran molecules conjugated with streptavidin and FITC. Multimerised MHC-complexes were used to stain acetone-fixed, frozen material using the procedure described in Example 2. Antigen specific cells were visualized using a confocal laser microscope. Sections of primary melanoma from three patients were analyzed, and Sur51Y9/HLA-B35-reactive CTLs could readily be detected in situ in the tumor microenvironment in one of the patients. Co-staining with a mAb against granzyme B showed that these survivin specific CTLs released granzyme B, exerting cytotoxic activity, HLA-B35 negative melanoma patients were used as controls (data not shown).

Example 4

Identification of Novel Survivin-Derived CTL Epitopes with Different HLA-A-Restriction Profiles Summary Novel HLA-A1-, HLA-A2-, HLA-A3- and HLA-A11-restricted survivin epitopes were characterised on the basis of CTL responses in cancer patients. These epitopes significantly increase the number of patients eligible for immunotherapy based on survivin-derived peptides. Additionally, the collective targeting of several restriction elements is likely to decrease the risk of immune escape by HLA-allele loss.

Materials and Methods

Patients

Patient samples were received from the University of Würzburg, Germany and the University Hospital in Herlev, Denmark. Informed consent was obtained from the patients prior to any of these measures. Tissue typing was conducted at Department of Clinical Immunology, University Hospital, Copenhagen, Denmark. Peripheral blood lymphocytes (PBL) from cancer patients with melanoma, mamma carcinoma, and chronic lymphocytic leukemia (CLL) were isolated using Lymphoprep separation and frozen in fetal calf serum (FCS) with 10% dimethylsulphoxide. Furthermore, T lymphocytes from primary lesions and from tumor infiltrated lymph nodes from melanoma patients were obtained. Freshly resected tumor tissue was minced into small fragments, and crushed to release tumor-infiltrating lymphocytes (TIL) for cryopreservation.

Peptides

All peptides were purchased from Invitrogen (Carlsbad, Calif., USA) and provided at >80% purity as verified by HPLC and MS analysis. All peptides used are listed in Table 4, Example below.

Cell Lines

The human T2 cell line is a TAP1 and TAP2 defective hybrid of the B-LCL.174 and the T-LCL CEM cells and thus only express low levels of HLA class I molecules (HLA-A*0201 and HLA-B*5101) at the cell surface. T2 cells transfected with HLA-A*0301 were kindly provided by Dr A McMicheael, IMM, John Radcliffe Hospital, Oxford. T2 cells transfected with HLA-A*1101 were kindly provided by Dr M Masucci, MTC, Karolinska Institute, Stockholm, Sweden. The BM36.1 cell line is also defective in TAP function and has a similar phenotype as T2 with low expression of HLA class I (HLA-A*0101, HLA-B*3501) at the surface. The BM36.1 cells were kindly provided by Dr A Ziegler, Humboldt University, Berlin, Germany.

Assembly Assay for Peptide Binding to MHC Class I Molecules

The binding affinity of synthetic peptides (Invitrogen, Carlsbad, Calif., USA) to HLA-A1, -A2, -A3, or -A11 molecules metabolically labeled with [$^{35}$S]-methionine was measured in the assembly assay, as described previously (12). The assay is based on peptide-mediated stabilization of empty HLA molecules released upon cell lysis, from the TAP-deficient cell lines. Stably folded HLA-molecules were immune-precipitated using the HLA class I-specific, conformation-dependent mAb W6/32, and separated by isoelectric focusing (IEF) gel electrophoresis. MHC heavy chain bands were quantified using the ImageGauge Phosphorimager program (FUJI photo film Co., Carrollton, Tex., USA). The intensity of the band is proportional to the amount of peptide-bound class I MHC complex recovered during the assay. Subsequently, the extent of stabilization of the HLA-molecule is directly related to the binding affinity of the added peptide. The peptide concentration used to analyze the recovery of the HLA-molecules was 40, 4, 0.4, 0.04 μM for HLA-A1 and HLA-A11, and 100, 10, 1, 0.1, 0.01 μM for HLA-A2 and HLA-A3. The $C_{50}$ value was subsequently calculated for each peptide as the peptide concentration sufficient for half maximal stabilization.

Antigen Stimulation of PBL

To extend the sensitivity of the ELISPOT assay, PBL were stimulated once in vitro prior to analysis. At day 0, PBL or crushed lymph nodes were thawed and plated as $2\times10^6$ cells in 2 ml/well in 24-well plates (Nunc, Roskilde, Denmark) in x-vivo medium (Bio Whittaker, Walkersville, Md.), 5% heat-inactivated human serum, and 2 mM of L-glutamine in the presence of 10 μM of peptide. Two days later 20 IU/ml recombinant interleukin-2 (IL-2) (Chiron, Ratingen, Germany) was added to the cultures. The cultured cells were tested for reactivity in the ELISPOT on day 10.

ELISPOT Assay

The ELISPOT assay was used to quantify peptide epitope-specific interferon-.gamma. releasing effector cells as previously described (16). Briefly, nitrocellulose bottomed 96-well plates (MULTISCREEN® MAIP N45 (96-well assay plate), Millipore, Hedehusene, Denmark) were coated with anti-IFN-γ antibody (1-D1K, Mabtech, Nacka, Sweden). The wells were washed, blocked by X-vivo medium, and the cells were added in duplicates at different cell concentrations. The peptides were then added to each well and the plates were incubated overnight. The following day, media was discarded and the wells were washed prior to addition of biotinylated secondary antibody (7-B6-1-Biotin, Mabtech). The plates were incubated for 2 hours, washed, and avidin-alkaline phosphatase conjugate (Calbiochem, Life Technologies, Inc. San Diego, Calif., USA) was added to each well. The plates were incubated at room temperature for one hour, washed, and the enzyme substrate NBT/BCIP® (nitro-blue tetrazolium and 5-bromo-4-chloro-3'-indolyphosphate) (DakoCytomation Norden A/S, Glostrup, Denmark) was added to each well and incubated at RT for 5-10 min. Upon the emergence of dark purple spots, the reaction was terminated by washing with tap-water. The spots were counted using the IMMUNOSPOT® Series 2.0 Analyzer (plate reader) (CTL Analyzers, LLC, Cleveland, US) and the peptide specific CTL frequency could be calculated from the numbers of spot-forming cells. All assays were performed in duplicates for each peptide antigen.

Results

Identification of HLA-A1 Restricted Survivin Epitopes

Binding of Survivin-Derived Peptides to HLA A1

The amino acid sequence of the survivin protein was screened for the most probable HLA-A1 nonamer or decamer peptide epitopes, using the main HLA-A1 anchor residues, aspartic acid (D), glutamic acid (E) at position 3 and tyrosine (Y), phenylalanine (F) at the C-terminus. Accordingly, six survivin-derived peptides were synthesized and examined for binding to HLA-A1 (table 4). Additionally, the two peptides Sur38-46 (MAEAGF1HC)(SEQ ID NO:23) and Sur47-56 (PTENEPDLAQ) (SEQ ID NO:25) was included, in spite they only contain one of the main anchors, since both were identified as possible good binders by the predictive algorithm by Rammensee et al. $C_{50}$ values were estimated for each peptide as the peptide concentration needed for half maximal stabilization of HLA-A1 (table 4). However, only one of these peptides Sur92-101 (QFEELTLGEF) (SEQ ID NO: 27) bound with almost similar high affinity as a known positive control epitope from the Influenza A protein, basic polymerase 1 (PB1) (VSDGGPNLY) as exemplified in FIG. 10. Sur93-101 (FEELTLGEF) (SEQ ID NO:24) had a low binding affinity for HLA-A1, whereas none of the other peptides analyzed bound to HLA-A1 (Table 4). Consequently, we synthesized a number of analogue peptides in which better anchor residues replaced the natural amino acids. We modified the two peptides Sur38-46 (MAEAGF1HC) (SEQ ID NO:23) and Sur47-56 (PTENEPDLAQ) (SEQ ID NO:25) introducing tyrosine (Y) instead of cysteine (C) or glutamine (Q) respectively at the C-terminus. Both of the modified peptides bound strongly to HLA-A1 (table 4). Additionally, we substituted the amino acids at position 2 with the auxiliary anchors threonine (T) or serine (S) in the two peptides Sur92-101 and Sur93-101. These modifications did not have a positive effect of the binding of Sur92-101 to HLA-A1. In contrast, the Sur93T2 (FTELTLGEF) (SEQ ID NO:36) bound with high affinity to HLA-A1 (Table 4). FIG. 10 illustrates the binding of the native low affinity peptide Sur93-101, the high affinity modified peptide Sur93T2 and the non-binding peptide Sur49-58 as compared to the positive control epitope from influenza. Finally, we modified Sur14-22, Sur34-43, Sur49-58, Sur51-59, Sur92-101, and Sur93-101 with tyrosine (Y) at the C-terminus, however this did not improve binding affinity to HLA-A1 for any of these peptides (data not shown).

HLA-A1 Restricted CTL Responses Against Survivin-Derived Peptides in Cancer Patients PBL from six melanoma patients and TIL from three melanoma patients were analyzed for the presence of CTL specific against any of the four high affinity survivin deduced peptides Sur38Y9, Sur47Y10, Sur92-101, and Sur93T2 by means of ELISPOT. T-cell reactivity against at least one of the survivin-derived peptides was observed in three PBL samples and one TIL sample from the total of nine patients analyzed. As seen in FIG. 11, PBL from one patient, Mel.A1-3 hosted a T-cell response against all four peptides, Sur38Y9, Sur47Y10, Sur92-101, and Sur93T2. Mel.A1-2 showed responses against Sur47Y10, Sur92-101 and Sur93T2, whereas in Mel.A1-1/TIL and Mel.A1-4/PBL responses were observed against Sur47Y10 and Sur93T2, respectively (FIG. 11).

In addition, ten melanoma patients were tested for immune reactivity against the native peptides Sur93-101, Sur38-46 and Sur47-56 by means of ELISPOT; however, no peptide-specific responses were detected in any of these patients (data not shown).

Identification of HLA-A11 Restricted Survivin Epitopes

Binding of Survivin-Derived Peptides to HLA-A11

The amino acid sequence of the survivin protein was screened for nonamer or deca-mer peptides with binding motifs corresponding to that of the HLA-A3 super-family, including HLA-A3 and HLA-A11. Peptide sequences with the main anchor residues, leucine (L) in position 2 and lysine (K) at the C-terminus, were chosen together with peptide sequences having related amino acids at these positions according to the predictive algorithm by Rammensee et al. (table 4).

Thirteen peptides were predicted from the protein sequence of survivin and analyzed for binding to HLA-A11 and HLA-A3. Three of these peptides, Sur53-62 (DLAQCFFCFK) (SEQ ID NO:47), Sur54-62 (LAQCFFCFK) (SEQ ID NO:42) and Sur112-120 (KIAKETNNK) (SEQ ID NO:44) bound HLA-A11 with high affinity, comparable to the viral epitope from EBV nuclear antigen 4 (AVFDRKSDAK) (SEQ ID NO:63). In addition, one peptide, Sur112-121 (KIAKETNNKK) (SEQ ID NO:51) bound weakly to HLA-A11 (Table 4).

HLA-A11 Restricted CTL Responses Against Survivin-Derived Peptides in Cancer Patients PBL from five melanoma patients and two CLL patients were tested for T-cell reactivity against the four HLA-A11 binding peptides Sur53-62; Sur54-62, Sur112-120, and Sur112-121. We were able to detect responses against the survivin-derived peptide Sur53-62 in PBL from two of the melanoma patients, Mel.A11-1, Mel.A11-2, by means of ELISPOT (FIG. 12). Additionally, we were able to detect Sur53-62 specific T-cells among tumor infiltrating lymphocytes (TIL) from a tumor infiltrated lymph node in patient Mel.A11-2 (FIG. 12). In the patient Mel.A11-1 a strong immune response against the survivin peptide Sur53-62 was observed in five different blood samples taken over a period of two years (data not shown).

Identification of HLA-A3 Restricted Survivin Epitopes

Binding of Survivin-Derived Peptides to HLA-A3

The survivin-derived peptides predicted for binding to the HLA-A3 super-family were additionally analyzed for the binding to HLA-A3. Only two of the peptides Sur112-120 (KIAKETNNK) (SEQ ID NO:44) and Sur112-121 (KIAKETNNKK) (SEQ ID NO:57) bound HLA-A3 with high affinity, similar to the viral epitope, Influenza A nucleoprotein 265-273 (ILRGSVAHK) (SEQ ID NO:74) (Table 4). Furthermore, two peptides Sur53-62 (DLAQCFFCFK) (SEQ ID NO:47) and Sur95-103 (ELTLGEFLK) (SEQ ID NO:43) bound weakly to HLA-A3.

Some of the peptides with no detectable binding were modified in an attempt to increase the binding affinity for HLA-A3. Thus, we synthesized two analogue peptides of Sur54-62 and Sur113-122 in which a better anchor residue leucine (L) replaced the natural alanine (A) at position 2. Sur54L2 (LLQCFFCFK) (SEQ ID NO:56) bound HLA-A3 with high affinity, whereas Sur113L2 (ILKETNNKKK) (SEQ ID NO:59) only bound weakly (Table 4). In addition, we synthesized four analogue peptides of Sur5-13, Sur13-22, Sur18-27, and Sur53-61 in which the better anchor residue lysine (K) replaced the natural phenylalanine (F) at the C-terminus. Sur5K9 (TLPPAWQPK) (SEQ ID NO:54) and Sur18K10 (RISTFKNWPK) (SEQ ID NO:58) bound to HLA-A3 with high affinity, whereas the substitutions had no detectable effect on the binding to HLA-A3 of Sur13K9 (FLKDHRISTK) (SEQ ID NO:57) and Sur53K9 (DLAQCFFCK) (SEQ ID NO:55) compared to the native analogues.

HLA-A3 Restricted CTL Responses Against Survivin-Derived Peptides in Cancer Patients Nine samples from melanoma patients (five PBL and four TIL) were analyzed for immune reactivity against the two native high affinity HLA-A3 binding peptides Sur112-120 and Sur112-121, as well as the two native, weak binding peptides Sur53-62 and Sur95-103. However, no immune responses against these peptides could be detected by ELISPOT in any of the patients. Subsequently, the same patients were analyzed for spontaneous immune reactivity against the three high affinity, modified survivin-derived peptides, Sur5K9, Sur18K10, and Sur54L2. CTL reactivity was detected against Sur18K10 in TIL samples from three patients, Mel.A3-1, Mel.A3-2, Mel.A3-3 (FIG. 13). No responses were detected against the two other peptides, Sur5K9 and Sur54L2. To further verify these responses, PBL from additional eighteen melanoma patients were analyzed for CTL reactivity against Sur18K10. Three responding patients, Mel.A3-4, Mel.A3-5, and Mel.A3-6, were found among these, resulting in a total of six responding patients among the twenty-seven patients analyzed (FIG. 13).

Identification of a Novel HLA-A2 Restricted Survivin Epitope

Binding of 11-Mer Survivin-Derived Peptides to HLA-A2

The amino acid sequence of the survivin protein was screened for the most probable HLA-A2 11-mer peptide epitopes, using the main HLA-A2 specific anchor residues. Six survivin deduced peptides were synthesized and examined for binding to HLA-A2. None of the peptides examined bound with similar high affinity as a known positive control epitope from Epstein-Barr virus $BMLF_{280-288}$ peptide (GLCTLVAML) (SEQ ID NO:72) (Table 4). The peptide concentration required for half maximal recovery of HLA-A2 ($C_{50}$ value) was 0.9 μM for the positive control. In comparison, the peptides Sur18-28 (RISTFKNWPFL) (SEQ ID NO:67) and Sur86-96 (FLSVKKQFEEL) (SEQ ID NO:69) bound weakly to HLA-A2 ($C_{50}$=69 μM and 72 μM respectively). However, the two known HLA-A2-restricted survivin epitopes bound in a similar way weakly to HLA-A2; Sur95-104 (ELTLGEFLKL) (SEQ ID NO:43) bound with intermediate affinity ($C_{50}$=10 μM) whereas Sur96-104 (LTLGEFLKL) (SEQ ID NO:10) bound only weakly ($C_{50}$>100 μM). The remaining four 11-mer peptides examined (Sur-4-14 (PTLPPAWQPFL) (SEQ ID NO:66), Sur54-64 (LAQCFFCFKEL) (SEQ ID NO:68), Sur88-98 (SVKKQFEELTL) (SEQ ID NO:70), and Sur103-113 (KLDRERAKNKI) (SEQ ID NO:74)) did not bind to HLA-A2.

HLA-A2 Restricted CTL Responses Against Survivin-Derived Peptides in Cancer Patients PBL from ten cancer patients (two melanoma (Mel), six CLL (CLL), and two mamma carcinoma (MC) patients) was initially analyzed to investigate whether the two weak binding 11mer peptides, Sur18-28 and Sur86-96 were presented by HLA-A2 and recognized by the immune system of cancer patients. CTL responses against Sur18-28 were found in PBL from two of the ten patients analyzed (CLL-1, CLL-2, FIG. 14), whereas no responses could be detected against Sur86-96 (data not shown). To further verify these Sur18-28 specific responses, PBL from additional twelve patients (seven melanoma, one CLL, and four mamma carcinoma patients) were analyzed for CTL reactivity against this peptide. Among these, four patients (CLL-3, MC-1, MC-2, Mel.A2-1) had Sur18-28 specific immune activity detectable by ELISPOT (FIG. 14). Thus, altogether PBL from six out of twenty-two patients analyzed hosted a CTL response against Sur18-28.

Identification of HLA-B7 Restricted Survivin Epitopes

Binding of Survivin Derived Peptides to HLA-B7

The amino acid sequence of the survivin protein was screened for peptides of nine to ten amino acids, with anchor residues according to the peptide binding motif of HLA-B7. Five peptides were selected and analyzed for their ability to stabilize HLA-B7 in the assembly assay. $C_{50}$ values were estimated for each peptide as the peptide concentration needed for half maximal stabilization of HLA-B7 (table 4). Two survivin-derived peptides, sur6-14 (LPPAWQPFL) (SEQ ID NO:18) and sur11-19 (QPFLKDHRI) (SEQ ID NO:19) stabilized HLA-B7 weakly, with $C_{50}$ values above 100 μM; whereas sur46-54 (CPTENEPDL) (SEQ ID NO:6), sur51-59 (EPDLAQCFF) (SEQ ID NO:7), and sur34-43 (TPERMAEAGF) (SEQ ID NO:20) did not bind to HLA-B7 (table 4).

HLA-B7 Restricted CTL Responses Against Survivin Derived Peptides in Cancer Patients HLA-B7 positive PBL from five melanoma patients (mel25, mel26, mel3, mel6, mel39), two CLL patients (CLL1, CLL54) and 2 breast cancer patients (breast11, breast 15) were tested for T-cell reactivity against the weak HLA-B7 binding peptides sur6-14 (LPPAWQPFL) (SEQ ID NO:18) and sur11-19 (QPFLKDHRI) (SEQ ID NO:19). We were able to detect a strong spontaneous CTL response against the survivin derived peptide sur6-14 in PBL in a CLL patient and in a breast cancer patient (FIG. 15). Additionally, we were able to detect a weak response against this peptide in the melanoma patient mel3 (FIG. 15).

Summary of HLA Allele-Restricted Immune Responses to Survivin-Derived Peptides in Cancer Patients A range of survivin-derived peptides comprising 9-11 amino acid residues were tested for binding to the following HLA alleles: HLA-A1, HLA-A3, HLA-A11 and HLA-B7 using the assembly assay for peptide binding to MHC class I molecules described in the preceding examples. In addition, several of the peptides were tested for their capacity to elicit a CTL immune response using the ELISPOT assay as also described above.

A summary of the results, including results obtained in the previous examples, are given in the below Table 4:

TABLE 4

$C_{50}$ and ELISPOT data for selected survivin-derived peptides

| HLA allele | Peptide length | Position | Sequence | $C_{50}$ (μM) | Remarks | SEQ ID NO: | Footnotes |
|---|---|---|---|---|---|---|---|
| HLA-A1 | 9 mer | Sur14-22 | LKDHRISTF | NB | | 22 | |
| | | Sur51-59 | EPDLAQCFF | NB | | 7 | |
| | | Sur38-46 | MAEAGFIHC | NB | | 23 | |
| | | Sur93-101 | FEELTLGEF | >100 | | 24 | |
| | 10 mer | Sur34-43 | TPERMAEAGF | NB | | 20 | |
| | | Sur47-56 | PTENEPDLAQ | NB | | 25 | |
| | | Sur49-58 | ENEPDLAQCF | NB | | 26 | |
| | | Sur92-101 | QFEELTLGEF | 2 | | 27 | |
| | Control peptide | C1 | VSDGGPNLY | 0.8 | | 28 | |
| | Modified peptides | sur14Y9 | LKDHRISTY | NB | | 29 | |
| | | sur51Y9 | EPDLAQCFY | | Weak binding | 9 | |
| | | sur93Y9 | FEELTLGEY | NB | | 30 | |
| | | sur92Y9 | QFEELTLGEY | NB | | 31 | |
| | | sur34Y9 | TPERMAEAGY | NB | | 32 | |
| | | sur49Y9 | ENEPDLAQCY | NB | | 33 | |
| | | Sur92T2 | QTEELTLGEF | 2 | | 34 | |
| | | Sur92S2 | QSEELTLGEF | 100 | | 35 | |
| | | Sur93T2 | FTELTLGEF | 1 | | 36 | |
| | | Sur93S2 | FSELTLGEF | 30 | | 37 | |
| | | Sur38Y9 | MAEAGFIHY | 0.8 | | 38 | |
| | | Sur47Y10 | PTENEPDLAY | 0.4 | | 39 | |
| HLA-A2 | | Sur4-14 | PTLPPAWQPFL | NB | | 66 | |
| | | Sur18-28 | RISTFKNWPFL | 69 | | 67 | |
| | | Sur54-64 | LAQCFFCFKEL | NB | | 68 | |
| | | Sur86-96 | FLSVKKQFEEL | 72 | | 69 | |
| | | Sur88-98 | SVKKQFEELTL | NB | | 70 | |
| | | Sur103-113 | KLDRERAKNKI | NB | | 71 | |
| | Control peptide | EBV,BMLF1 | GLCTLVAML | 3 | | 72 | |
| | | HIV, Pol | ILKEPVHGV | 0.2 | | 73 | |
| HLA-A3 | 9 mer | Sur 5-13 | TLPPAWQPF | NB | | 40 | |
| | | Sur 53-61 | DLAQCFFCF | NB | | 41 | |
| | | Sur 54-62 | LAQCFFCFK | NB | | 42 | |
| | | Sur 95-103 | ELTLGEFLK | >100 | | 43 | |
| | | Sur 112-120 | KIAKETNNK | 2 | | 44 | i |
| | 10 mer | Sur 13-22 | FLKDHRISTF | NB | | 45 | |
| | | Sur 18-27 | RISTFKNWPF | NB | | 46 | |
| | | Sur 53-62 | DLAQCFFCFK | 100 | | 47 | ii |
| | | Sur 84-93 | CAFLSVKKQF | NB | | 48 | |

TABLE 4 -continued $C_{50}$ and ELISPOT data for selected survivin-derived peptides

| HLA allele | Peptide length | Position | Sequence | $C_{50}$ (μM) | Remarks | SEQ ID NO: | Footnotes |
|---|---|---|---|---|---|---|---|
| | | Sur 101-110 | FLKLDRERAK | NB | | 49 | |
| | | Sur 103-112 | KLDRERAKNK | NB | | 50 | |
| | | Sur 112-121 | KIAKETNNKK | 1 | | 51 | |
| | | Sur 113-122 | IAKETNNKKK | NB | | 52 | |
| | Control peptide | C3 | ILRGSVAHK | 0.1-0.3 | | 53 | |
| | Modified peptides | Sur5K9 | TLPPAWQPK | 2 | | 54 | |
| | | Sur53K9 | DLAQCFFCK | NB | | 55 | |
| | | Sur54L2 | LLQCFFCFK | 1 | | 56 | |
| | | Sur13K9 | FLKDHRISTK | NB | | 57 | |
| | | Sur18K10 | RISTFKNWPK | 0.02 | | 58 | |
| | | Sur113L2 | ILKETNNKKK | >100 | | 59 | |
| | | SurEx3-A3-1 | TIRRKNLRK | 0.5 | | 60 | iii |
| | | SurEx3-A3-2 | PTIRRKNLRK | NB | | 61 | |
| | | Sur2b-A3-1 | RITREEHKK | NB | | 62 | |
| | Control peptide | Influenza A, nucleoprotein 265-273 | ILRGSVAHK | 0.1 | | 74 | |
| HLA-A11 | 9 mer | Sur 5-13 | TLPPAWQPF | NB | | 40 | |
| | | Sur 53-61 | DLAQCFFCF | NB | | 41 | |
| | | Sur 54-62 | LAQCFFCFK | 0.4 | | 42 | |
| | | Sur 95-103 | ELTLGEFLK | NB | | 43 | |
| | | Sur 112-120 | KIAKETNNK | 1 | | 44 | |
| | 10 mer | Sur 13-22 | FLKDHRISTF | NB | | 45 | |
| | | Sur 18-27 | RISTFKNWPF | NB | | 46 | |
| | | Sur 53-62 | DLAQCFFCFK | 5 | | 47 | |
| | | Sur 84-93 | CAFLSVKKQF | NB | | 48 | |
| | | Sur 101-110 | FLKLDRERAK | NB | | 49 | |
| | | Sur 103-112 | KLDRERAKNK | NB | | 50 | |
| | | Sur 112-121 | KIAKETNNKK | >100 | | 51 | iv |
| | | Sur 113-122 | IAKETNNKKK | NB | | 52 | |
| | Control peptide | C4 | AVFDRKSDAK | 0.2 | | 63 | |
| HLA-B7 | 9 mer | Sur 6-14 | LPPAWQPFL | >100 | | 18 | v |
| | | Sur 11-19 | QPFLKDHRI | >100 | | 19 | |
| | | Sur 46-54 | CPTENEPDL | NB | | 6 | |
| | | Sur 51-59 | EPDLAQCFF | NB | | 7 | |
| | 10 mer | Sur 34-43 | TPERMAEAGF | NB | | 20 | |
| | Control peptides | C6 | QPRAPIRPI | 0.1 | | 64 | |
| | | C7 | RPPIFIRRL | 0.5 | | 65 | |

i An response was observed against the peptide Sur112-120 in one lymphoma patient (HEM34) by means of ELISPOT.
ii Responses were detected against the peptide Sur53-62 in 3 lymphoma patients (HEM9, 11, 34) by means of ELISPOT.
iv A weak response was observed in a melanoma patient (FM-TIL95) by means of ELISPOT.
vii A response was observed against Sur112-121 in a melanoma patient (PM6), most evident in metastatic lymph-node suspension, and weaker in the TIL from primary tumor and PBL by means of ELISPOT.
viii An response against the peptide Sur6-14 was observed in a CLL patient (CLL9), and a weaker response was observed in a lymphoma patient by means of elispot (HEM 21) (data not shown.

Example 5

Therapeutic Trial Procedures Using Survivin-Derived Peptides as Immunogens

Summary

Five heavily pretreated stage IV melanoma patients were vaccinated with the modified HLA-A2-restricted survivin epitope, namely the sur1M2 peptide, presented by autologous dendritic cells in a compassionate use setting. Four of the patients mounted strong T-cell response to this epitope as measured by ELISPOT assay. Furthermore, in situ peptide/HLA-A2 multimer staining revealed the infiltration of survivin reactive cells into both visceral and soft tissue metastases. Notably, vaccination associated toxicity was not observed. The data demonstrate that it is feasible to induce T-cell response against survivin, even in late stage melanoma patients, and that these vaccinations are well tolerated.

Materials and Methods

Patient Eligibility Criteria and Treatment Regimen

All clinical procedures were in accordance with the Declaration of Helsinki and all patients provided informed consent prior to therapy. Stage IV cutaneous or uveal melanoma patients were eligible when their disease was progressive despite at least two different chemo-, immuno, or chemoimmunotherapies. In addition, a patients had to be 18 years or older, express HLAA*0201, and suffer from measurable disease validated by cranial, thoracic and abdominal computed tomography scans. Patients' Karnofsky index had to be 60% or better. No systemic chemo-, and/or immunotherapy was allowed within 4 week prior to vaccination. Important exclusion criteria were evidence of CNS metastases, active autoimmune or infectious diseases, pregnancy and lactation, as well as significant psychiatric abnormality. Peptide pulsed dendritic cells were generated as previously described (82). Briefly, PBMCs from leukapheresis were isolated on LYMPHOPREP® (density gradient medium) (Nycomed Pharma), frozen in aliquots and stored in liquid nitrogen. One week prior to vaccination, PBMCs were thawed, washed and cultured in medium containing gentamycin, glutamine and heat inactivated autologous plasma. On day 1 and 5, IL-4 and GM-CSF were added. To differentiate mature DCs, TNF-γ and prostaglandin E2 were added on day 6. On day 7, cells displaying phenotypical and morphological characteristics of mature DCs, i.e. a veiled appearance and =75% CD83 expression, were pulsed with a modified survivin-derived HLA-A2 restricted survivin$_{96-104}$ epitope, LMLGEFLKL (SEQ ID NO 10)(Clinalfa, Switzerland) 14. Cells were only used for vaccination if microbial tests of samples taken from cultures on days 1 and 5 proved to be sterile.

Patients were vaccinated at 7-day intervals for the first two vaccinations followed by 28-day intervals for further vaccinations. A total of 10-20×10$^6$ mature, survivin$_{96-104}$ pulsed DCs were resuspended in PBS, containing 1% human serum albumin, and injected intradermally in aliquots of 1.5×10$^6$ DCs per injection site in the ventromedial regions of the thighs close to the regional lymph nodes. Limbs where draining lymph nodes had been removed and/or irradiated were excluded. Leukapheresis was repeated after 5 vaccinations in absence of severe deterioration of patient's state of health or occurrence of CNS metastases.

Measurement of Clinical and Immunological Responses

CT scans were performed prior to vaccination and every three months thereafter or in case of severe clinical signs of disease progression. Immunological responses were monitored by the ELISPOT assay, using PBMCs obtained every three months, to detect survivin$_{96-104}$ specific IFN-γ release. To extend the sensitivity of the ELISPOT assay, PBMCs were stimulated once in vitro at a concentration of 1×10$^6$ cells per ml in 24-well plates (Nunc, Denmark) in X-vivo medium (Bio Whittaker, Walkersville, Md.), supplemented with 5% heat-inactivated human serum and 2 mM of L-glutamine in the presence of 10 μM of peptide. Two days later, 40 IU/ml recombinant interleukin-2 (IL-2) (Chiron, Ratingen, Germany) were added. After 10 days the cells were tested for reactivity. To this end, nitrocellulose bottomed 96-well plates (MULTISCREEN® MAIP N45 (96-well assay plate), Millipore, Glostrup, Denmark) were coated with an anti-IFN-7 antibody (1-D1K, Mabtech, Sweden). Lymphocytes were added at 10$^4$-10$^5$ cells in 200 μl X-VIVO® medium (chemically defined, serum-free media) per well together with 10$^4$ T2-cells and the relevant peptides at a final concentration of 2 μM. After an overnight incubation at 37° C. and two washes, the biotinylated detection antibody (7-B6-1-Biotin, Mabtech, Sweden) was added; its specific binding was visualised using alkaline phosphatase-avidin together with the respective substrate (GibcoBRL). The reaction was terminated upon the appearance of dark purple spots, which were quantitated using the ALPHA IMAGER® System (imaging software) (Alpha Innotech, San Leandro, Calif., USA).

Survivin96-104/HLA-A*0201 reactive CD8+ T lymphocytes were also tracked in situ both at the vaccination sites as well as in visceral, soft tissue, or cutaneous metastases by means of multimeric survivin96-104/HLA-A*0201 complexes. Vaccination sites were excised 24 h after intradermal injection in all patients, whereas metastatic lesions were only removed in selected patients, if easily accessible (patients KN and GB), or removed during a curative intent (patient WW). The staining procedure for multimeric peptide/MHC complexes has been described recently (68). The multimeric survivin96-104/HLA-A*0201 complexes were generated by introduction of a recognition site for enzymatic biotinylation at the 5' end of the extracellular domains of HLA-A*0201 (residues 1-275). The recombinant protein was purified by size-exclusion (SEPHADEX G 25® (gel filtration), Pharmacia, Erlangen, Germany) and ion exchange (MONO-Q®, Pharmacia) chromatography and folded in vitro by dilution in presence of the respective peptides and β2-microglobulin. After gel filtration on a Sephadex G25® (gel filtration) column, the protein was multimerized with streptavidin-FITC conjugated to dextran molecules (kindly provided by L. Winther, DAKO, Copenhagen, Denmark) to generate multivalent HLA-dextran complexes. Cryopreserved sections of the respective samples were dried over-night and subsequently fixed in cold acetone for 5 min. All incubation steps were performed in the dark at room temperature as follows: (i) 45 min of an anti-CD8 antibody (1:100, clone HIT8a, Pharmingen, San Diego, Calif.), (ii) Cy3-conjugated goat antimouse (1:500 diluted; code 115-165-100, Dianova, Hamburg, Germany) for 45 min and finally (iii) the multimers for 75 min. Between each step the slides were washed twice for 10 min in PBS/BSA 0.1%. Finally, slides were mounted in VECTASHIELD® (antifade mounting medium) and observed under a Leica Confocal Microscope (TCS 4D, Leica, Mannheim, Germany).

Results

Patient Characteristics, Toxicity and Clinical Course

Five far-advanced stage IV melanoma patients were enrolled, two suffering from uveal melanoma, one from soft tissue melanoma and the remaining two from cutaneous melanoma. Due to the manifestation of symptomatic brain metastases, one patient was taken off therapy after only two vaccinations. The other four patients received up to 15 vaccinations. One patient died from cardiac arrest in tumor free status after surgical resection of remaining metastases. Another patient was taken off therapy after 10 vaccinations because of appearance of visceral metastases (RW). One patient remained on study after 15 vaccinations. Detailed patient characteristics, previous therapy, number of vaccinations and survival status are summarized in table 5.

No major toxicities occurred. Thus, hemoglobin, leucocytes and thrombocytes, as well as lactate dehydrogenase, creatinine and cholinesterase were not influenced by the vaccination therapy (FIG. 16). No signs of systemic or local toxicity were observed at the injection sites. Furthermore, there was no detection of impaired wound healing, hemorrhagic disorders, cardiac dysfunction, vasculitis or inflammatory bowel disease. In one patient (WW), pre-existing liver metastases could be stabilized under vaccination therapy, but a new adrenal metastasis still occurred. Unfortunately, this patient died due to cardiac arrest, even though tumor-free after curative surgery. A brain metastasis was detected in patient PB only 4 weeks after initiation of vaccination. Therefore, this patient had to be excluded from further vaccinations after only two DC injections. The other three patients demonstrated slow progression of metastatic disease without substantial impairment in their general state of health. Remarkably, for patient KN, an overall survival of 13 months (from vaccination start to death) could be achieved despite a heavy metastatic load and fast disease progression at the start of vaccination. Patient GB remained on protocol 14 months after initiation of vaccination with survivin-peptide pulsed DCs. It should be noted, however, that both patients (RW and GB) received additional localized treatment for tumor control, either radiation of subcutaneous tumors (RW) or focal chemotherapy (GB).

Survivin-Specific CD8+ T Cell Responses

Figure 17:
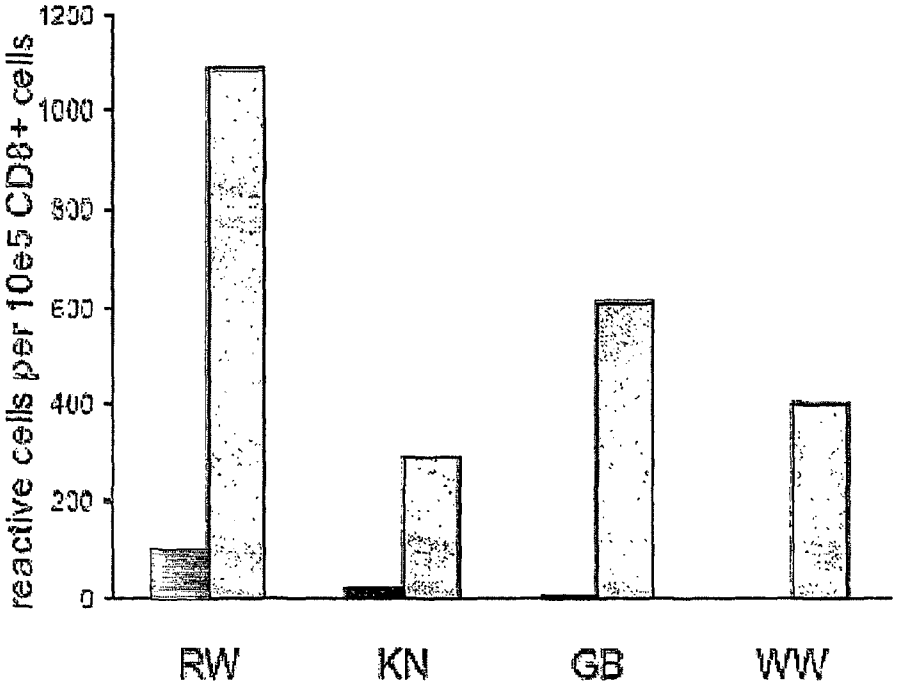

To monitor the kinetics of cytotoxic T cell responses, PBMCs obtained prior to and three months after vaccination were tested for reactivity to the modified survivin$_{96-104}$ epitope by ELISPOT for IFN-γ. Before analysis, PBMCs were stimulated once in vitro to extend the sensitivity of this assay. In all four patients tested, an induction of survivin$_{96-104}$ reactive T cells was evident (FIG. 17). Analysis for reactivity to other HLA-A*0201 restricted survivin peptides, i.e. the non-modified survivin$_{96-104}$ and the adjacent Sur9 epitope, demonstrated a T cell response against these peptides in two of the patients (KN and RW)(data not shown).

The prognostic and clinical value of measurements of tumor-specific T-cell responses in peripheral blood has been questioned repeatedly; thus, we also tested for the presence of survivin$_{96-104}$/HLA-A*0201 reactive CD8+ T lymphocytes among tumor infiltrating lymphocytes in situ by peptide/MHC multimer staining. To validate the method, we first analyzed tissue samples from delayed type hypersensitivity reactions occurring at the vaccination site within 24 hrs. This analysis confirmed earlier observations that intradermal injections of peptide-pulsed DC induce a strong peptide-specific inflammatory T-cell infiltrate. Subsequently, the peptide/MHC multimer staining procedure was applied on soft tissue and visceral metastases, which revealed the presence of survivin$_{96-104}$/HLA-A*0201 reactive cells among the CD8+ infiltrate. This observation suggests that the vaccination does not only induce T cell with the desired specificity, but also endows them with the necessary homing capacity.

REFERENCES

1. Van den Eynde, B. J. and Boon, T. Tumor antigens recognized by T lymphocytes. Int. J. Clin. Lab. Res., 27: 81-86, 1997.
2. Rosenberg, S. A. Development of cancer immunotherapies based on identification of the genes encoding cancer regression antigens. J. Natl. Cancer Inst., 20; 88: 1635-1644, 1996.
3. Marchand, M., van Baren, N., Weynants, P., Brichard, V., Dreno, B., Tessier, M. H., Rankin, E., Parmiani, G., Arienti, F., Humblet, Y., Bourlond, A., Vanwijck, R., Lienard, D., Beauduin, M., Dietrich, P. Y., Russo, V., Kerger, J., Masucci, G., Jager, E., De Greve, J., Atzpodien, J., Brasseur, F., Coulie, P. G., van der Bruggen, P., and Boon, T. Tumor regressions observed in patients with metastatic melanoma treated with an antigenic peptide encoded by gene MAGE-3 and presented by HLA-A1. Int. J. Cancer, 80: 219-230, 1999.
4. Brossart, P., Stuhler, G., Flad, T., Stevanovic, S., Rammensee, H. G., Kanz, L., and Brugger, W. Her-2/neu-derived peptides are tumor-associated antigens expressed by human renal cell and colon carcinoma lines and are recognized by in vitro induced specific cytotoxic T lymphocytes. Cancer Res., 58: 732-736, 1998.
5. Brossart, P., Heinrich, K. S., Stuhler, G., Behnke, L., Reichardt, V. L., Stevanovic, S., Muhm, A., Rammensee, H. G., Kanz, L., and Brugger, W. Identification of HLA-A2-restricted T-cell epitopes derived from the MUC1 tumor antigen for broadly applicable vaccine therapies. Blood, 93: 4309-4317, 1999.
6. Vonderheide, R. H., Hahn, W. C., Schultze, J. L., and Nadler, L. M. The telomerase catalytic subunit is a widely

TABLE 5

Summary of vaccination trials: patient characteristics

| Patient ID | Age/ Sex | Time from primary tumor to stage IV | Previous therapy | Measurable disease | Clinical outcome | No. of vaccinations | Survival after first vaccination* |
|---|---|---|---|---|---|---|---|
| GB | 40/female | 4 years, 8 months | LITT, fotemusine/IL-2IFNα, treosulfan/gemcitabine | liver | PD (slow growth of pre-existing and new hepatic lesions, new pancreas and pleural metastases) | 15 | +14 months |
| KN | 53/male | 11 years | IL-2IFNα/histamine, fotemustine, treosulfan/gemcitabine | liver, kidney, soft tissue, bone | PD (slow growth of pre-existing lesions, new lymph node, pleural and mediastinal lesions) | 13 | 13 months |
| WW | 73/male | 14 months | surgery, DC-vaccination, decarbazine | liver | PD (stable hepatic, but new adrenal metastasis) | 12 | 12 months due post-surgical stroke |
| RW | 72/male | 16 years | surgery, radiotherapy, adriblastin/ifosfamid, ixoten, decarbazine, TNF/melphalan | soft tissue | PD (growth of pre-existing and new soft tissue metastases; detection of heart, lung and muscle metastases after 12 vaccinations) | 12 | +12 months |
| PB | 52/male | 2 years, 3 months | radiotherapy | lung, kidney | PD (new skin and brain metastases) | 2 | 4 months |

expressed tumor-associated antigen recognized by cytotoxic T lymphocytes. Immunity., 10: 673-679, 1999.

7. LaCasse, E. C., Baird, S., Korneluk, R. G., and MacKenzie, A. E. The inhibitors of apoptosis (IAPs) and their emerging role in cancer. Oncogene, 17: 3247-3259, 1998.
8. Altieri, D. C., Marchisio, P. C., and Marchisio, C. Survivin apoptosis: an interloper between cell death and cell proliferation in cancer. Lab Invest, 79: 1327-1333, 1999.
9. Ambrosini, G., Adida, C., Sirugo, G., and Altieri, D. C. Induction of apoptosis and inhibition of cell proliferation by survivin gene targeting. J. Biol. Chem., 273: 11177-11182, 1998.
10. Grossman, D., McNiff, J. M., Li, F., and Altieri, D. C. Expression and targeting of the apoptosis inhibitor, survivin, in human melanoma. J. Invest Dermatol., 113: 1076-1081, 1999.
11. Grossman, D., McNiff, J. M., Li, F., and Altieri, D. C. Expression of the apoptosis inhibitor, survivin, in nonmelanoma skin cancer and gene targeting in a keratinocyte cell line. Lab Invest, 79: 1121-1126, 1999.
12. Andersen, M. H., Sondergaard, I., Zeuthen, J., Elliott, T., and Haurum, J. S. An assay for peptide binding to HLA-Cw*0102. Tissue Antigens., 54: 185-190, 1999.
13. Andersen, M. H., Bonfill, J. E., Neisig, A., Arsequell, G., ndergaard, I., Neefjes, J., Zeuthen, J., Elliott, T., and Haurum, J. S. Phosphorylated Peptides Can Be Transported by TAP Molecules, Presented by Class I MHC Molecules, and Recognized by Phosphopeptide-Specific CTL. J. Immunol., 163: 3812-3818, 1999.
14. McCutcheon, M., Wehner, N., Wensky, A., Kushner, M., Doan, S., Hsiao, L., Calabresi, P., Ha, T., Tran, T. V., Tate, K. M., Winkelhake, J., and Spack, E. G. A sensitive ELISPOT assay to detect low-frequency human T lymphocytes. J. Immunol. Methods, 210: 149-166, 1997.
15. Pass, H. A., Schwarz, S. L., Wunderlich, J. R., and Rosenberg, S. A. Immunization of patients with melanoma peptide vaccines: immunologic assessment using the ELISPOT assay. Cancer J. Sci. Am., 4: 316-323, 1998.
16. Berke, Z., Andersen, M. H., Pedersen, M., Fugger, L., Zeuthen, J., and Haurum, J. S. Peptides spanning the junctional region of both the abl/bcr and the bcr/abl fusion proteins bind common HLA class I molecules. Leukemia, 14: 419-426, 2000.
17. Falk, K., Rotzschke, O., Stevanovic, S., Jung, G., and Rammensee, H. G. Allele-specific motifs revealed by sequencing of self-peptides eluted from MHC molecules. Nature, 351: 290-296, 1991.
18. Cornelison, T. L. Human papiliomavirus genotype 16 vaccines for cervical cancer prophylaxis and treatment. Curr. Opin. Oncol., 12: 466-473, 2000.
19. Lee, S. P., Chan, A. T., Cheung, S. T., Thomas, W. A., CroomCarter, D., Dawson, C. W., Tsai, C. H., Leung, S. F., Johnson, P. J., and Huang, D. P. CTL control of EBV in nasopharyngeal carcinoma (NPC): EBV-specific CTL responses in the blood and tumors of NPC patients and the antigen-processing function of the tumor cells. J. Immunol., 165: 573-582, 2000.
20. Swana, H. S., Grossman, D., Anthony, J. N., Weiss, R. M., and Altieri, D. C. Tumor content of the antiapoptosis molecule survivin and recurrence of bladder cancer. N. Engl. J. Med., 341: 452-453, 1999.
21. Salgaller, M. L., Afshar, A., Marincola, F. M., Rivoltini, L., Kawakami, Y., and Rosenberg, S. A. Recognition of multiple epitopes in the human melanoma antigen gp100 by peripheral blood lymphocytes stimulated in vitro with synthetic peptides. Cancer Res., 55: 4972-4979, 1995.
22. Salgaller, M. L., Marincola, F. M., Cormier, J. N., and Rosenberg, S. A. Immunization against epitopes in the human melanoma antigen gp100 following patient immunization with synthetic peptides. Cancer Res., 56: 4749-4757, 1996.
23. Valmori, D., Fonteneau, J. F., Lizana, C. M., Gervois, N., Lienard, D., Rimoldi, D., Jongeneel, V., Jotereau, F., Cerottini, J. C., and Romero, P. Enhanced generation of specific tumor-reactive CTL in vitro by selected Melan-A/MART-1 immunodominant peptide analogues. J. Immunol., 160: 1750-1758, 1998.
24. Pardoll, D. M. Cancer vaccines. Nat. Med., 4: 525-531, 1998.
25. Kugler, A., Stuhler, G., Walden, P., Zoller, G., Zobywalski, A., Brossart, P., Trefzer, U., Ullrich, S., Muller, C. A., Becker, V., Gross, A. J., Hemmerlein, B., Kanz, L., Muller, G. A., and Ringert, R. H. Regression of human metastatic renal cell carcinoma after vaccination with tumor cell-dendritic cell hybrids. Nat. Med., 6: 332-336, 2000.
26. Becker, J. C., Guldberg, P., Zeuthen, J., Bröcker, E. B., and thor Straten, P. Accumulation of identical T cells in melanoma and vitiligo-like leukoderma. J. Invest. Dermatol., 113: 1033-1038, 1999.
27. Rohayem, J., Diestelkoetter, P., Weigle, B., Oehmichen, A., Schmitz, M., Mehlhorn, J., Conrad, K., and Rieber, E. P. Antibody response to the tumor-associated inhibitor of apoptosis protein survivin in cancer patients. Cancer Res. 2000. Apr. 1; 60.(7.):1815.-7., 60: 1815-1817.
28. Adida, C., Haioun, C., Gaulard, P., Lepage, E., Morel, P., Briere, J., Dombret, H., Reyes, F., Diebold, J., Gisselbrecht, C., Salles, G., Altieri, D. C., and Molina, T. J. Prognostic significance of survivin expression in diffuse large B-cell lymphomas. Blood, 96: 1921-1925, 2000.
29. Islam, A., Kageyama, H., Takada, N., Kawamoto, T., Takayasu, H., Isogai, E., Ohira, M., Hashizume, K., Kobayashi, H., Kaneko, Y., and Nakagawara, A. High expression of Survivin, mapped to 17q25, is significantly associated with poor prognostic factors and promotes cell survival in human neuroblastoma. Oncogene, 19: 617-623, 2000.
30. Kawasaki, H., Altieri, D. C., Lu, C. D., Toyoda, M., Tenjo, T., and Tanigawa, N. Inhibition of apoptosis by survivin predicts shorter survival rates in colorectal cancer. Cancer Res., 58: 5071-5074, 1998.
31. Schmitz, M., Diestelkoetter, P., Weigle, B., Schmachtenberg, F., Stevanovic, S., Ockert, D., Rammensee, H. G., and Rieber, E. P. Generation of survivin-specific CD8+ T effector cells by dendritic cells pulsed with protein or selected peptides. Cancer Res., 60: 4845-4849, 2000.
32. Andersen, M. H., Pedersen, L. O., Becker, J. C., and thor Straten, P. Identification of a Cytotoxic T Lymphocyte Response to the Apoptose Inhibitor Protein Survivin in Cancer Patients. Cancer Res., 61: 869-872, 2001.
33. Lee, K. H., Panelli, M. C., Kim, C. J., Riker, A. I., Bettinotti, M. P., Roden, M. M., Fetsch, P., Abati, A., Rosenberg, S. A., and Marincola, F. M. Functional dissociation between local and systemic immune response during anti-melanoma peptide vaccination. J. Immunol., 161: 4183-4194, 1998.
34. Rosenberg, S. A., Yang, J. C., Schwartzentruber, D. J., Hwu, P., Marincola, F. M., Topalian, S. L., Restifo, N. P., Dudley, M. E., Schwarz, S. L., Spiess, P. J., Wunderlich, J. R., Parkhurst, M. R., Kawakami, Y., Seipp, C. A., Einhorn, J. H., and White, D. E. Immunologic and therapeutic evaluation of a synthetic peptide vaccine for the treatment of patients with metastatic melanoma. Nat. Med., 4: 321-327, 1998.

35. Altman, J. D., Moss, P. A., Goulder, P. J. R., Barouch, D. H., McHeyzer Williams, M. G., Bell, J. I., McMichael, A. J., and Davis, M. M. Phenotypic analysis of antigen-specific T lymphocytes. Science, 274: 94-96, 1996.
36. Schrama, D., Andersen, M. H., Terheyden, P., Schroder, L., Pedersen, L. O., thor Straten, P., and Becker, J. C. Oligoclonal T-Cell Receptor Usage Of Melanocyte Differentiation Antigen-reactive T Cells in Stage IV Melanoma Patients. Cancer Res., 61: 493-496, 2001.
37. Luxembourg, A. T., Borrow, P., Teyton, L., Brunmark, A. B., Peterson, P. A., and Jackson, M. R. Biomagnetic isolation of antigen-specific CD8+ T cells usable in immunotherapy. Nat. Biotechnol., 16: 281-285, 1998.
38. Kirkin, A. F., Reichert Petersen, T., Olsen, A. C., Li, L., thor Straten, P., and Zeuthen, J. Generation of human-melanoma specific T lymphocyte clones defining novel cytolytic targets with panels of newly established melanoma cell lines. Cancer Immunol. Immunother., 41: 71-81, 1995.
39. Scheibenbogen, C., Lee, K. H., Mayer, S., Stevanovic, S., Moebius, U., Herr, W., Rammensee, H. G., and Keilholz, U. A sensitive ELISPOT assay for detection of CD8+ T lymphocytes specific for HLA class I-binding peptide epitopes derived from influenza proteins in the blood of healthy donors and melanoma patients. Clin. Cancer Res., 3: 221-226, 1997.
40. thor Straten, P., Guldberg, P., Grønbk, K., Zeuthen, J., and Becker, J. C. In Situ T-Cell Responses against Melanoma Comprise High Numbers of Locally Expanded T-Cell Clonotypes. J. Immunol., 163: 443-447, 1999.
41. Kessler, J. H., Beekman, N. J., Bres-Vloemans, S. A., Verdijk, P., van Veelen, P. A., Kloosterman-Joosten, A. M., Vissers, D. C., ten Bosch, G. J., Kester, M. G., Sijts, A., Wouter, D. J., Ossendorp, F., Offring a, R., and Melief, C. J. Efficient identification of novel HLA-A(*)0201-presented cytotoxic T lymphocyte epitopes in the widely expressed tumor antigen PRAME by proteasome-mediated digestion analysis. J. Exp. Med., 193: 73-88, 2001.
42. de Vries, T. J., Fourkour, A., Wobbes, T., Verkroost, G., Ruiter, D. J., and van Muijen, G. N. Heterogeneous expression of immunotherapy candidate proteins gp100, MART-1, and tyrosinase in human melanoma cell lines and in human melanocytic lesions. Cancer Res., 57: 3223-3229, 1997.
43. Jager, E., Ringhoffer, M., Karbach, J., Arand, M., Oesch, F., and Knuth, A. Inverse relationship of melanocyte differentiation antigen expression in melanoma tissues and CD8+ cytotoxic-T-cell responses: evidence for immunoselection of antigen-loss variants in vivo. Int. J. Cancer, 66: 470-476, 1996.
44. Cormier, J. N., Abati, A., Fetsch, P., Hijazi, Y. M., Rosenberg, S. A., Marincola, F. M., and Topalian, S. L. Comparative analysis of the in vivo expression of tyrosinase, MART-1/Melan-A, and gp100 in metastatic melanoma lesions: implications for immunotherapy. J. Immunother., 21: 27-31, 1998.
45. Riker, A., Cormier, J., Panelli, M., Kammula, U., Wang, E., Abati, A., Fetsch, P., Lee, K. H., Steinberg, S., Rosenberg, S., and Marincola, F. Immune selection after antigen-specific immunotherapy of melanoma. Surgery, 126: 112-120, 1999.
46. Maeurer, M. J., Gollin, S. M., Martin, D., Swaney, W., Bryant, J., Castelli, C., Robbins, P., Parmlani, G., Storkus, W. J., and Lotze, M. T. Tumor escape from immune recognition: lethal recurrent melanoma in a patient associated with downregulation of the peptide transporter protein TAP-1 and loss of expression of the immunodominant MART-1/Melan-A antigen. J. Clin. Invest, 98: 1633-1641, 1996.
47. Grossman, D., Kim, P. J., Schechner, J. S., and Altieri, D. C. Inhibition of melanoma tumor growth in vivo by survivin targeting. Proc. Natl. Acad. Sci. U.S.A, 98: 635-640, 2001.
48. Tamm, I., Wang, Y., Sausville, E., Scudiero, D. A., Vigna, N., Oltersdorf, T., and Reed, J. C. IAP-family protein survivin inhibits caspase activity and apoptosis induced by Fas (CD95), Bax, caspases, and anticancer drugs. Cancer Res., 58: 5315-5320, 1998.
49. Monzo, M., Rosell, R., Felip, E., Astudillo, J., Sanchez, J. J., Maestre, J., Martin, C., Font, A., Barnadas, A., and Abad, A. A novel anti-apoptosis gene: Re-expression of survivin messenger RNA as a prognosis marker in non-small-cell lung cancers. J. Clin. Oncol., 17: 2100-2104, 1999.
50. Nakagawara, A. Molecular basis of spontaneous regression of neuroblastoma: role of neurotrophic signals and genetic abnormalities. Hum. Cell, 11: 115-124, 1998.
51. Renkvist, N., Castelli, C., Robbins, P. F., and Parmiani, G. A listing of human tumor antigens recognized by T cells. Cancer Immunol Immunother., 50: 3-15, 2001.
52. Melief, C. J., Toes, R. E., Medema, J. P., van der Burg, S. H., Ossendorp, F., and Offringa, R. Strategies for immunotherapy of cancer. Adv. Immunol., 75:235-82.: 235-282, 2000.
53. Gilboa, E. The makings of a tumor rejection antigen. Immunity., 11: 263-270, 1999.
54. Li, F., Ambrosini, G., Chu, E. Y., Plescia, J., Tognin, S., Marchisio, P. C., and Altieri, D. C. Control of apoptosis and mitotic spindle checkpoint by survivin. Nature, 396: 580-584, 1998.
55. Zaffaroni, N. and Daidone, M. G. Survivin expression and resistance to anticancer treatments: perspectives for new therapeutic interventions. Drug Resist. Updat., 5: 65-72, 2002.
56. Shinozawa, I., Inokuchi, K., Wakabayashi, I., and Dan, K. Disturbed expression of the anti-apoptosis gene, survivin, and EPR-1 in hematological malignancies. Leuk. Res, 24: 965-970, 2000.
57. Granziero, L., Ghia, P., Circosta, P., Gottardi, D., Strola, G., Geuna, M., Montagna, L., Piccoli, P., Chilosi, M., and Caligaris-Cappio, F. Survivin is expressed on CD40 stimulation and Interfaces proliferation and apoptosis in B-cell chronic lymphocytic leukemia. Blood, 97: 2777-2783, 2001.
58. Ambrosini, G., Adida, C., and Altieri, D. C. A novel anti-apoptosis gene, survivin, expressed in cancer and lymphoma. Nat. Med., 3: 917-921, 1997.
59. Altieri, D. C. Validating survivin as a cancer therapeutic target. Nat. Rev. Cancer, 3: 46-54, 2003.
60. Olie, R. A., Simoes-Wust, A. P., Baumann, B., Leech, S. H., Fabbro, D., Stahel, R. A., and Zangemeister-Wittke, U. A novel antisense oligonucleotide targeting survivin expression induces apoptosis and sensitizes lung cancer cells to chemotherapy. Cancer Res, 60: 2805-2809, 2000.
61. Andersen, M. H. and thor Straten, P. Survivin—a universal tumor antigen. Histol. Histopathol., 17: 669-675, 2002.
62. Andersen, M. H., Pedersen, L. O., Capeller, B., Bröcker, E. B., Becker, J. C., and thor, S. P. Spontaneous cytotoxic T-cell responses against survivin-derived MHC class I-restricted T-cell epitopes in situ as well as ex vivo in cancer patients. Cancer Res, 61: 5964-5968, 2001.

63. Currier, J. R., Kuta, E. G., Turk, E., Earhart, L. B., Loomis-Price, L., Janetzki, S., Ferrari, G., Birx, D. L., and Cox, J. H. A panel of MHC class I restricted viral peptides for use as a quality control for vaccine trial ELISPOT assays. J. Immunol. Methods, 260: 157-172, 2002.
64. Elvin, J., Potter, C., Elliott, T., Cerundolo, V., and Townsend, A. A method to quantify binding of unlabeled peptides to class I MHC molecules and detect their allele specificity. J Immunol Methods, 158: 161-171, 1993.
65. Ruppert, J., Sidney, J., Cells, E., Kubo, R. T., Grey, H. M., and Sette, A. Prominent role of secondary anchor residues in peptide binding to HLA-A2.1 molecules. Cell, 74: 929-937, 1993.
66. thor Straten, P., Barfoed, A., Seremet, T., Saeterdal, I., Zeuthen, J., and Guldberg, P. Detection and characterization of alpha-beta-T-cell clonality by denaturing gradient gel electrophoresis (DGGE). Biotechniques, 25: 244-250, 1998.
67. Rammensee, H., Bachmann, J., Emmerich, N. P., Bachor, O. A., and Stevanovic, S. SYFPEITHI: database for MHC ligands and peptide motifs. Immunogenetics, 50: 213-219, 1999.
68. Schrama, D., Pedersen Ls, L. O., Keikavoussi, P., Andersen, M. H., Straten, P. P., Brocker, E. B., Kampgen, E., and Becker, J. C. Aggregation of antigen-specific T cells at the inoculation site of mature dendritic cells. J. Invest Dermatol., 119: 1443-1448, 2002.
69. Mahotka, C., Wenzel, M., Springer, E., Gabbert, H. E., and Gerharz, C. D. Survivin-deltaEx3 and survivin-2B: two novel splice variants of the apoptosis Inhibitor survivin with different antiapoptotic properties. Cancer Res., 59: 6097-6102, 1999.
70. Hicklin, D. J., Marincola, F. M., and Ferrone, S. HLA class I antigen downregulation in human cancers: T-cell immunotherapy revives an old story. Mol. Med. Today, 5: 178-186, 1999.
71. Seliger, B., Cabrera, T., Gamido, F., and Ferrone, S. HLA class I antigen abnormalities and immune escape by malignant cells. Semin. Cancer Biol., 12: 3-13, 2002.
72. Sette, A., Vitiello, A., Reherman, B., Fowler, P., Nayersina, R., Kast, W. M., Melief, C. J., Oseroff, C., Yuan, L., Ruppert, J., and. The relationship between class I binding affinity and immunogenicity of potential cytotoxic T cell epitopes. J. Immunol., 153: 5586-5592, 1994.
73. Moudgil, K. D. and Sercarz, E. E. Can antitumor immune responses discriminate between self and nonself? Immunol. Today, 15: 353-355, 1994.
74. Parkhurst, M. R., Salgaller, M. L., Southwood, S., Robbins, P. F., Sette, A., Rosenberg, S. A., and Kawakami, Y. Improved induction of melanoma-reactive CTL with peptides from the melanoma antigen gp100 modified at HLA-A*0201-binding residues. J. Immunol., 157: 2539-2548, 1996.
75. Guichard, G., Zerbib, A., Le Gal, F. A., Hoebeke, J., Connan, F., Choppin, J., Briand, J. P., and Guillet, J. G. Melanoma peptide MART-1(27-35) analogues with enhanced binding capacity to the human class I histocompatibility molecule HLA-A2 by introduction of a beta-amino acid residue: implications for recognition by tumor-infiltrating lymphocytes. J. Med. Chem., 43: 3803-3808, 2000.
76. Clay, T. M., Custer, M. C., McKee, M. D., Parkhurst, M., Robbins, P. F., Kerstann, K., Wunderlich, J., Rosenberg, S. A., and Nishimura, M. I. Changes in the fine specificity of gp100(209-217)-reactive T cells in patients following vaccination with a peptide modified at an HLA-A2.1 anchor residue. J. Immunol., 162: 1749-1755, 1999.
77. Melief, C. J., van der Burg, S. H., Toes, R. E., Ossendorp, F., and Offring a, R. Effective therapeutic anticancer vaccines based on precision guiding of cytolytic T lymphocytes. Immunol. Rev., 188: 177-182, 2002.
78. Jager, E., Ringhoffer, M., Altmannsberger, M., Arand, M., Karbach, J., Jager, D., Oesch, F., and Knuth, A. Immunoselection in vivo: independent loss of MHC class I and melanocyte differentiation antigen expression in metastatic melanoma. Int. J. Cancer, 71: 142-147, 1997.
79. Thurner, B., Haendle, I., Roder, C., Dieckmann, D., Keikavoussi, P., Jonuleit, H., Bender, A., Maczek, C., Schreiner, D., von den, D. P., Brocker, E. B., Steinman, R. M., Enk, A., Kampgen, E., and Schuler, G. Vaccination with mage-3A1 peptide-pulsed mature, monocyte-derived dendritic cells expands specific cytotoxic T cells and induces regression of some metastases in advanced stage IV melanoma. J. Exp. Med., 190: 1669-1678, 1999.
80. Yee, C., Thompson, J. A., Roche, P., Byrd, D. R., Lee, P. P., Piepkorn, M., Kenyon, K., Davis, M. M., Riddell, S. R., and Greenberg, P. D. Melanocyte destruction after antigen-specific immunotherapy of melanoma: direct evidence of t cell-mediated vitiligo. J. Exp. Med., 192: 1637-1644, 2000.
81. Simon, R. M., Steinberg, S. M., Hamilton, M., Hildesheim, A., Khleif, S., Kwak, L. W., Mackall, C. L., Schlom, J., Topalian, S. L., and Berzofsky, J. A. Clinical trial designs for the early clinical development of therapeutic cancer vaccines. J. Clin. Oncol., 19: 1848-1854, 2001.

SEQUENCE LISTING

```
<160> NUMBER OF SEQ ID NOS: 89

<210> SEQ ID NO 1
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 1

Phe Leu Lys Leu Asp Arg Glu Arg Ala
1               5


<210> SEQ ID NO 2
```

<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 2

Thr Leu Pro Pro Ala Trp Gln Pro Phe Leu
1 5 10

<210> SEQ ID NO 3
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 3

Glu Leu Thr Leu Gly Glu Phe Leu Lys Leu
1 5 10

<210> SEQ ID NO 4
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 4

Leu Leu Leu Gly Glu Phe Leu Lys Leu
1 5

<210> SEQ ID NO 5
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 5

Leu Met Leu Gly Glu Phe Leu Lys Leu
1 5

<210> SEQ ID NO 6
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 6

Cys Pro Thr Glu Asn Glu Pro Asp Leu
1 5

<210> SEQ ID NO 7
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 7

Glu Pro Asp Leu Ala Gln Cys Phe Phe
1 5

<210> SEQ ID NO 8
<211> LENGTH: 9

<212> TYPE: PRT
<213> ORGANISM: Artificial Sequence
<220> FEATURE:
<223> OTHER INFORMATION: Sur53K9 peptide

<400> SEQUENCE: 8

Cys Pro Thr Glu Asn Glu Pro Asp Tyr
1 5

<210> SEQ ID NO 9
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 9

Glu Pro Asp Leu Ala Gln Cys Phe Tyr
1 5

<210> SEQ ID NO 10
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 10

Leu Thr Leu Gly Glu Phe Leu Lys Leu
1 5

<210> SEQ ID NO 11
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 11

Ile Leu Lys Glu Pro Val His Gly Val
1 5

<210> SEQ ID NO 12
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 12

Arg Ala Ile Glu Gln Leu Ala Ala Met
1 5

<210> SEQ ID NO 13
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 13

Lys Val Arg Arg Ala Ile Glu Gln Leu
1 5

<210> SEQ ID NO 14
<211> LENGTH: 9
<212> TYPE: PRT

<213> ORGANISM: Artificial Sequence
<220> FEATURE:
<223> OTHER INFORMATION: Sur53K9 peptide

<400> SEQUENCE: 14

Ser Thr Phe Lys Asn Trp Pro Phe Leu
1 5

<210> SEQ ID NO 15
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 15

Ser Val Lys Lys Gln Phe Glu Glu Leu
1 5

<210> SEQ ID NO 16
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 16

Thr Ala Lys Lys Val Arg Arg Ala Ile
1 5

<210> SEQ ID NO 17
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 17

Glu Thr Ala Lys Lys Val Arg Arg Ala Ile
1 5 10

<210> SEQ ID NO 18
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 18

Leu Pro Pro Ala Trp Gln Pro Phe Leu
1 5

<210> SEQ ID NO 19
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 19

Gln Pro Phe Leu Lys Asp His Arg Ile
1 5

<210> SEQ ID NO 20
<211> LENGTH: 10
<212> TYPE: PRT
<213> ORGANISM: Artificial Sequence <220> FEATURE:
<223> OTHER INFORMATION: Sur53K9 peptide

<400> SEQUENCE: 20

Thr Pro Glu Arg Met Ala Glu Ala Gly Phe
1 5 10

<210> SEQ ID NO 21
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 21

Tyr Pro Leu His Glu Gln His Gln Met
1 5

<210> SEQ ID NO 22
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 22

Leu Lys Asp His Arg Ile Ser Thr Phe
1 5

<210> SEQ ID NO 23
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 23

Met Ala Glu Ala Gly Phe Ile His Cys
1 5

<210> SEQ ID NO 24
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 24

Phe Glu Glu Leu Thr Leu Gly Glu Phe
1 5

<210> SEQ ID NO 25
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 25

Pro Thr Glu Asn Glu Pro Asp Leu Ala Gln
1 5 10

<210> SEQ ID NO 26
<211> LENGTH: 10
<212> TYPE: PRT
<213> ORGANISM: Artificial Sequence
<220> FEATURE:

<223> OTHER INFORMATION: Sur53K9 peptide

<400> SEQUENCE: 26

Glu Asn Glu Pro Asp Leu Ala Gln Cys Phe
1 5 10

<210> SEQ ID NO 27
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 27

Gln Phe Glu Glu Leu Thr Leu Gly Glu Phe
1 5 10

<210> SEQ ID NO 28
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 28

Val Ser Asp Gly Gly Pro Asn Leu Tyr
1 5

<210> SEQ ID NO 29
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 29

Leu Lys Asp His Arg Ile Ser Thr Tyr
1 5

<210> SEQ ID NO 30
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 30

Phe Glu Glu Leu Thr Leu Gly Glu Tyr
1 5

<210> SEQ ID NO 31
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 31

Gln Phe Glu Glu Leu Thr Leu Gly Glu Tyr
1 5 10

<210> SEQ ID NO 32
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 32

Thr Pro Glu Arg Met Ala Glu Ala Gly Tyr
1 5 10

<210> SEQ ID NO 33
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 33

Glu Asn Glu Pro Asp Leu Ala Gln Cys Tyr
1 5 10

<210> SEQ ID NO 34
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 34

Gln Thr Glu Glu Leu Thr Leu Gly Glu Phe
1 5 10

<210> SEQ ID NO 35
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 35

Gln Ser Glu Glu Leu Thr Leu Gly Glu Phe
1 5 10

<210> SEQ ID NO 36
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 36

Phe Thr Glu Leu Thr Leu Gly Glu Phe
1 5

<210> SEQ ID NO 37
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 37

Phe Ser Glu Leu Thr Leu Gly Glu Phe
1 5

<210> SEQ ID NO 38
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 38

Met Ala Glu Ala Gly Phe Ile His Tyr
1 5

<210> SEQ ID NO 39
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 39

Pro Thr Glu Asn Glu Pro Asp Leu Ala Tyr
1 5 10

<210> SEQ ID NO 40
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 40

Thr Leu Pro Pro Ala Trp Gln Pro Phe
1 5

<210> SEQ ID NO 41
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 41

Asp Leu Ala Gln Cys Phe Phe Cys Phe
1 5

<210> SEQ ID NO 42
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 42

Leu Ala Gln Cys Phe Phe Cys Phe Lys
1 5

<210> SEQ ID NO 43
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 43

Glu Leu Thr Leu Gly Glu Phe Leu Lys
1 5

<210> SEQ ID NO 44
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 44

Lys Ile Ala Lys Glu Thr Asn Asn Lys
1 5

<210> SEQ ID NO 45
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 45

Phe Leu Lys Asp His Arg Ile Ser Thr Phe
1 5 10

<210> SEQ ID NO 46
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 46

Arg Ile Ser Thr Phe Lys Asn Trp Pro Phe
1 5 10

<210> SEQ ID NO 47
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 47

Asp Leu Ala Gln Cys Phe Phe Cys Phe Lys
1 5 10

<210> SEQ ID NO 48
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 48

Cys Ala Phe Leu Ser Val Lys Lys Gln Phe
1 5 10

<210> SEQ ID NO 49
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 49

Phe Leu Lys Leu Asp Arg Glu Arg Ala Lys
1 5 10

<210> SEQ ID NO 50
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 50

Lys Leu Asp Arg Glu Arg Ala Lys Asn Lys
1 5 10

<210> SEQ ID NO 51
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 51

Lys Ile Ala Lys Glu Thr Asn Asn Lys Lys
1 5 10

<210> SEQ ID NO 52
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 52

Ile Ala Lys Glu Thr Asn Asn Lys Lys Lys
1 5 10

<210> SEQ ID NO 53
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 53

Ile Leu Arg Gly Ser Val Ala His Lys
1 5

<210> SEQ ID NO 54
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 54

Thr Leu Pro Pro Ala Trp Gln Pro Lys
1 5

<210> SEQ ID NO 55
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 55

Asp Leu Ala Gln Cys Phe Phe Cys Lys
1 5

<210> SEQ ID NO 56
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 56

Leu Leu Gln Cys Phe Phe Cys Phe Lys 1 5

<210> SEQ ID NO 57
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 57

Phe Leu Lys Asp His Arg Ile Ser Thr Lys
1 5 10

<210> SEQ ID NO 58
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 58

Arg Ile Ser Thr Phe Lys Asn Trp Pro Lys
1 5 10

<210> SEQ ID NO 59
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 59

Ile Leu Lys Glu Thr Asn Asn Lys Lys Lys
1 5 10

<210> SEQ ID NO 60
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 60

Thr Ile Arg Arg Lys Asn Leu Arg Lys
1 5

<210> SEQ ID NO 61
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 61

Pro Thr Ile Arg Arg Lys Asn Leu Arg Lys
1 5 10

<210> SEQ ID NO 62
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 62

Arg Ile Thr Arg Glu Glu His Lys Lys
1 5

<210> SEQ ID NO 63
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 63

Ala Val Phe Asp Arg Lys Ser Asp Ala Lys
1 5 10

<210> SEQ ID NO 64
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 64

Gln Pro Arg Ala Pro Ile Arg Pro Ile
1 5

<210> SEQ ID NO 65
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 65

Arg Pro Pro Ile Phe Ile Arg Arg Leu
1 5

<210> SEQ ID NO 66
<211> LENGTH: 11
<212> TYPE: PRT
<213> ORGANISM: Artificial Sequence
<220> FEATURE:
<223> OTHER INFORMATION: Sur53K9 peptide

<400> SEQUENCE: 66

Pro Thr Leu Pro Pro Ala Trp Gln Pro Phe Leu
1 5 10

<210> SEQ ID NO 67
<211> LENGTH: 11
<212> TYPE: PRT
<213> ORGANISM: Artificial Sequence
<220> FEATURE:
<223> OTHER INFORMATION: Sur53K9 peptide

<400> SEQUENCE: 67

Arg Ile Ser Thr Phe Lys Asn Trp Pro Phe Leu
1 5 10

<210> SEQ ID NO 68
<211> LENGTH: 11
<212> TYPE: PRT
<213> ORGANISM: Artificial Sequence
<220> FEATURE:
<223> OTHER INFORMATION: Sur53K9 peptide

<400> SEQUENCE: 68

Leu Ala Gln Cys Phe Phe Cys Phe Lys Glu Leu
1 5 10

<210> SEQ ID NO 69
<211> LENGTH: 11
<212> TYPE: PRT
<213> ORGANISM: Artificial Sequence
<220> FEATURE:
<223> OTHER INFORMATION: Sur53K9 peptide

<400> SEQUENCE: 69

Phe Leu Ser Val Lys Lys Gln Phe Glu Glu Leu
1 5 10

<210> SEQ ID NO 70
<211> LENGTH: 11
<212> TYPE: PRT
<213> ORGANISM: Artificial Sequence
<220> FEATURE:
<223> OTHER INFORMATION: Sur53K9 peptide

<400> SEQUENCE: 70

Ser Val Lys Lys Gln Phe Glu Glu Leu Thr Leu
1 5 10

<210> SEQ ID NO 71
<211> LENGTH: 11
<212> TYPE: PRT
<213> ORGANISM: Artificial Sequence
<220> FEATURE:
<223> OTHER INFORMATION: Sur53K9 peptide

<400> SEQUENCE: 71

Lys Leu Asp Arg Glu Arg Ala Lys Asn Lys Ile
1 5 10

<210> SEQ ID NO 72
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 72

Gly Leu Cys Thr Leu Val Ala Met Leu
1 5

<210> SEQ ID NO 73
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 73

Ile Leu Lys Glu Pro Val His Gly Val
1 5

<210> SEQ ID NO 74
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 74

Ile Leu Arg Gly Ser Val Ala His Lys
1 5

<210> SEQ ID NO 75
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 75

Arg Leu Gln Glu Glu Arg Thr Cys Lys Val
1 5 10

<210> SEQ ID NO 76
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 76

Gln Leu Cys Pro Ile Cys Arg Ala Pro Val
1 5 10

<210> SEQ ID NO 77
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 77

Arg Leu Ala Ser Phe Tyr Asp Trp Pro Leu
1 5 10

<210> SEQ ID NO 78
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 78

Leu Leu Arg Ser Lys Gly Arg Asp Phe Val
1 5 10

<210> SEQ ID NO 79
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 79

Val Leu Glu Pro Pro Gly Ala Arg Asp Val
1 5 10

<210> SEQ ID NO 80
<211> LENGTH: 10
<212> TYPE: PRT
<213> ORGANISM: Artificial Sequence
<220> FEATURE:
<223> OTHER INFORMATION: Sur53K9 peptide

<400> SEQUENCE: 80

Pro Leu Thr Ala Glu Val Pro Pro Glu Leu
1 5 10

<210> SEQ ID NO 81

<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 81

Ser Leu Gly Ser Pro Val Leu Gly Leu
1 5

<210> SEQ ID NO 82
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 82

Gln Ile Leu Gly Gln Leu Arg Pro Leu
1 5

<210> SEQ ID NO 83
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 83

Leu Thr Ala Glu Val Pro Pro Glu Leu
1 5

<210> SEQ ID NO 84
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 84

Gly Met Gly Ser Glu Glu Leu Arg Leu
1 5

<210> SEQ ID NO 85
<211> LENGTH: 9
<212> TYPE: PRT
<213> ORGANISM: Artificial Sequence
<220> FEATURE:
<223> OTHER INFORMATION: Sur53K9 peptide

<400> SEQUENCE: 85

Glu Leu Pro Thr Pro Arg Arg Glu Val
1 5

<210> SEQ ID NO 86
<211> LENGTH: 9
<212> TYPE: PRT
<213> ORGANISM: Artificial Sequence
<220> FEATURE:
<223> OTHER INFORMATION: HLA-A2 peptide

<400> SEQUENCE: 86

Cys Ala Cys Thr Pro Glu Arg Met Ala
1 5

<210> SEQ ID NO 87
<211> LENGTH: 9

-continued

```
<212> TYPE: PRT
<213> ORGANISM: Artificial Sequence
<220> FEATURE:
<223> OTHER INFORMATION: HLA-A2 peptide

<400> SEQUENCE: 87

Cys Thr Pro Glu Arg Met Ala Glu Ala
1               5


<210> SEQ ID NO 88
<211> LENGTH: 9
<212> TYPE: PRT
<213> ORGANISM: Artificial Sequence
<220> FEATURE:
<223> OTHER INFORMATION: HLA-A3 peptide

<400> SEQUENCE: 88

Phe Leu Glu Gly Cys Ala Cys Thr Pro
1               5


<210> SEQ ID NO 89
<211> LENGTH: 10
<212> TYPE: PRT
<213> ORGANISM: Artificial Sequence
<220> FEATURE:
<223> OTHER INFORMATION: HLA-B7/HLA-B35/HLA-B51 peptide

<400> SEQUENCE: 89

Trp Pro Phe Leu Glu Gly Cys Ala Cys Thr
1               5                   10
```

The invention claimed is:

1. An immunogenic composition [consisting of] *comprising* the peptide of the amino acid sequence of SEQ ID NO: 18, *the peptide of the amino acid sequence of SEQ ID NO: 14,* and an adjuvant.

2. An immunogenic composition [consisting of] *comprising* the peptide of the amino acid sequence of SEQ ID NO: 18 *and the peptide of the amino acid sequence of SEQ ID NO: 14, both* coupled to an immunogenic carrier, and an adjuvant.

3. An immunogenic composition [consisting of] *comprising* the peptide of the amino acid sequence of SEQ ID NO: 18, *the peptide of the amino acid sequence of SEQ ID NO: 14,* an adjuvant, and at least one of a pharmaceutical carrier, diluent, preservative, buffer component, or a combination thereof.

*4. The immunogenic composition of claim 1, further comprising the peptide of the amino acid sequence of SEQ ID NO: 5.*

*5. The immunogenic composition of claim 1, further comprising the peptide of the amino acid sequence of SEQ ID NO: 36.*

*6. The immunogenic composition of claim 1, further comprising the peptide of the amino acid sequence of SEQ ID NO: 58.*

*7. An immunogenic composition comprising the peptide of the amino acid sequence of SEQ ID NO: 14, the peptide of the amino acid sequence of SEQ ID NO: 5, the peptide of the amino acid sequence of SEQ ID NO: 18, the peptide of the amino acid sequence of SEQ ID NO: 36, and the peptide of the amino acid sequence of SEQ ID NO: 58.*

*8. The immunogenic composition of claim 7, comprising a plurality of peptides consisting essentially of:*

*the peptide of the amino acid sequence of SEQ ID NO: 14;*
*the peptide of the amino acid sequence of SEQ ID NO: 5;*
*the peptide of the amino acid sequence of SEQ ID NO: 18;*
*the peptide of the amino acid sequence of SEQ ID NO: 36; and*
*the peptide of the amino acid sequence of SEQ ID NO: 58.*

*9. The immunogenic composition of claim 1, wherein the immunogenic composition is capable of eliciting an immune response against a cancer wherein survivin is expressed.*

*10. The immunogenic composition of claim 9, wherein the cancer is a haematopoietic malignancy, melanoma, breast cancer, cervix cancer, ovarian cancer, lung cancer, colon cancer, pancreas cancer, prostate cancer, or combination thereof.*

*11. The immunogenic composition of claim 10, wherein the haematopoietic malignancy includes chronic lymphatic leukemia, chronic myeloid leukemia, or a combination thereof.*

*12. The immunogenic composition of claim 1, wherein the immunogenic composition elicits the production of effector T-cells having a cytotoxic effect against cancer cells.*

*13. The immunogenic composition of claim 7, further comprising an adjuvant.*

*14. The immunogenic composition of claim 8, further comprising an adjuvant.*

*15. The immunogenic composition of claim 8, consisting essentially of:*

*the peptide of the amino acid sequence of SEQ ID NO: 14;*
*the peptide of the amino acid sequence of SEQ ID NO: 5;*
*the peptide of the amino acid sequence of SEQ ID NO: 18;*
*the peptide of the amino acid sequence of SEQ ID NO: 36; and*
*the peptide of the amino acid sequence of SEQ ID NO: 58.*

*16. The immunogenic composition of claim 8, consisting essentially of:*

*the peptide of the amino acid sequence of SEQ ID NO: 14;*
*the peptide of the amino acid sequence of SEQ ID NO: 5;*
*the peptide of the amino acid sequence of SEQ ID NO: 18;*
*the peptide of the amino acid sequence of SEQ ID NO: 36;*
*the peptide of the amino acid sequence of SEQ ID NO: 58;*
*and*
*adjuvant.*

* * * * *